US008877206B2

(12) United States Patent
Chen et al.

(10) Patent No.: US 8,877,206 B2
(45) Date of Patent: Nov. 4, 2014

(54) STIMULATION OF AN IMMUNE RESPONSE BY CATIONIC LIPIDS

(75) Inventors: Weihsu Chen, San Diego, CA (US); Weili Yan, Chapel Hill, NC (US); Kenya Toney, Forest Park, OH (US); Gregory Conn, Cincinnati, OH (US); Frank Bedu-Addo, Liberty Township, OH (US); Leaf Huang, Durham, NC (US)

(73) Assignee: PDS Biotechnology Corporation, North Brunswick, NJ (US)

( * ) Notice: Subject to any disclaimer, the term of this patent is extended or adjusted under 35 U.S.C. 154(b) by 476 days.

(21) Appl. No.: 12/049,957

(22) Filed: Mar. 17, 2008

(65) Prior Publication Data

US 2009/0017057 A1 Jan. 15, 2009

Related U.S. Application Data

(60) Provisional application No. 60/896,412, filed on Mar. 22, 2007, provisional application No. 60/911,549, filed on Apr. 13, 2007, provisional application No. 60/948,512, filed on Jul. 9, 2007, provisional application No. 60/983,799, filed on Oct. 30, 2007.

(51) Int. Cl.
*A61K 38/00* (2006.01)
*A61K 39/39* (2006.01)
*A61K 39/00* (2006.01)
*A61K 31/14* (2006.01)
*A61K 31/20* (2006.01)

(52) U.S. Cl.
CPC ........... *A61K 31/14* (2013.01); *A61K 39/39* (2013.01); *A61K 39/00* (2013.01); *A61K 2039/55555* (2013.01); *A61K 39/0011* (2013.01); *A61K 31/20* (2013.01)
USPC ............... 424/193.1; 424/184.1; 424/196.11; 424/197.11

(58) Field of Classification Search
CPC ........... A61K 2039/53; A61K 39/0011; A61K 2039/55555; A61K 2039/5152
See application file for complete search history.

(56) References Cited

U.S. PATENT DOCUMENTS

| | | | |
|---|---|---|---|
| 5,264,618 A | 11/1993 | Felgner et al. | |
| 5,283,185 A | 2/1994 | Epand et al. | |
| 5,334,761 A | 8/1994 | Gebeyehu et al. | |
| 5,459,127 A | 10/1995 | Felgner et al. | |
| 6,008,202 A | 12/1999 | Huang et al. | |
| 6,124,270 A | 9/2000 | Haensler | |
| 6,214,804 B1 | 4/2001 | Felgner et al. | |
| 6,419,931 B1 | 7/2002 | Vitiello et al. | |
| 6,464,980 B1 | 10/2002 | Fikes et al. | |
| 6,586,409 B1 | 7/2003 | Wheeler | |
| 6,610,321 B2 * | 8/2003 | Huang et al. | 424/450 |
| 6,649,170 B1 | 11/2003 | Lindblad et al. | |
| 6,693,086 B1 | 2/2004 | Dow et al. | |
| 6,710,035 B2 | 3/2004 | Felgner et al. | |
| 6,780,421 B1 | 8/2004 | Haensler et al. | |
| 6,852,334 B1 | 2/2005 | Cullis | |
| 7,001,614 B2 | 2/2006 | Smyth-Templeton et al. | |
| 7,105,574 B1 | 9/2006 | Wheeler | |
| 7,303,881 B2 | 12/2007 | Huang et al. | |
| 2003/0008813 A1 | 1/2003 | Felgner et al. | |
| 2004/0157791 A1* | 8/2004 | Dow et al. | 514/44 |
| 2005/0025822 A1 | 2/2005 | Wong et al. | |
| 2005/0245446 A1 | 11/2005 | Hailes et al. | |
| 2006/0008472 A1* | 1/2006 | Huang et al. | 424/204.1 |
| 2006/0051405 A1 | 3/2006 | MacLachlan et al. | |
| 2006/0083780 A1 | 4/2006 | Heyes et al. | |
| 2006/0165708 A1* | 7/2006 | Mayumi et al. | 424/185.1 |
| 2006/0182793 A1 | 8/2006 | Bachmann et al. | |
| 2006/0204566 A1 | 9/2006 | Smyth-Templeton et al. | |
| 2006/0223769 A1 | 10/2006 | Dow et al. | |
| 2006/0251726 A1 | 11/2006 | Lin et al. | |
| 2006/0275777 A1 | 12/2006 | Waelti | |
| 2007/0059318 A1 | 3/2007 | Balu-Iyer et al. | |
| 2008/0014254 A1 | 1/2008 | Platscher et al. | |
| 2008/0131455 A1 | 6/2008 | Huang et al. | |

FOREIGN PATENT DOCUMENTS

| | | |
|---|---|---|
| WO | WO 93/03764 | 3/1993 |
| WO | WO 95/04542 | 2/1995 |
| WO | WO 00/50006 | 8/2000 |
| WO | WO 00/62813 | 10/2000 |
| WO | WO 01/11067 | 2/2001 |
| WO | WO 01/80900 | 11/2001 |
| WO | 02069369 A2 | 9/2002 |
| WO | 03095641 A1 | 11/2003 |
| WO | WO 2004/014957 | 2/2004 |

OTHER PUBLICATIONS

Iwaoka et al (J of Leukocyte Biology, 27:184-191).*
Credo Reference, 2005.*
Immordino et al (Int J Nanomedicine, 2006, abstract).*
Diamond et al (Blood, 1997, 90:1751-1767).*
Johnson et al, Science, 2002, 298:1911-1912.*
Dow et al (The Journal of Immunology, 1999, 163:1552-1561).*
Iwaoka et al, Journal of Leukocyte Biology,2006, 79:184-191.*
International Search Report mailed Apr. 20, 2009.
International Search Report mailed Jun. 4, 2009.
Ming T. Liang, et al., Encapsulation of Lipopeptides Within Liposomes: Effect of Number of Lipid Chains, Chain Length and Method of Liposome Preparation, International Journal of Pharmaceutics, 2005, pp. 247-254, vol. 301, Elsevier B.V.
Salome Kantengwa, et al., Superoxide Anions Induce The Maturation of Human Dendritic Cells, American Journal of Respiratory and Critical Care Medicine, Feb. 1, 2003, pp. 431-437, vol. 167, No. 3, Divisions of Pneumology and Thoracic Surgery, University Hospital, Geneva, Switzerland.
Kei Tobiume, et. al., ASK1 Is Required for Sustained Activations of JNL/p38 MAP Kinases and Apoptosis, EMBO Reports, 2001, pp. 222-228, vol. 2, No. 3, European Molecular Biology Organization.
Yukihiko Aramaki, et al., Induction of Apoptosis in WEHI 231 Cells by Cationic Liposomes, Pharmaceutical Research, Jan. 18, 2000, pp. 515-520, vol. 17, No. 5, Plenum Publishing Corporation.

(Continued)

*Primary Examiner* — Misook Yu
*Assistant Examiner* — Julie Wu
(74) *Attorney, Agent, or Firm* — Barnes & Thornburg LLP

(57) ABSTRACT

The present invention provides compositions and methods for stimulating an immune response using cationic lipids alone or in combination with antigens.

44 Claims, 25 Drawing Sheets
(1 of 25 Drawing Sheet(s) Filed in Color)

(56) References Cited

OTHER PUBLICATIONS

Sayaka Iwaoka, et al., Cationic Liposomes Induce Apoptosis Through p38 MAP Kinase-Caspase-8-Bid Pathway in Macrophage-Like RAW264.7 Cells, Journal of Leukocyte Biology, Jan. 2006, pp. 184-191, vol. 79, Society for Leukocyte Biology.

Patricia E. Rao, et al., Differentiation and Expansion of T Cells With Regulatory Function From Human Peripheral Lymphocytes by Stimulation in the Presence of TGF-B, The Journal of Immunology, 2005, pp. 1446-1455, vol. 174, The American Association of Immunologists, Inc.

Kayo Inaba, et al., Generation of Large Numbers of Dendritic Cells From Mouse Bone Marrow Cultures Supplemented With Granulocyte/Macrophage Colony-Stimulating Factor, Journal of Experimental Medicine, Dec. 1992, pp. 1693-1702, vol. 176, The Rockefeller University Press.

Hui Wang, et al., Potential Involvement of Monocyte Chemoattractant Protein (MCP)-1/CCL2 in IL-4-Mediated Tumor Immunity Through Inducing Dendritic Cell Migration Into the Draining Lymph Nodes, International Immunopharmacology, 2003, pp. 627-642, vol. 3, Elsevier Science B.V.

Naoki Okada, et al., Effects of Lipofectin-Antigen Complexes on Major Histocompatibility Complex Class I-Restricted Antigen Presentation Pathway in Murine Dendritic Cells and on Dendritic Cell Maturation, Biochimica et Biophysica Acta, 2001, pp. 97-101, vol. 1527, Elsevier Science.

Jae Kwang Yoo, et al., IL-18 Induces Monocyte Chemotactic Protein-1 Production in Macrophages Through the Phosphatidylinositol 3-Kinase/Akt and MEK/ERK1/2 Pathways, The Journal of Immunology, 2005, pp. 8280-8286, vol. 175, The American Association of Immunologists, Inc.

Gregory Gregoriadis, et al., Vaccine Entrapment in Liposomes, Methods, 1999, pp. 156-162, vol. 19, Acade.

Y. Perrie, et al., Liposome-Mediated DNA Immunisation Via The Subcutaneous Route, Journal of Drug Targeting, 2003, pp. 555-563, vol. 11 (8-10), Taylor & Francis Ltd.

Melissa J. Copland, et al., Lipid Based Particulate Formulations for the Delivery of Antigen, Immunology and Cell Biology, 2005, pp. 97-105, vol. 83, Australasian Society for Immunology Inc.

Ghania Chikh, et al., Liposomal Delivery of CTL Epitopes to Dendritic Cells, Bioscience Reports, Apr. 2002, pp. 339-353, vol. 22, No. 2, Plenum Publishing Corporation.

Peter Anderson, Effective Vaccination of Mice Against *Mycobacterium tuberculosis* Infection With a Soluble Mixture of Secreted Mycobacterial Proteins, Jun. 1994, pp. 2536-2544, vol. 62, No. 6, American Society for Microbiology.

P. Moingeon, et al., Towards the Rational Design of Th1 Adjuvants, Vaccine, 2001, pp. 4363-4372, vol. 19, Elsevier Science Ltd.

Olga Kogkopoulou, et al., Conditional Up-Regulation of IL-2 Production by p38 MAPK Inactivation is Mediated by Increased ERK1/2 Activity, Journal of Leukocyte Biology, May 2006, vol. 79, Society for Leukocyte Biology.

Hong Zhang, Stress-Induced Inhibition of ERK1 and ERK2 by Direct Interaction With p38 MAP Kinase, The Journal of Biological Chemistry, Mar. 9, 2001, pp. 6905-6908, vol. 276, No. 10, The American Society for Biochemistry and Molecular Biology, Inc.

Akiko Hasegawa, Nasal Immunization With Diphtheria Toxoid Conjugated-CD52 Core Peptide Induced Specific Antibody Production in Genital Tract of Female Mice, American Journal of Reproductive Immunology, 2002, pp. 305-311, vol. 48, Blackwell Munksgaard.

Li Wang, et al., Lysophosphatidylcholine-Induced Surface Redistribution Regulates Signaling of the Murine G Protein-Coupled Receptor G2A, Molecular Biology of the Cell, May 2005, pp. 2234-2247, vol. 16, The American Society for Cell Biology.

Dimuthu R. Desilva, et al., The p38 Mitogen-Activated Protein Kinase Pathway in Activated and Anergic Th1 Cells, Cellular Immunology, 1997, pp. 116-123, vol. 180, Academic Press.

Jeffrey J. Yu, et al., Regulation and Phenotype of an Innate Th1 Cell: Role of Cytokines and the p38 Kinase Pathway, The Journal of Immunology, 2003, pp. 6112-6118, vol. 171, The American Association of Immunologists.

Chen Dong, et al., MAP Kinases in the Immune Response, Annual Review of Immunology, 2002, pp. 55-72, vol. 20, Annual Reviews.

Jerome Connor, et al., pH-Sensitive Immunoliposomes as an Efficient and Target-Specific Carrier for Antitumor Drugs, Cancer Research, Jul. 1986, pp. 3431-3435, vol. 46, Department of Biochemistry, University of Tennessee, Knoxville, Tennessee.

Diana Felnerova, et al., Liposomes and Virosomes as Delivery Systems for Antigens, Nucleic Acids and Drugs, Current Opinion in Biotechnology, 2004, pp. 518-529, vol. 15, Elsevier Ltd.

Shyh-Dar Li, et al., Targeted Delivery of Antisense Oligodeoxynucleotide and Small Interference RNA Into Lung Cancer Cells, Molecular Pharmaceutics, 2006, pp. 579-588, vol. 3, No. 5, American Chemical Society.

Zhengrong Cui, et al., Liposome-Polycation-DNA (LPD) Particle as a Carrier and Adjuvant for Protein-Based Vaccines: Therapeutic Effect Against Cervical Cancer, Cancer Immunology and Immunother, 2005, pp. 1180-1190, Springer-Verlag.

John Dileo, et al., Lipid-Protamine-DNA-Mediated Antigen Delivery to Antigen-Presenting Cells Results in Enhanced Anti-Tumor Immune Responses, Molecular Therapy, May 2003, pp. 640-648, vol. 7, No. 5, The American Society of Gene Therapy.

Carl R. Alving, Design and Selection of Vaccine Adjuvants: Animal Models and Human Trials, Vaccine, 2002, pp. S56-S64, vol. 20, Elsevier Science Ltd.

Hanne Gahery-Segard, et al., Multiepitopic B- and T-Cell Responses Induced in Humans by a Human Immunodeficiency Virus Type 1 Lipopeptide Vaccine, Journal of Virology, Feb. 2000, pp. 1694-1703, vol. 74, No. 4, American Society for Microbiology.

G. Pialoux, et al., Lipopeptides Induce Cell-Mediated Anti-HIV Immune Responses in Seronegative Volunteers, Official Journal of the International of AIDS, Jul. 6, 2001, pp. 1239-1249, vol. 15, No. 10, Lippincott Williams & Wilkins, Inc.

Lbachir Benmohamed, et al., Lipopetide Immunization Without Adjuvant Induces Potent and Long-Lasting B, T Helper, and Cytotoxic T Lymphocyte Resonses Against a Malaria Liver Stage Antigen in Mice and Chimpanzees, European Journal of Immunology, 1997, pp. 1242-1253, vol. 27, VCH Verlagsgesellschaft.

Zeina A Kanafani, et al., Daptomycin: A Rapidly Bactericidal Lipopeptide for the Treatment of Gram-Positive Infections, Experimental Review of Antibacterial Infections, 2007, pp. 177-184, vol. 5, No. 2, Future Drugs Ltd.

David W. Denning, et al., Micafungin (FK463), Alone or in Combination With Other Systemic Antifungal Agents, for the Treatment of Acute Invasive Aspergillosis, Journal of Infection, 2006, pp. 337-349, vol. 53, Elsevier Ltd.

Anthony M. Byers, et al., Cutting Edge: Rapid In Vivo CTL Activity by Polyoma Virus-Specific Effector and Memory CD8+ T Cells, The Journal of Immunology, 2003, pp. 17-21, vol. 171, The American Association of Immunologists, Inc.

Cornelis J. M. Melief, et al., Effective Therapeutic Anticancer Vaccines Based on Precision Guiding of Cytolytic T Lymphocytes, Immunological Reviews, 2002, pp. 177-182, vol. 188, Blackwell Munksgaard.

Isabelle Fernandes, et al., Synthetic Lipopeptides Incorporated in Liposomes: In Vitro Stimulation of the Profliferation of Murine Splenocytes and In Vivo Induction of an Immune Response Against a Peptide Antigen, Molecular Immunology, 1997, pp. 569-576, vol. 34, No. 8/9, Elsevier Ltd.

Andre F.M. Verheul, Monopalmitic Acid-Peptide Conjugates Induce Cytotoxic T Cell Responses Against Malarial Epitopes: Importance of Spacer Amino Acids, Journal of Immunological Methods, 1995, pp. 219-226, vol. 182, Elsevier Science B.V.

Michelle Woldemar Carr, et al. Monocyte Chemoattractant Protein 1 Acts As a T-Lymphocyte Chemoattractant, Proceedings of the National Academy of Sciences, of The United States of America, Apr. 1994, pp. 3652-3656, vol. 91, Committee on Immunology and Department of Pathology, Harvard Medical School, Department of Cardiology, Childen's Hospital, and The Center for Blood Research, Boston, Massachusetts.

Flora Castellino, et al., Chemokine-Guided CD4+ T Cell Help Enhances Generation of IL-6Ra high IL-7Ra high Prememory CD8+ T Cells, The Journal of Immunology, 2007, pp. 778-787, vol. 178,

(56) References Cited

OTHER PUBLICATIONS

Lymphocyte Biology Section, Laboratory of Immunology, National Institute of Allergy and Infectious Diseases, National Institutes of Health, Bethesda, Maryland.
Flora Castellino, et al., Chemokines Enhance Immunity by Guiding Naive CD8+ T Cells to Sites of CD4+ T Cell-Dendritic Cell Interaction, Nature, Apr. 13, 2006, pp. 890-895, vol. 440, Lymphocyte Biology Section, Laboratory of Immunology, National Institute of Allergy and Infectious Diseases, National Institutes of Health, Bethesda, Maryland.
Stephanie Dillon, et al., A Toll-Like Receptor 2 Ligand Stimulates Th2 Responses In Vivo, via Induction of Extracellular Signal-Regulated Kinase Mitogen-Activated Protein Kinase and c-Fos in Dendritic Cells, The Journal of Immunology, 2004, pp. 4733-4743, vol. 172, The American Association of Immunologists, Inc.
Helena Helmby, et al., Interleukin-1 Plays a Major Role in the Development of Th2-Mediated Immunity, European Journal of Immunology, 2004, pp. 3674-3681, vol. 34, Whiley-VCH GmbH & Co.
Lothar Hultner, In Activated Mast Cells, IL-1 Up-Regulates the Production of Several Th2-Related Cytokines Including IL-9, The Journal of Immunology, 2000, pp. 5556-5563, vol. 164, The American Association of Immunologists.
Tadao Ishida, et al., Defective Function of Langerhans Cells in Tumor-Bearing Animals is the Result of Defective Maturation From Hemopoietic Progenitors, The Journal of Immunology, 1998, pp. 4842-4851, vol. 161, The American Association of Immunologists.
Anand Jacob, et al., Convergence of Signaling Pathways on the Activation of ERK in B Cells, The Journal of Biological Chemistry, Jun. 28, 2002, pp. 23420-23426, vol. 277, No. 26, The American Society for Biochemistry and Molecular Biology, Inc.
Janusz H.S. Kabarowski, et al., Lysophospatidylcholine as a Ligand for the Immunoregulatory Receptor G2A, Science, Jul. 27, 2001, pp. 702-705, vol. 293, Department of Microbiology, Immunology, and Molecular Genetics; Department of Cancer Biology, Lerner Research Institute, Cleveland, Ohio.
Jong J. Kim, et al., CD8 Positive T Cells Influence Antigen-Specific Immune Responses Through the Expression of Chemokines, Journal of Clinical Investigation, Sep. 1998, pp. 1112-1124, vol. 102, No. 6, The American Society for Clinical Investigation, Inc.
Jacques Banchereau, et al., Dendritic Cells and the Control of Immunity, Nature, 1998, Macmillan Publishers Ltd.
Charles R. Mackay, Chemokines: Immunology's High Impact Factors, Nature Immunology, Feb. 2001, pp. 95-101, vol. 2, No. 2, Nature Publishing Group.
Naoko Sato, et al., CC Chemokine Receptor (CCR) 2 is Required for Langhans Cell Migration and Localization of T Helper Cell Type 1 (Th1) -Inducing Dendritic Cells: Absence of CCR2 Shifts the *Leishmania* Major-Resistant Phenotype to a Susceptible State Dominated by Th2 Cytokines, B Cell Outgrowth, and Sustained Neutrophilic Inflammation, Journal of Experimental Medicine, Jul. 17, 2000, vol. 192, No. 2, The Rockefeller University Press.
Shawn M. Sumida, et al, Recruitment and Expansion of Dendritic Cells In Vivo Potentiate the Immunogenicity of Plasmid DNA Vaccines, The Journal of Clinical Investigation, Nov. 2004, pp. 1334-1342, vol. 114, No. 9, USA.
Akiko Uemura, et al., Induction of Immune Responses Against Glycosphingolipid Antigens: Comparison of Antibody Responses in Mice Immunized With Antigen Associated With Liposomes Prepared From Various Phospholipids, Journal of Veterinary Medical Science, 2005, pp. 1197-1201, vol. 67, No. 12, Laboratory of Veterinary Immunology, Division of Veterinary Science, Graduate School of Life and Environmental Sciences, Osaka Prefecture University, Sakai, Osaka, Japan.
M Whitmore, et al., LPD Lipopolyplex Initiates a Potent Cytokine Response and Inhibits Tumor Growth, Gene Therapy, 1999, pp. 1867-1875, vol. 6, Stockton Press.
Teizo Yoshimura, et al., Human Monocyte Chemoattractant Protein-1 (MCP-1), Full Length cDNA Cloning, Expression in Mitogen-Stimulated Blood Mononucleur Leukocytes, and Sequence Similarity to Mouse Competence Gene JE, Federation of European Biochemical Societies, Feb. 1989, pp. 487-493, vol. 244, No. 2, Elsevier Science Publishers B.V.
Chen and Huang, "Cationic Liposome-based Peptide Vaccine: Potent Therapeutics for Cervical Cancer", Poster, May 20, 2006.
Brunel, et al., "Cationic Lipid DC-Chol Induces an Improved and Balanced Immunity Able to Overcome the Unresponsiveness to the Hepatitis B Vaccine", Vaccine, Apr. 1999, pp. 2192-2203, vol. 17.
Walker, et al., "Cationic Lipids Direct a Viral Glycoprotein Into the Class I Major Histocompatibility Complex Antigen-Presentation Pathway", Proc. Natl. Acad. Sci. USA, Sep. 1992, pp. 7915-7918, vol. 89.
Joseph, et al., "A New Intranasal Influenza Vaccine Based on a Novel Polycationic Lipid-Ceramide Carbamoyl-Spermine (CCS) I. Immunogenicity and Efficacy Studies in Mice", Vaccine, 2006, pp. 3990-4006, vol. 24.
Jiao, et al., "Modulation of Cellular Immune Response Against Hepatitis C Virus Nonstructural Protein 3 by Cationic Liposome Encapsulated DNA Immunization", Hepatology, Feb. 2003, pp. 452-460, vol. 37, No. 2.
Yasuda, et al., "Endosomal Translocation of Vertebrate DNA Activates Dendritic Cells via TLR9-Dependent and Independent Pathways", The Journal of Immunology, 2005, pp. 6129-6136, vol. 174.
Holten-Anderson, et al., "Combination of the Cationic Surfactant Dimethyl Dioctadecyl Ammonium Bromide and Synthetic Mycobacterium Bovis Bacillus Calmette-Guerin and Adjuvant Activity In Vivo", Infection and Immunity, Mar. 2004, pp. 1608-1617, vol. 72, No. 3.
Sprott, et al., "Activation of Dendtritic Cells by Liposomes Prepared from Phosphatidylinositol Mannosides from *Mycobacterium bovis* Bacillus Calmette-Guerin and Adjuvant Activity in Vivo", Infection and Immunity, Sep. 2004, pp. 5235-5246, vol. 72, No. 9.
Zaks, et al., "Efficient Immunization and Cross-Priming by Vaccine Adjuvants Containing TLR3 or TLR9 Agonists Complexed to Cationic Liposomes", The Journal of Immunology, 2006, pp. 7335-7345, vol. 176.
Korsholm, "Unravelling the Adjuvant Mechanism of Cationic Liposomes", Statens Serum Institute, Jun. 2006, 15.00-15.30.
Rughetti, et al., "Transfected Human Dendritic Cells to Induce Antitumor Immunity", Sep. 2000, pp. 1458-1466, vol. 7, No. 17.
Cui, et al., "Coating of Mannan on LPD Particles Containing HPV E7 Peptide Significantly Enhances Immunity Against HPV-Positive Tumor", Jun. 2004, pp. 1018-1025, vol. 21, No. 6.
Steller, et al., Clinical Cancer Research, 1998, vol. 4, pp. 2103-2109.
United States Patent and Trademark Office, Official Action, U.S. Appl. No. 11/121,840, mailed Jun. 4, 2007, 5 pages.
United States Patent and Trademark Office, Official Action, U.S. Appl. No. 11/121,840, mailed Sep. 7, 2007, 6 pages.
Zhengrong Cui, et al., Immunostimulation Mechanism of LPD Nanoparticle as a Vaccine Carrier, 2005, pp. 22-28, vol. 2, No. 1, American Chemical Society.
Caius G. Radu, et al., T Cell Chemotaxis to Lysophosphatidylcholine Through the G2A Receptor, PNAS, Jan. 6, 2004, pp. 245-250, vol. 101, No. 1, The National Academy of Sciences of the USA.
Filion et al. (1998) "Major limitations in the use of cationic liposomes for DNA delivery," Int J Pharmaceutics 162(1-2):159-17.
Filion et al. (1997) "Anti-inflammatory activity of cationic lipids," Brit. J Pharm 122(3):551-557.
Lonez et al., "Cationic Liposomal Lipids: From Gene Carriers to Cell Signaling," Progress in Lipid Research 2008, 47: 340-347.
Korsholm et al., "The Adjuvant Mechanism of Dimethyldioctadecyl-ammonium Liposomes," Immunology, Jun. 2007, 121 (2).
Chen et al., "A simple but effective cancer vaccine consisting of an antigen and a cationic lipid," Cancer Immunology and Immunotherapy, 2008, 57: (4) 517-530.
Weili Yan, et al., Mechanism of Adjuvant Activity of Cationic Liposome: Phosphorylation of a Map Kinase, ERK and Induction of Chemokines, Division of Molecular Pharmaceutics, School of Pharmacy, University of North Carolina, Chapel Hill, pp. 1-40, Chapel Hill, North Carolina, USA, (2009).
Weihsu Chen, et al., A Simple and Effective Cancer Vaccine Consisting of an Antigen and a Cationic Lipid, Division of Molecular

(56) References Cited

OTHER PUBLICATIONS

Pharmaceutics, School of Pharmacy, University of North Carolina, Chapel Hill, pp. 1-48, Chapel Hill, North Carolina, USA, (2009).

Gregory Gregoriadis, Immunological Adjuvants: A Role for Liposomes, Immunology Today, 1990, pp. 89-97, vol. 11, No. 3, The School of Pharmacy, University of London, London.

Rong-Fu Wang, et al., Enhancement of Antitumor Immunity by Prolonging Antigen Presentation on Dendritic Cells, Nature Biotechnology, Feb. 2002, pp. 149-154, vol. 20, Nature Publishing Group.

Frederick R. Vogel, Improving Vaccine Performance With Adjuvants, Clinical Infectious Diseases, 2000, pp. S266-S270, vol. 30, Suppl. 3, Infectious Diseases Society of America.

Clare Baecher-Allan, et al., Immune Regulation in Tumor-Bearing Hosts, Current Opinion in Immunology, 2006, pp. 214-219, vol. 18, Elsevier Ltd.

Marc Dupuis, et al., Dendritic Cells Internalize Vaccine Adjuvant After Intramuscular Injection, Cellular Immunology, 1998, pp. 18-27, vol. 186, Academic Press.

M. Minutello, et al., Safety and Immunogenicity of an Inactivated Subunit Influenza Virus Vaccine Combined With MF59 Adjuvant Emulsion in Elderly Subjects, Immunized for Three Consecutive Influenza Seasons, Vaccine, 1999, pp. 99-104, vol. 17, Elsevier Science Ltd.

Elisa Brunette, et al., Lipofection Does Not Require the Removal of Serum, Nucleic Acids Research, Dec. 26, 1991, p. 1151, vol. 20, No. 5, Cancer Research Institute, University of California San Francisco Medical Center, San Francisco, California.

Peter A. Cohen, et al., CD4+ T-Cells From Mice Immunized to Syngeneic Sarcomas Recognize Distinct, Non-Shared Tumor Antigens, Cancer Research, Feb. 15, 1994, pp. 1055-1058, vol. 54, Branches of Surgery and Dermatology, National Cancer Institute, National Institute of Health, Bethesda, Maryland.

Melissa B. Lodeon, et al., Natural Killer Cells as an Initial Defense Against Pathogens, Current Opinion in Immunology, 2006, pp. 391-398, vol. 18, Elsevier Ltd.

Feltcamp MC, et al., Vaccination With Cytotoxic T Lymphocyte Epitope-Containing Peptide Protects Against a Tumor Induced by Human Papillomavirus Type 16-Transformed Cells, European Journal of Immunology, Sep. 1993, pp. 2242-2249, vol. 23, No. 9, PubMed.

D.D. Eardley, et al., Immunoregulatory Circuits Among T-Cell Sets I. T-Helper Cells Induce Other T-Cell Sets to Exert Feedback, Journal of Experimental Medicine, 1978, pp. 1106-1115, The Rockefeller University Press.

H. Cantor, et al., Immunoregulatory Circuits Among T-Cell Sets II. Physiologic Role of Feedback Inhibition in Vivo: Absence in NZB Mice, Journal of Experimental Medicine, 1978, pp. 1116-1125, The Rockefeller University Press.

Clare Baecher-Allan, et al., Suppressor T Cells in Human Diseases, Journal of Experimental Medicine, Aug. 2, 2004, pp. 273-276, vol. 200, No. 3, The Rockefeller University Press.

Alberto Comes, et al., CD25+ Regulatory T Cell Depletion Augments Immunotherapy of MicroMetastases by an IL-21-Secreting Cellular Vaccine1, The Journal of Immunology, 2006, pp. -1750-1758, The American Association of Immunologists, Inc.

Galina V. Yamshchikov, et al., Evaluation of Peptide Vaccine Immunogenicity in Draining Lymph Nodes and Peripheral Blood of Melanoma Patients, International Journal of Immunology, 2001, pp. 703-711, vol. 92, Wiley-Liss, Inc.

Herio Toledo, et al., A Phase I Clinical Trial of a Multi-Epitope Polypeptide TAB9 Combined With Montanide ISA 720 Adjuvant in Non-HIV-1 Infected Human Volunteers, Vaccine, 2001, pp. 4328-4336, vol. 19, Elsevier Science Ltd.

* cited by examiner

STIMULATION OF AN IMMUNE RESPONSE BY CATIONIC LIPIDS

CROSS REFERENCE TO RELATED APPLICATIONS

This application claims benefit of U.S. Provisional Application No. 60/896,412, filed on Mar. 22, 2007, by Weishu Chen and Leaf Huang, and entitled "Cationic-Lipid Based Immune Stimulant for Treatment of Disease"; 60/911,549, filed on Apr. 13, 2007, by Leaf Huang and Weishu Chen, and entitled "Cationic-Lipid Based Dual Function Delivery System and Immune Stimulant for Treatment of Disease"; 60/948,512, filed on Jul. 9, 2007, by Leaf Huang, Weishu Chen, and Weili Yan, and entitled "Cationic-Lipid Based Dual Function Delivery System and Immune Stimulant for Treatment of Disease"; and 60/983,799, filed on Oct. 30, 2007, by Weishu Chen and Leaf Huang, and entitled "Induction of Immune Responses by a Liposomal Peptide Formulation," the disclosures of which are incorporated by reference herein in their entireties.

FIELD OF THE INVENTION

The present invention generally relates to stimulating an immune response, and more particularly to the role of lipids in immune responses.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Development of safe and effective immunotherapies for human use remains an urgent medical need for patients worldwide. In order to elicit appropriate immune responses, immunologic modifiers ("immunomodifiers") that enhance, direct, or promote an immune response can be used in vaccine design or immunotherapy [Gregoriadis, G., *Immunological adjuvants: a role for liposomes*. Immunol Today 11:89 (1990)]. For example, vaccines may include antigens to stimulate an immune response. However, some potential vaccines that include antigens are weak stimulators of an immune response because the vaccines do not efficiently deliver the antigen to antigen presenting cells ("APC") of the immune system and/or the antigen is weakly immunogenic. Thus, immunotherapies that effectively deliver antigens to APC, and also stimulate the immune system to respond to the antigen, are needed. Immunomodifiers have the potential to function as such an immunotherapy. Such immunotherapies may have these and other benefits. For example, when included as part of a therapeutic vaccine, an immunomodifier should at least (1) improve antigen delivery and/or processing in the APC [Wang, R. F., and Wang, H. Y. *Enhancement of antitumor immunity by prolonging antigen presentation on dendritic cells*. Nat Biotechnol 20:149 (2002)], (2) induce the production of immunomodulatory cytokines that favor the development of immune responses to the vaccine antigen, thus promoting cell mediated immunity, including cytotoxic T-lymphocytes ("CTL"), (3) reduce the number of immunizations or the amount of antigen required for an effective vaccine [Vogel, F. R. *Improving vaccine performance with adjuvants*. Clin Infect Dis 30 Suppl 3:S266 (2000)], (4) increase the biological or immunological half-life of the vaccine antigen, and (5) overcome immune tolerance to antigen by inhibiting immune suppressive factors [Baecher-Allan, C., and Anderson, D. E. *Immune regulation in tumor-bearing hosts*. Curr Opin Immunol 18:214 (2006)].

Presently, the primary class of agents used to enhance the efficacy of antigens, such as peptide or protein antigens, in eliciting an immune response are adjuvants such as water-in-oil emulsions, alum, and other chemicals which enhance antigen responses; however, these adjuvants are not immunomodifiers, as described above, because they have no direct immunomodulatory effects themselves [Vogel, F. R., and Powell, M. F. *A compendium of vaccine adjuvants and excipients*, Pharm Biotechnol 6:141 (1995)]. Several such adjuvants are available for use in animals and some of them have been tested in clinical trials. In addition to traditional adjuvants such as the aluminum salts, products such as influenza virosomes [Gluck, R., and Walti, E. 2000. *Biophysical validation of Epaxal Berna, a hepatitis A vaccine adjuvanted with immunopotentiating reconstituted influenza virosomes (IRIV)*. Dev Biol (Basel) 103:189 (2000)] and Chiron's MF59 [Kahn, J. O., et al. *Clinical and immunologic responses to human immunodeficiency virus (HIV) type 1SF2 gp120 subunit vaccine combined with MF59 adjuvant with or without muramyl tripeptide dipalmitoyl phosphatidylethanolamine in non-HIV-infected human volunteers*. J Infect Dis 170:1288 (1994)], which have intrinsic immune effects, are being marketed. For example, MF59, which is a submicron emulsion based adjuvant, is internalized by dendritic cells [Dupuis, M., et al., *Dendritic cells internalize vaccine adjuvant after intramuscular injection*. Cell Immunol 186:18 (1998)]. However, according to clinical trial reports on HSV and influenza vaccines [Jones, C. A., and Cunningham, A. L. *Vaccination strategies to prevent genital herpes and neonatal herpes simplex virus (HSV) disease*. Herpes 11:12 (2004); Minutello, M. et al., *Safety and immunogenicity of an inactivated subunit influenza virus vaccine combined with MF59 adjuvant emulsion in elderly subjects, immunized for three consecutive influenza seasons*. Vaccine 17:99 (1999)], evidence from animal models suggests that the MF59 adjuvant enhances production of neutralizing antibodies rather than enhancing T-cell responses. Thus new methods of stimulating cell mediated immune responses are needed.

Further, as mentioned above, some antigens are weak stimulators of an immune response. Thus, in addition to co-administering antigen with substances that stimulate immune responses, as described above, a weakly immunogenic antigen can be modified to increase its immunogenicity. For example, a weakly immunogenic antigen can be coupled to immunogenic peptides, polysaccharides, or lipids to increase its immunogenicity. However, simply coupling weakly immunogenic antigens to these types of compounds may not be sufficient to elicit an immune response. For example, the resulting immune response may be directed to immunogenic epitopes on the coupled compound and not the weak antigen, or the coupled antigen may not be efficiently delivered APC of the immune system. Thus, additional methods are needed to stimulate immune responses to antigens that are weakly immunogenic.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

This invention is directed to the use of cationic lipids, which under certain dose and composition conditions act as a novel class of immune-stimulants, to (1) effectively present or deliver an antigen to the immune system and (2) stimulate the immune system to respond to the antigen.

Liposomes have been extensively used for delivering small molecular weight drugs, plasmid DNA, oligonucleotides, proteins, and peptides. Vaccines using liposomal vehicles as non-viral antigen carriers are preferable compared to traditional immunizations using live attenuated vaccines or viral vectors such as vaccinia or influenza virus. U.S. Pat. No. 7,303,881, describes a simple yet effective lipid-based immunotherapy, a cationic lipid/antigen complex, which consists of two molecules, the cationic lipid and an antigen, and to which additional components such as stabilizers, adjuvants and surface modifiers could be added [See U.S. Pat. No. 7,303,881]. The formulation, which consists of a cationic lipid, and an antigen [e.g., E7, a human papilloma virus ("HPV")], induces both preventative and therapeutic anti-tumor immune responses against HPV-positive TC-1 tumor in a mouse model. The results demonstrate that the cationic liposome complexed with an antigen serves to stimulate immune responses and initiate dendritic cell (an APC) interaction with T-cells.

In the present invention, additional studies performed to further understand the ability of the cationic lipid/antigen complex to induce a potent immune response, have led to the discovery that the cationic lipids on their own can act as potent immune activators under low dose conditions by activating components of the mitogen-activated protein ("MAP") kinase signaling pathway, which exists in all mammalian species. In combination with an antigen, the cationic lipid/antigen complex, under low dose conditions, induces strong immune responses specific to the antigen formulated in the complex. At higher cationic lipid doses, reactive oxygen species (ROS) are produced in excess in the immune cells and dampens the observed immune response.

Thus, one aspect of the invention provides a composition of at least one cationic lipid in a dose sufficient to induce an immune response in a subject by activating MAP kinase signaling by the cells of the immune system of a subject.

Another aspect of the invention provides a method of inducing an immune response in a subject by activating the MAP kinase signaling pathway by administering a cationic lipid to the subject.

Another aspect of the invention provides a composition of at least one cationic lipid in a dose sufficient to induce an immune response by inducing the production of reactive oxygen species ("ROS") in the cells of the immune system of the subject. The cationic lipid complex stimulates ROS production to levels sufficient to increase the immune response above the immune response present in the absence of the at least one cationic lipid.

Another aspect of the invention provides a method of inducing immune response by administering to a subject a cationic lipid complex to induce the production of reactive oxygen species ("ROS") in the cells of the immune system of the subject. The cationic lipid complex stimulates ROS production to levels sufficient to increase the immune response above the immune response present in the absence of the at least one cationic lipid. Additional aspects of the invention involve the addition of at least one antigen to form a cationic lipid/antigen complex in which case the immune response is antigen-specific.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

Various features, aspects, and advantages of the present invention will become better understood when the following detailed description is read with reference to the accompanying figures in which like characters represent like parts throughout the figures, wherein:

FIGS. 23, A-E, illustrate stimulation of CD 80 by DOTAP/E7, CD 83 by DOTAP/E7, CD 86 by DOTAP/E7, CD 80 by DOEPC/E7 and DOTAP/Cholesterol/E7, and CD 83 by DOEPC/E7 and DOTAP/Cholesterol/E7 respectively.

FIGS. 24 A-F illustrate production of TNF-α, IL-12, CCL3, CCL4, CC15, and CCL-19 respectively.

DETAILED DESCRIPTION

Figure 1:
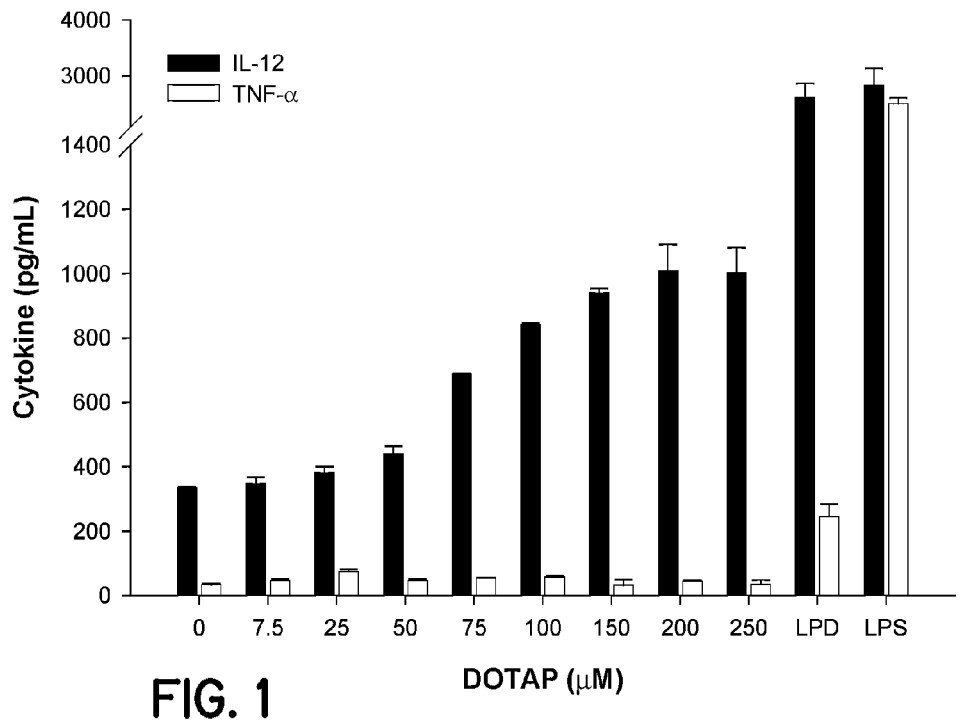
FIG. 1 is a graph depicting in vitro cytokine production after stimulation of dendritic cells with 1,2-dioleoyl-3-trimethylammonium propane ("DOTAP").

One or more specific embodiments of the present invention will be described below. In an effort to provide a concise description of these embodiments, all features of an actual implementation may not be described in the specification. It should be appreciated that in the development of any such actual implementation numerous implementation-specific decisions must be made to achieve the developers' specific goals, which may vary from one implementation to another.

Moreover, it should be appreciated that such a development effort might be complex and time consuming, but would nevertheless be a routine undertaking for those of ordinary skill having the benefit of this disclosure.

When introducing elements of the present invention (e.g., the exemplary embodiments(s) thereof), the articles "a", "an", "the" and "said" are intended to mean that there are one or more of the elements. The terms "comprising", "including" and "having" are intended to be inclusive and mean that there may be additional elements other than the listed elements.

One aspect of the present invention provides a cationic lipid to produce an immune response in a mammal to prevent or treat disease. The cationic lipid can function independently as an immunomodulator, in a dose dependent manner, such as for production of chemokines and/or cytokines, by activating various components of the MAP kinase signaling pathway. The optimal dose range is observed to differ within various mammalian species. In the rodent species for example the optimal cationic lipid dose may range between 50-300 nmole. The specific doses and compositions described herein are merely exemplary and one skilled in the art can determine the doses appropriate for use in a given subject. In another aspect, the cationic lipid in a low dose range may be associated with antigens or drugs for presentation to cells of the immune system while simultaneously stimulating a strong antigen-specific immune response. In some aspects of the invention, the antigen is a lipopeptide.

U.S. Pat. No. 7,303,881 discloses that multiple cationic lipids complexed with disease-associated antigens were shown to stimulate a prophylactic immune response that prevented the specific disease (e.g., HPV-positive cancer) and also a therapeutic immune response that killed cells expressing the particular antigen and resulted in an effective treatment of the disease. Presently, studies were performed to further understand the immunostimulatory capability of cationic lipids using DOTAP, DOEPC, and propyl-N,N,N-trimethyl ammonium chloride ("DOTMA"), three cationic lipids that fall into a broad class of lipids demonstrated to function as immunostimulators in the above referenced patent. These studies have led to the discovery that cationic lipids can function independently as immunodulators within certain low dose ranges or compositions to stimulate an immune response with (or without) antigens. When cationic lipids are complexed with an antigen, an antigen specific immune response is generated.

In another aspect, the cationic lipid compositions of the present invention administered under certain dose conditions presently described stimulate the induction of various components of the MAP kinase signaling pathway and activate the body's immune response to fighting disease, while concurrently delivering antigens to the cells of the immune system. As demonstrated in the examples below, cationic lipids induce the production of reactive oxygen species ("ROS") production in a dose dependent manner. However, beyond the optimal dose of cationic lipid, high ROS production induces apoptosis in cells of the immune system dampening the ability of the lipid to generate a strong immune response. The production of a specific range of ROS, in turn, results in the production of cytokines and chemokines to regulate an immune response. Thus, the optimal dose of cationic lipid is an amount that effectively stimulates levels of ROS production sufficient to stimulate an increase in the immune response above an immune response present in the absence of a cationic lipid (while not stimulating excess ROS production sufficient to induce significant amounts of apoptosis in immune system cells, i.e., enough apoptosis to dampen the immune response) and activates the MAP kinase signaling pathway. As described above, the optimal dose may vary among species and is easily determined by one having ordinary skill in the art.

In yet another aspect, the cationic lipid, at optimal dose, is administered in combination with an antigen or antigens. In this case the cationic lipid/antigen combination is capable of generating an immune response that is specific to the antigen(s) delivered in combination with the cationic lipid. The response generated may include production of specific cytotoxic T cells, memory T cells, or B cells resulting in the prevention of or therapeutic response to the specific disease associated with the antigen(s).

The cationic lipids of the invention may be in the form of cationic lipid complexes. The cationic lipid complex can take the form of various vesicles such as liposomes, micelles, or emulsions. The cationic lipid complexes may be unilaminar or multilaminar. When an antigen is included, the antigen may be encapsulated in the cationic lipid complex or may be unencapsulated. Encapsulated is understood to mean that the antigen may be contained within the internal space of the complex and/or incorporated into the lipid walls of the complex.

The invention further relates to a method for producing these complexes where the method may optionally include the step of purifying these formulations from excess individual components. For the production of the antigen complexes of this invention, inclusion of the purification step is an advantageous embodiment.

In certain embodiments, cationic lipid complexes have a net positive charge and/or a positively charged surface at pH 6.0-8.0.

The optional "antigen" which may be included with cationic lipid complexes of the invention may be nucleic acids, peptides, lipopeptides, proteins, lipoproteins, polysaccharides, and other macromolecules which may be complexed directly with cationic lipids. However, cationic drugs (e.g., large cationic protein) can be directly complexed with an anionic lipid or sequentially complexed first with anionic lipid or polymer followed by cationic lipid. The use of this process permits delivery of positive or neutral charged drugs to cells by the complexes of the present invention.

One aspect of the present invention involves the use of the cationic lipid complexes to stimulate the production of chemokines and cytokines. Chemokines and cytokines are important regulators of immune responses. Chemokines were originally identified as potent chemoattractants for inflammatory cells including neutrophils, eosinophils, and monocytes/macrophages. Subsequent studies have revealed that chemokines have profound effects on immune reactions by regulating the trafficking of dendritic cells and other lymphocytes into lymphoid organs. Dendritic cells are migratory cells that sample antigens in the tissue, migrate to the draining lymph nodes and mature to stimulate the T cell response. CCL2, a member of the CC chemokines was originally identified as a chemotactic and activating factor for monocytes/macrophages. Subsequent studies showed that it can also affect the function of T cells, natural killer cells, and neutrophils. Further exploration found that CCL2 was the most potent activator of CD8+ cytotoxic T lymphocytes ("CTL") activity, when in the presence of the Th1 cytokines, interleukin-12 ("IL-12") and interferon-γ ("IFN-γ"). This can be explained by a positive bidirectional interaction between CCL2 and IFN-γ systems. An absence of either the cytokine or chemokine may interfere with Th1 polarization and subsequent specific tumor immunity generation. Another CC chemokine, CCL-4, has also been shown to recruit and expand dendritic cells in vivo and potentiate the immunogenicity of plasmid DNA vaccines. Recently, it has been shown that chemokines enhance immunity by guiding naïve CD8+ T cells to sites of CD4+ T cell-dendritic cell interaction and promote memory CD8+ T cell generation. A few examples of chemokines that may be stimulated by the cationic lipid complexes of the present invention are CCL-2, CCL-3, and CCL-4. Examples of cytokines that may be stimulated by the cationic lipid complexes of the present invention are IL-12 and IFN-γ. The inventors contemplate that the cationic lipid complexes of the present invention may stimulate chemokines and cytokines in addition to those disclosed in this specification.

In a further aspect, the cationic lipid complexes of the present invention stimulate an immune response by activating cellular kinase pathways such as, for example, the extracellular-signal-regulated kinase (ERK) pathway (also known as mitogen actived (MAP) kinase pathway), p38 pathway, or phosphatidyl inositol-3 (PI-3) pathway. These pathways, in turn, may regulate the stimulation of the immune response and the production of cytokines and chemokines. These pathways are well known by those having skill in the art.

Cationic lipid complexes of the present invention may regulate T cell activity to stimulate an immune response. There are three classes of T cells: helper T cells, killer T cells and regulatory T cells. These three classes of T cells work together to coordinate the cellular immune response. The cytotoxic T-lymphocytes ("CTL"), also known as killer T cells or CD8+ T-cells, are responsible for attacking cells that express foreign or tumor antigens. Regulatory T cells are believed to be responsible for dampening CTL mediated immunity, although the exact mechanisms underlying this effect of the regulatory T cells is not well understood. It is known that decreasing regulatory T cell activity can result in increased CTL activity leading to a more robust cellular immunity response. As shown in the examples below, the cationic lipid complexes of the present invention at optimal lipid dose compositions may also stimulate a potent immune response by decreasing the population of regulatory T cells.

Lipids

The cationic lipid complexes of the present invention may form liposomes that are optionally mixed with antigen and may contain cationic lipids alone or cationic lipids in combination with neutral lipids. Suitable cationic lipid species include, but are not limited to: 3-β[$^4$N—($^1$N,$^8$-diguanidino spermidine)-carbamoyl]cholesterol (BGSC); 3-β[N,N-diguanidinoethyl-aminoethane)-carbamoyl]cholesterol (BGTC); N,N$^1$N$^2$N$^3$Tetra-methyltetrapalmitylspermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2(sperminecarboxamido)ethyl]-N,N-dimethyl-1-p-ropanaminium trifluorocetate) (DOSPA); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N'-tetramethyl-N,N'-bis(2-hydroxyethyl)-2,3-dioleoyloxy-1,4-butanediammonium iodide) (Tfx-50); N-1-(2,3-dioleoyloxy) propyl-N,N,N-trimethyl ammonium chloride (DOTMA) or other N—(N,N-1-dialkoxy)-alkyl-N,N,N-trisubstituted ammonium surfactants; 1,2 dioleoyl-3-(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DORI (DL-1,2-dioleoyl-3-dimethylaminopropyl-β-hydroxyethylammonium) or DORIE (DL-1,2-O-dioleoyl-3-dimethylaminopropyl-β-hydroxyethylammoniu-m) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES) or the cationic lipids disclosed in U.S. Pat. No. 5,283,185, cholesteryl-3β-carboxyl-amido-ethylenetrimethylammonium iodide, 1-dimethylamino-3-trimethylammonio-DL-2-propyl-cholesteryl carboxylate iodide, cholesteryl-3-O-carboxyamido-ethyleneamine, cholesteryl-3-β-oxysuccinamido-ethylenetrimethylammonium iodide, 1-dimethylamino-3-trimethylammonio-DL-2-propyl-cholesteryl-3-β-oxysuccinate iodide, 2-(2-trimethylammonio)-ethylmethylamino ethyl-cholesteryl-3-β-oxysuccinate iodide, 3-β-N—(N',N'-dimethylaminoethane) carbamoyl cholesterol (DC-chol), and 3-β-N-(polyethyleneimine)-carbamoylcholesterol; O,O'-dimyristyl-N-lysyl aspartate (DMKE); O,O'-dimyristyl-N-lysyl-glutamate (DMKD); 1,2-dimyristyloxypropyl-3-dimethyl-hydroxy ethyl ammonium bromide (DMRIE); 1,2-dilauroyl-sn-glycero-3-ethylphosphocholine (DLEPC); 1,2-dimyristoyl-sn-glycero-3-ethylphosphocholine (DMEPC); 1,2-dioleoyl-sn-glycero-3-ethylphosphocholine (DOEPC); 1,2-dipalmitoyl-sn-glycero-3-ethylphosphocholine (DPEPC); 1,2-distearoyl-sn-glycero-3-ethylphosphocholine (DSEPC); 1,2-dioleoyl-3-trimethylammonium propane (DOTAP); dioleoyl dimethylaminopropane (DODAP); 1,2-palmitoyl-3-trimethylammonium propane (DPTAP); 1,2-distearoyl-3-trimethylammonium propane (DSTAP), 1,2-myristoyl-3-trimethylammonium propane (DMTAP); and sodium dodecyl sulfate (SDS). The present invention contemplates the use of structural variants and derivatives of the cationic lipids disclosed in this application.

Certain aspects of the present invention include non-steroidal cationic lipids having a structure represented by the following formula:

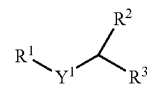

wherein in $R^1$ is a quaternary ammonium group, $Y^1$ is chosen from a hydrocarbon chain, an ester, a ketone, and a peptide, $R^2$ and $R^3$ are independently chosen from a saturated fatty acid, an unsaturated fatty acid, an ester-linked hydrocarbon, phosphor-diesters, and combinations thereof. DOTAP, DMTAP, DSTAP, DPTAP, DPEPC, DSEPC, DMEPC, DLEPC, DOEPC, DMKE, DMKD, DOSPA, DOTMA, are examples of lipids having this general structure.

In one embodiment, cationic lipids of the invention are lipids in which bonds between the lipophilic group and the amino group are stable in aqueous solution. Thus, an attribute of the complexes of the invention is their stability during storage (i.e., their ability to maintain a small diameter and retain biological activity over time following their formation). Such bonds used in the cationic lipids include amide bonds, ester bonds, ether bonds and carbamoyl bonds. Those of skill in the art would readily understand that liposomes containing more than one cationic lipid species may be used to produce the complexes of the present invention. For example, liposomes comprising two cationic lipid species, lysyl-phosphatidylethanolamine and β-alanyl cholesterol ester have been disclosed for certain drug delivery applications [Brunette, E. et al., Nucl. Acids Res., 20:1151 (1992)].

It is to be further understood that in considering cationic liposomes suitable for use in the invention and optionally mixing with antigen, the methods of the invention are not restricted only to the use of the cationic lipids recited above but rather, any lipid composition may be used so long as a cationic liposome is produced and the resulting cationic charge density is sufficient to activate and induce an immune response.

Thus, the complexes of the invention may contain other lipids in addition to the cationic lipids. These lipids include, but are not limited to, lyso lipids of which lysophosphatidylcholine (1-oleoyl lysophosphatidylcholine) is an example, cholesterol, or neutral phospholipids including dioleoyl phosphatidyl ethanolamine (DOPE) or dioleoyl phosphatidylcholine (DOPC) as well as various lipophylic surfactants, containing polyethylene glycol moieties, of which Tween-80 and PEG-PE are examples.

The cationic lipid complexes of the invention may also contain negatively charged lipids as well as cationic lipids so long as the net charge of the complexes formed is positive and/or the surface of the complex is positively charged. Negatively charged lipids of the invention are those comprising at least one lipid species having a net negative charge at or near physiological pH or combinations of these. Suitable negatively charged lipid species include, but are not limited to, CHEMS (cholesteryl hemisuccinate), NGPE (N-glutaryl phosphatidlylethanolanine), phosphatidyl glycerol and phosphatidic acid or a similar phospholipid analog.

Methods for producing the liposomes to be used in the production of the lipid comprising drug delivery complexes of the present invention are known to those of ordinary skill in the art. A review of methodologies of liposome preparation may be found in Liposome Technology (CFC Press New York 1984); Liposomes by Ostro (Marcel Dekker, 1987); Methods Biochem Anal. 33:337-462 (1988) and U.S. Pat. No. 5,283,185. Such methods include freeze-thaw extrusion and sonication. Both unilamellar liposomes (less than about 200 nm in average diameter) and multilamellar liposomes (greater than about 300 nm in average diameter) may be used as starting components to produce the complexes of this invention.

In the cationic liposomes utilized to produce the cationic lipid complexes of this invention, the cationic lipid is present in the liposome at from about 10 mole % to about 100 mole % of total liposomal lipid, or from about 20 mole % to about 80 mole %. The neutral lipid, when included in the liposome, may be present at a concentration of from about 0 mole % to about 90 mole % of the total liposomal lipid, or from about 20 mole % to about 80 mole %, or from 40 mole % to 80 mole %. The negatively charged lipid, when included in the liposome, may be present at a concentration ranging from about 0 mole % to about 49 mole % of the total liposomal lipid, or from about 0 mole % to about 40 mole %. In one embodiment, the liposomes contain a cationic and a neutral lipid, in ratios between about 2:8 to about 6:4. It is further understood that the complexes of the present invention may contain modified lipids, protein, polycations or receptor ligands which function as a targeting factor directing the complex to a particular tissue or cell type. Examples of targeting factors include, but are not limited to, asialoglycoprotein, insulin, low density lipoprotein (LDL), folate and monoclonal and polyclonal antibodies directed against cell surface molecules. Furthermore, to modify the circulatory half-life of the complexes, the positive surface charge can be sterically shielded by incorporating lipophilic surfactants which contain polyethylene glycol moieties.

The cationic lipid complexes may be stored in isotonic sucrose or dextrose solution upon collection from the sucrose gradient or they may be lyophilized and then reconstituted in an isotonic solution prior to use. In one embodiment, the cationic lipid complexes are stored in solution. The stability of the cationic lipid complexes of the present invention is measured by specific assays to determine the physical stability and biological activity of the cationic lipid complexes over time in storage. The physical stability of the cationic lipid complexes is measured by determining the diameter and charge of the cationic lipid complexes by methods known to those of ordinary skill in the art, including for example, electron microscopy, gel filtration chromatography or by means of quasi-elastic light scattering using, for example, a Coulter N4SD particle size analyzer as described in the Examples. The physical stability of the cationic lipid complex is "substantially unchanged" over storage when the diameter of the stored cationic lipid complexes is not increased by more than 100%, or by not more than 50%, or by not more than 30%, over the diameter of the cationic lipid complexes as determined at the time the cationic lipid complexes were purified.

While it is possible for the cationic lipid to be administered in a pure or substantially pure form, it is preferable to present it as a pharmaceutical composition, formulation or preparation. Pharmaceutical formulations using the cationic lipid complexes of the invention may comprise the cationic lipid complexes in a physiologically compatible sterile buffer such as, for example, phosphate buffered saline, isotonic saline or low ionic strength buffer such as acetate or Hepes (an exemplary pH being in the range of about 5.0 to about 8.0). The cationic lipid complexes may be administered as aerosols or as liquid solutions for intratumoral, intraarterial, intravenous, intratracheal, intraperitoneal, subcutaneous, and intramuscular administration.

The formulations of the present invention may incorporate any stabilizer known in the art. Illustrative stabilizers are cholesterol and other sterols that may help rigidify the liposome bilayer and prevent disintegration or destabilization of the bilayer. Also agents such as polyethylene glycol, poly-, and mono-saccharides may be incorporated into the liposome to modify the liposome surface and prevent it from being destabilized due to interaction with blood-components. Other illustrative stabilizers are proteins, saccharides, inorganic acids, or organic acids which may be used either on their own or as admixtures.

A number of pharmaceutical methods may be employed to control, modify, or prolong the duration of immune stimulation. Controlled release preparations may be achieved through the use of polymer complexes such as polyesters, polyamino acids, methylcellulose, polyvinyl, poly(lactic acid), and hydrogels to encapsulate or entrap the cationic lipids and slowly release them. Similar polymers may also be used to adsorb the liposomes. The liposomes may be contained in emulsion formulations in order to alter the release profile of the stimulant. Alternatively, the duration of the stimulant's presence in the blood circulation may be enhanced by coating the surface of the liposome with compounds such as polyethylene glycol or other polymers and other substances such as saccharides which are capable of enhancing the circulation time or half life of liposomes and emulsions.

When oral preparations are required, the cationic lipids may be combined with typical pharmaceutical carriers known in the art such as, for example, sucrose, lactose, methylcellulose, carboxymethyl cellulose, or gum Arabic, among others. The cationic lipids may also be encapsulated in capsules or tablets for systemic delivery.

Administration of the cationic lipid of the present invention may be for either a prophylactic or therapeutic purpose. When provided prophylactically, the cationic lipid is provided in advance of any evidence or symptoms of illness. When provided therapeutically, the cationic lipid is provided at or after the onset of disease. The therapeutic administration of the immune-stimulant serves to attenuate or cure the disease. For both purposes, the cationic lipid may be administered with an additional therapeutic agent(s) or antigen(s). When the cationic lipids are administered with an additional therapeutic agent or antigen, the prophylactic or therapeutic effect may be generated against a specific disease.

The formulations of the present invention, both for veterinary and for human use, comprise a cationic lipid alone as described above, and also optionally, with one or more therapeutic ingredients such as an antigen(s) or drug molecule(s). The formulations may conveniently be presented in unit dosage form and may be prepared by any method known in the pharmaceutical art.

Antigens

In one embodiment, the cationic lipid is administered without any additional agents in order to boost or lower various immune responses, including production of other immune modulators, and to boost the immune response to fighting disease. In another embodiment, the cationic lipid is administered in combination with an antigen or antigens. In this case the objective is to generate an immune response, which is specific to the antigen(s) delivered in combination with the cationic lipid. The response generated may include production of specific cytotoxic T-cells, memory T-cells, or B-cells resulting in the prevention of or therapeutic response to the specific disease associated with those antigen(s). The antigen can be any tumor-associated antigen or microbial antigen or any other antigen known to one skilled in the art.

A "tumor-associated antigen," as used herein is a molecule or compound (e.g., a protein, peptide, polypeptide, lipoprotein, lipopeptide, glycoprotein, glycopeptides, lipid, glycolipid, carbohydrate, RNA, and/or DNA) associated with a tumor or cancer cell and which is capable of provoking an immune response (humoral and/or cellular) when expressed on the surface of an antigen presenting cell in the context of an MHC molecule. Tumor-associated antigens include self antigens, as well as other antigens that may not be specifically associated with a cancer, but nonetheless enhance an immune response to and/or reduce the growth of a tumor or cancer cell when administered to an animal. More specific embodiments are provided herein.

A "microbial antigen," as used herein, is an antigen of a microorganism and includes, but is not limited to, infectious virus, infectious bacteria, infectious parasites and infectious fungi. Microbial antigens may be intact microorganisms, and natural isolates, fragments, or derivatives thereof, synthetic compounds which are identical to or similar to naturally-occurring microbial antigens and, preferably, induce an immune response specific for the corresponding microorganism (from which the naturally-occurring microbial antigen originated). In a preferred embodiment, a compound is similar to a naturally-occurring microorganism antigen if it induces an immune response (humoral and/or cellular) similar to a naturally-occurring microorganism antigen. Compounds or antigens that are similar to a naturally-occurring microorganism antigen are well known to those of ordinary skill in the art such as, for example, a protein, peptide, polypeptide, lipoprotein, lipopeptide, glycoprotein, glycopeptides, lipid, glycolipid, carbohydrate, RNA, and/or DNA. Another non-limiting example of a compound that is similar to a naturally-occurring microorganism antigen is a peptide mimic of a polysaccharide antigen. More specific embodiments are provided herein.

The term "antigen" is further intended to encompass peptide or protein analogs of known or wild-type antigens such as those described in this specification. The analogs may be more soluble or more stable than wild type antigen, and may also contain mutations or modifications rendering the antigen more immunologically active. Antigen can be modified in any manner, such as adding lipid or sugar moieties, mutating peptide or protein amino acid sequences, mutating the DNA or RNA sequence, or any other modification known to one skilled in the art. Antigens can be modified using standard methods known by one skilled in the art.

Also useful in the compositions and methods of the present invention are peptides or proteins which have amino acid sequences homologous with a desired antigen's amino acid sequence, where the homologous antigen induces an immune response to the respective tumor, microorganism or infected cell.

In one embodiment, the antigen in the cationic lipid complex comprises an antigen associated with a tumor or cancer, i.e., a tumor-associated antigen, to make a vaccine to prevent or treat a tumor. As such, in one embodiment, the tumor or cancer vaccines of the present invention further comprise at least one epitope of at least one tumor-associated antigen. In another preferred embodiment, the tumor or cancer vaccines of the present invention further comprise a plurality of epitopes from one or more tumor-associated antigens. The tumor-associated antigens finding use in the cationic lipid complexes and methods of the present invention can be inherently immunogenic, or non-immunogenic, or slightly immunogenic. As demonstrated herein, even tumor-associated self antigens may be advantageously employed in the subject vaccines for therapeutic effect, since the subject compositions are capable of breaking immune tolerance against such antigens. Exemplary antigens include, but are not limited to, synthetic, recombinant, foreign, or homologous antigens, and antigenic materials may include but are not limited to proteins, peptides, polypeptides, lipoproteins, lipopeptides, lipids, glycolipids, carbohydrates, RNA and DNA. Examples of such vaccines include, but are not limited to the treatment or prevention of breast cancer, head and neck cancer, melanoma, cervical cancer, lung cancer, prostate cancer gut carcinoma, or any other cancer known in the art succeptable to immunotherapy, using a cationic lipid in a complex with a tumor-associated antigen(s). It is also possible to formulate the antigen with the cationic lipid without encapsulating in the liposome.

The cationic lipid complexes of the present invention may be used in methods to treat or prevent cancer. In such a case, the mammal to be immunized is injected with the pharmaceutical formulation containing the liposome with the encapsulated antigen(s). Examples of cancers that may be treated with the tumor vaccines include but are not limited to the prevention or treatment of breast cancer, head and neck cancer, melanoma, cervical cancer, lung cancer, prostate cancer, gut carcinoma, or any other cancer known in the art using a cationic lipid and an antigen or multiple peptide antigens associated with the cancer. It is also possible to formulate the antigen with the cationic lipid without encapsulating the antigen in the liposome.

Tumor-associated antigens suitable for use in the present invention include both naturally occurring and modified molecules which may be indicative of single tumor type, shared among several types of tumors, and/or exclusively expressed or overexpressed in tumor cells in comparison with normal cells. In addition to proteins, glycoproteins, lipoproteins, peptides, and lipopeptides, tumor-specific patterns of expression of carbohydrates, gangliosides, glycolipids, and mucins have also been documented. Exemplary tumor-associated antigens for use in cancer vaccines include protein products of oncogenes, tumor suppressor genes, and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins, and a number of other self proteins.

Specific embodiments of tumor-associated antigens include, e.g., mutated or modified antigens such as the protein products of the Ras p21 protooncogenes, tumor suppressor p53 and HER-2/neu and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Tumor-associated antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells, and thus the subject therapy may find advantageous use in conjunction with conventional chemotherapy and/or radiation therapy.

In one embodiment, the human papillomavirus HPV antigens are used. A specific HPV antigen that used as a tumor-associated antigen is HPV subtype 16 E7. HPV E7 antigen-cationic lipid complexes are effective at preventing and treating cervical cancer. In addition, a genetically engineered E7 protein, i.e., E7m protein, having antigenic activity, but without tumorigenic activity, is an effective tumor-associated antigen. E7m-cationic lipid complexes induce cellular immunity to cause complete regression of established tumors and, thus, are useful as potent anti-cervical cancer vaccines.

Tumor-associated antigens can be prepared by methods well known in the art. For example, these antigens can be prepared from cancer cells either by preparing crude extracts of cancer cells (e.g., as described in Cohen et al., Cancer Res., 54:1055 (1994)), by partially purifying the antigens, by recombinant technology, or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Antigens derived from pathogens known to predispose to certain cancers may also be advantageously included in the cancer vaccines of the present invention. It is estimated that close to 16% of the worldwide incidence of cancer can be attributed to infectious pathogens; and a number of common malignancies are characterized by the expression of specific viral gene products. Thus, the inclusion of one or more antigens from pathogens implicated in causing cancer may help broaden the host immune response and enhance the prophylactic or therapeutic effect of the cancer vaccine. Pathogens of particular interest for use in the cancer vaccines provided herein include the, hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLVL (adult T cell leukemia), oncogenic human papilloma viruses types 16, 18, 33, 45 (adult cervical cancer), and the bacterium *Helicobacter pylori* (B cell gastric lymphoma). Other medically relevant microorganisms that may serve as antigens in mammals and more particularly humans are described extensively in the literature, e.g., C. G. A Thomas, Medical Microbiology, Bailliere Tindall, Great Britain 1983, the entire contents of which is hereby incorporated by reference.

In another embodiment, the antigen in the cationic lipid complex comprises an antigen derived from or associated with a pathogen, i.e., a microbial antigen. As such, in one embodiment, the pathogen vaccines of the present invention further comprise at least one epitope of at least one microbial antigen. Pathogens that may be targeted by the subject vaccines include, but are not limited to, viruses, bacteria, parasites and fungi. In another embodiment, the pathogen vaccines of the present invention further comprise a plurality of epitopes from one or more microbial antigens.

The microbial antigens finding use in the cationic lipid complexes and methods may be inherently immunogenic, or non-immunogenic, or slightly immunogenic. Exemplary antigens include, but are not limited to, synthetic, recombinant, foreign, or homologous antigens, and antigenic materials may include but are not limited to proteins, peptides, polypeptides, lipoproteins, lipopeptides, lipids, glycolipids, carbohydrates, RNA, and DNA.

Exemplary viral pathogens include, but are not limited to, viruses that infect mammals, and more particularly humans. Examples of virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Also, gram negative and gram positive bacteria may be targeted by the subject compositions and methods in vertebrate animals. Such gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris*, *Borella burgdorferi*, *Legionella pneumophiliaii*, *Mycobacteria* sps (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*, pathogenic *Campylobacter* sp., *Enterococcus* sp., *Haemophilus infuenzae*, *Bacillus antracis*, *corynebacterium diphtheriae*, *corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatumii*, *Streptobacillus moniliformis*, *Treponema pallidium*, *Treponema pertenue*, *Leptospira*, *Rickettsia*, and *Actinomyces israelli*.

Polypeptides of bacterial pathogens which may find use as sources of microbial antigens in the subject compositions include but are not limited to an iron-regulated outer membrane protein, ("IROMP"), an outer membrane protein ("OMP"), and an A-protein of *Aeromonis salmonicida* which causes furunculosis, p57 protein of *Renibacterium salmoninarum* which causes bacterial kidney disease ("BKD"), major surface associated antigen ("msa"), a surface expressed cytotoxin ("mpr"), a surface expressed hemolysin ("ish"), and a flagellar antigen of Yersiniosis; an extracellular protein ("ECP"), an iron-regulated outer membrane protein ("IROMP"), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of *Ichthyophthirius*; and a structural and regulatory protein of *Cytophaga columnari*; and a structural and regulatory protein of *Rickettsia*. Such antigens can be isolated or prepared recombinantly or by any other means known in the art.

Examples of pathogens further include, but are not limited to, fungi that infect mammals, and more particularly humans. Examples of fungi include, but are not limited to: *Cryptococcus neoformansi*, *Histoplasma capsulatum*, *Coccidioides immitis*, *Blastomyces dermatitidis*, *Chlamydia trachomatis*, *Candida albicans*. Examples of infectious parasites include *Plasmodium* such as *Plasmodium falciparum*, *Plasmodium malariae*, *Plasmodium ovale*, and *Plasmodium vivax*. Other infectious organisms (i.e. protists) include *Toxoplasma gondii*. Polypeptides of a parasitic pathogen include but are not limited to the surface antigens of *Ichthyophthirius*.

Other medically relevant microorganisms that serve as antigens in mammals and more particularly humans are described extensively in the literature, e.g., see C. G. A Thomas, Medical Microbiology, Bailliere Tindall, Great Britain 1983, the entire contents of which is hereby incorporated by reference. In addition to the treatment of infectious human diseases and human pathogens, the compositions and methods of the present invention are useful for treating infections of nonhuman mammals. Many vaccines for the treatment of non-human mammals are disclosed in Bennett, K. Compendium of Veterinary Products, 3rd ed. North American Compendiums, Inc., 1995; see also WO 02/069369, the disclosure of which is expressly incorporated by reference herein.

Exemplary non-human pathogens include, but are not limited to, mouse mammary tumor virus ("MMTV"), Rous sarcoma virus ("RSV"), avian leukemia virus ("ALV"), avian myeloblastosis virus ("AMV"), murine leukemia virus ("MLV"), feline leukemia virus ("FeLV"), murine sarcoma virus ("MSV"), gibbon ape leukemia virus ("GALV"), spleen necrosis virus ("SNV"), reticuloendotheliosis virus ("RSV"), simian sarcoma virus ("SSV"), Mason-Pfizer monkey virus ("MPMV"), simian retrovirus type 1 ("SRV-1"), lentiviruses such as HIV-1, HIV-2, SIV, Visna virus, feline immunodeficiency virus ("FIV"), and equine infectious anemia virus ("EIAV"), T-cell leukemia viruses such as HTLV-1, HTLV-II, simian T-cell leukemia virus ("STLV"), and bovine leukemia virus ("BLV"), and foamy viruses such as human foamy virus ("HFV"), simian foamy virus ("SFV") and bovine foamy virus ("BFV").

In some embodiments, "treatment," "treat," and "treating," as used herein with reference to infectious pathogens, refer to a prophylactic treatment which increases the resistance of a subject to infection with a pathogen or decreases the likelihood that the subject will become infected with the pathogen; and/or treatment after the subject has become infected in order to fight the infection, e.g., reduce or eliminate the infection or prevent it from becoming worse.

Microbial antigens can be prepared by methods well known in the art. For example, these antigens can be prepared directly from viral and bacterial cells either by preparing crude extracts, by partially purifying the antigens, or alternatively by recombinant technology or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

In order to improve incorporation of the antigen into the cationic lipid vesicles and also to improve delivery to the cells of the immune system, the antigen may be modified to increase its hydrophobicity or the negative charge on the antigen. Hydrophobicity of an antigen may be increased such as, for example, by conjugating to a lipid chain or hydrophobic amino acids in order to improve it's the antigen's solubility in the hydrophobic acyl chains of the cationic lipid, while maintaining the antigenic properties of the molecule. The modified antigen can be a lipoprotein, a lipopeptide, a protein or peptide modified with an amino acid sequence having increased hydrophobicity, and combinations thereof. The modified antigen may have a linker conjugated between the lipid and the antigen such as, for example, an N-terminal α or ε-palmitoyl lysine may be connected to antigen via a dipeptide serine-serine linker. As discussed in greater detail below, the DOTAP/E7-lipopeptide complex exhibited an enhanced functional antigen-specific CD8+ T lymphocyte response in vivo compared to the DOTAP/E7 formulation. Further, the antigen may be manipulated to increase its negative charge by altering the formulation buffer in which the antigen is encapsulated into the cationic lipid complexes or by covalently attaching anionic moieties such as, for example, anionic amino acids to the antigen.

As demonstrated in Example 1 (below) immunogenicity of the E7 antigen was increased by covalently modifying the antigen. It was possible to covalently attach to the antigen an amino acid sequence such that the resulting antigen amino acid sequence is not found in the parent protein from which the antigen was derived. Studies were performed to demonstrate that the modified antigen provided superior MHC class I binding affinity compared to the native antigen. This superior binding affinity as demonstrated, translated to the generation of a superior in-vivo anti tumor immune response against HPV-positive TC-1 tumors. The present invention will be further appreciated in light of the following examples.

EXAMPLES

Example 1

Effective Stimulation of the Immune System and Antigen-Delivery to the Antigen Presenting Cells by Specific Dose Compositions of Cationic Lipids Leads to a Potent Immune Response in the Prevention and Treatment of Disease 1. Preparation of Liposomes for Use as an Immune System Stimulant Including Cationic Lipid (for Example, DOTAP) Alone, or Cationic Liposomes Incorporating an Antigen (for Example, HPV Protein E7 Peptide Antigen).

Cell culture grade water (commercially available from Cambrex of Walkersville, Md.) or phosphate buffered saline was used in all liposome preparation procedures. The E7 antigen was the H-2D$^b$ restricted CTL epitope (amino acid 49-57, RAHYNIVTF [SEQ. ID. NO. 1]) derived from HPV 16 E7 protein (synthesized by the University of Pittsburgh, Molecular Medicine Institute, Pittsburgh, Pa.).

Liposomes used these studies were made using lipid films. Lipid films were made in glass vials by (1) dissolving the lipids in chloroform, and (2) evaporating the chloroform solution under a steady stream of dry nitrogen gas. Traces of organic solvent were removed by keeping the films under vacuum overnight. The lipid films were then hydrated for 12 h by adding the required amount of water or buffer to make a final concentration of 10 mg/mL. The suspensions were then sonicated in a bath type sonicator for 10 min followed by extrusion through 400, 200 and 100 nm membrane filters (commercially available from Hamilton Co., Reno, Nev.) and stored at 4° C. For the preparation of DOTAP/E7, the lipid film was rehydrated by an aqueous solution of E7 peptide. Other methods used in general liposome preparation that are well known to those skilled in the art may also be used.

2. IL-12 and TNF-α Production by Lymph Node Cells and Dendritic Cells is Stimulated after Treatment with Cationic Lipids In order to elucidate the immunostimulatory mechanism of the cationic lipid DOTAP and to further characterize its immuno-stimulatory activity it is important to assess whether DOTAP can induce proper Th1 cytokine production to further enhance the immune response. Thus, we examined cytokine production by bone marrow derived dendritic cells ("BMDC") following DOTAP stimulation. After six days culture in vitro in the presence of recombinant mGM-CSF and mIL-4, BMDC ($10^6$ cells in 2 mL per well) were stimulated with medium control, DOTAP liposomes, LPD (cationic lipid complexed DNA and protamine) or lipopolysaccharide (LPS) at 0.1 μg/mL for 20 h at 37° C. IL-12 and TNF-α production in supernatant were analyzed by BD ELISA Set. LPD and LPS were used as positive controls. The bacterial DNA in LPD contains CpG motifs known to activate the immune system via toll-like-receptors and stimulate TNF-α. Culture supernatant was harvested and IL-12 and TNF-α cytokine levels were assessed by ELISA. In FIG. 1, IL-12, but not TNF-α, production increased in response to DOTAP concentration. This indicates that, in addition to dendritic cells, other cell types, e.g. T cells, may also be involved in the Th1 cytokine production stimulated by DOTAP liposome observed in vivo. Further, the fact that the cationic lipids did not induce significant levels of the pro-inflammatory cytokine TNF-α, suggests that the immunostimulatory mechanism may be independent of the toll-like-receptor pathway.

3. An Antigen Specific CTL Immune Response is Induced in a Lipid Dose Dependent Manner by a Cationic Lipid/Antigen Complex.

C57BL/6 female mice were immunized with DOTAP/E7 formulations at days 0 and 7. Various concentrations of DOTAP were used, however the concentration of the HPV-16 E7 antigen was maintained at a 10 μg dose. The E7 antigen was the H-2 D$^b$ restricted CTL epitope (amino acid 49-57, RAHYNIVTF (SEQ. ID. NO. 1) derived from HPV 16 E7 protein. Seven days after the last immunization, mice were sacrificed and splenocytes were harvested and dissociated. After removal of RBC, total splenocyte population (responder cells) was stimulated for 5 days with E7 peptide (10 μg/mL) in the presence of 40 U/mL recombinant IL-2 (commercially available from R&D systems of Minneapolis, Minn.) in complete RPMI-1640 medium. After in vitro CTL expansion, responder cells were ready to be used as CTL effectors. TC-1 cell line was used as target cells in this assay. TC-1 cells are C57BL/6 mouse lung epithelial cells transformed with HPV 16 E6 and E7 oncogenes and the activated H-ras. To discriminate between effectors and target, TC-1 cells were labeled with PKH-67 (commercially available from Sigmaof St. Louis, Mo.) according to manufacturer's instructions. Effectors and labeled targets were plated into 96-well plates at various effector:target (E:T) ratios and the lysis reactions were carried out for 4 h at 37° C. Cells were then harvested and stained with propidium iodide (PI) for analysis on a BD FACSCanto digital flow cytometer (commercially available from BD Biosciences of San Diego, Calif.). Percentage of E7-specific lysis was determined by the percentage of PI positive cells within the FL1 (PKH-67) positive region.

Figure 2:
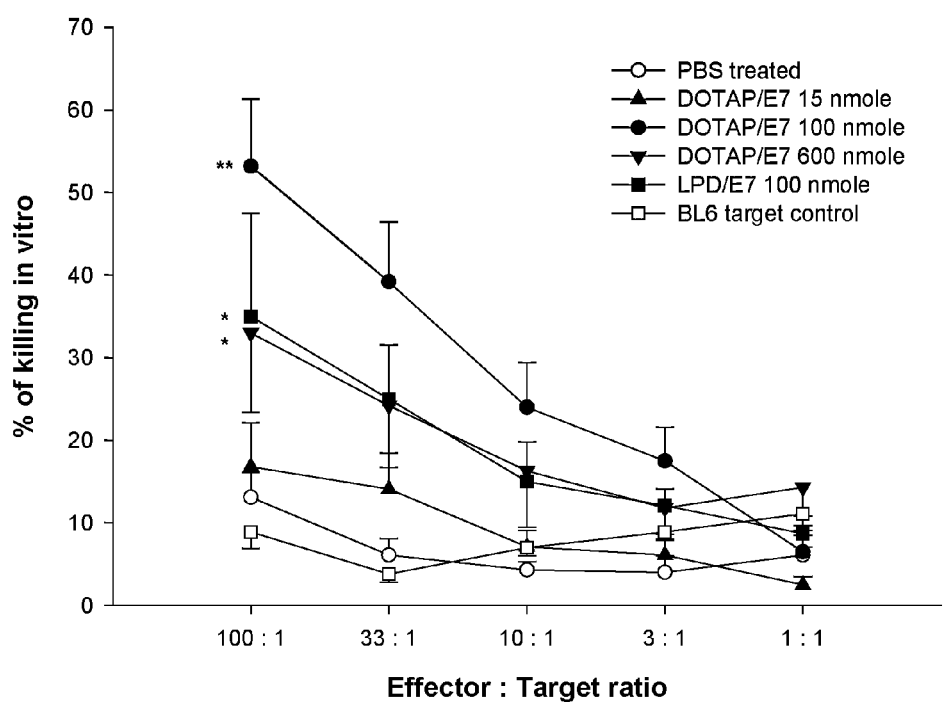
FIG. 2 Analysis of CTL-mediated cytotoxicity by flow cytometry. E7-specific cytotoxic T-lymphocyte ("CTL") clones were prepared and expanded. After five days in vitro restimulation with E7 peptide, effector cells were incubated with PKH-67 labeled TC-1 target cells at the indicated effector:target ratio for 4 h at 37° C. BL-6 was used as a non-specific target cell control. Percentage of E7-specific killing was determined by the percentage of PI positive cells within the gating of PKH-67 positive target cells in flow cytometry. Statistical analysis was calculated by comparing with control group at 100:1 E:T ratio (*$p<0.01$, **$p<0.001$, n=5).

Turning now to FIG. 2, it is observed that mice that received the DOTAP/E7 at 100 nmoles of DOTAP exhibited significant CTL activity resulting in specific killing of TC-1 cells while mice that received DOTAP/E7 at 600 nmoles of DOTAP showed a significantly reduced killing effect indicating a cationic lipid dose response effect. Mice that received DOTAP/E7 at 15 nmoles of DOTAP did not result in CTL activity that was significantly different from control mice treated with PBS. We confirmed this killing was E7-specific by incubating effector cells from groups that received the optimal dose of DOTAP with HPV E7-negative BL6 cells as targets, and negligible cell killing resulted. In addition to CTL mediated killing, we also investigated natural killer ("NK")

cell mediated cytotoxicity. NK cells are able to destroy tumor cells without deliberate immunization or activation and they also play an important role in innate immune responses [Wu, J and Lanier, L L, *Natural killer cells and cancer*. Adv Cancer Res 90:127 (2003); and Lodoen, M B, and Lanier, L L, *Natural killer cells as an initial defense against pathogens*. Curr Opin Immunol 18:391 (2006)]. Mice that received DOTAP/E7 complex, at various doses of DOTAP exhibited significant killing against YAC-1 cells, an NK susceptible target.

Figure 3:
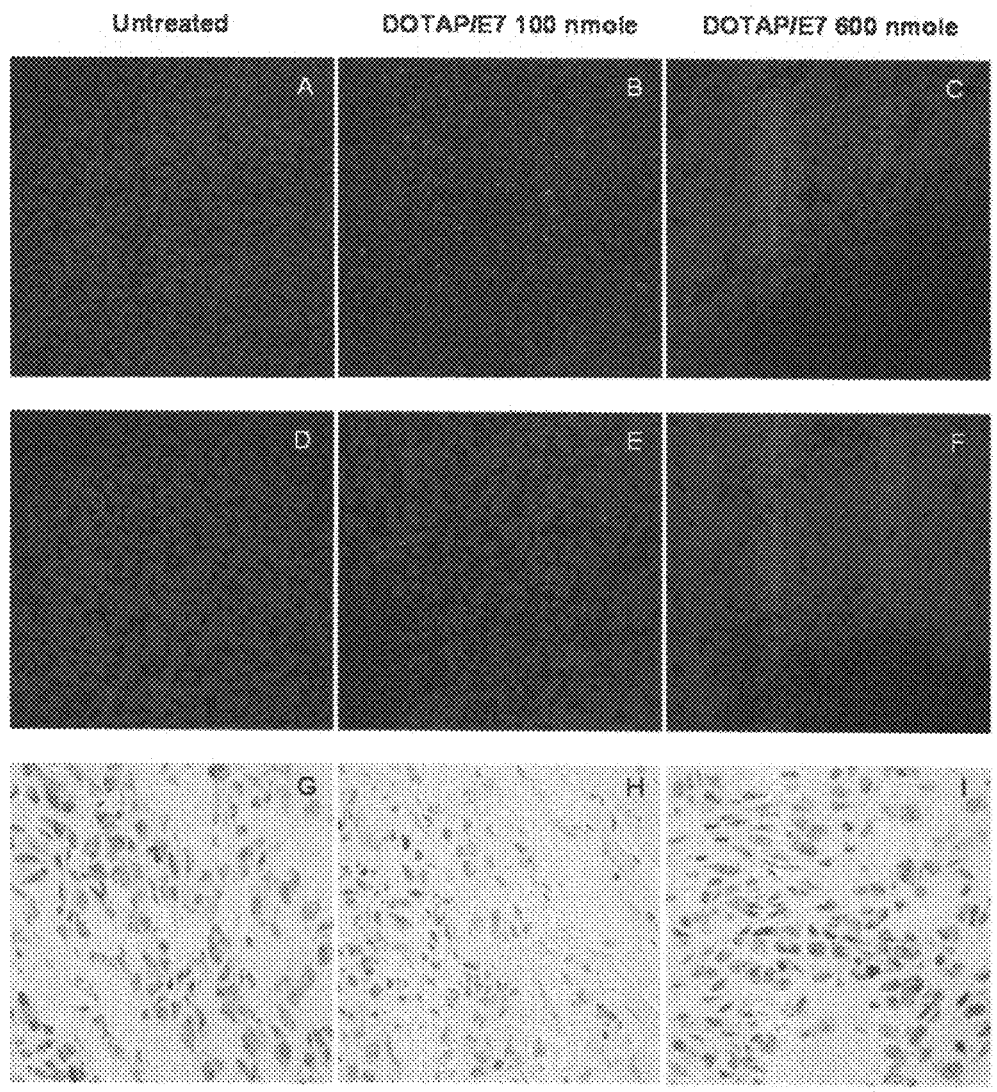
FIG. 3 Tumor infiltrating T-lymphocytes were observed in mice that received DOTAP/E7 at the optimal lipid dose. TC-1 tumors were established as described and were left untreated or treated with a single injection on day 6. Solid tumors were dissected on day 14 and examined for infiltrating lymphocytes. FITC conjugated anti-CD8 (A, B, C) and anti-CD4 (D, E, F) antibodies were used to determine tumor infiltrating T cells followed by counterstaining with DAPI. Representative tumor sections from groups of 3 mice were examined as described and imaged with confocal microscopy. TUNEL assay was conducted to detect apoptosis in the tumor sections (G, H, I).

4. Administration of a Cationic Lipid/Antigen Complex Induces In Vivo CD8+ and CD4+ T-Cell Production in a Lipid Dose Dependent Manner and Migration into the Microenvironment of E-7 Positive Tumors In order to understand whether the optimal DOTAP/E7 formulation induces the production of T-lymphocytes (T-cells) and if the T-lymphocyes would migrate effectively to the site of cells expressing the E7 antigen, immunohistochemical examination of tumor-infiltrating T lymphocytes was performed (FIG. 3). C57BL/6 female mice 6-7 weeks old were purchased from Charles River Laboratories (Wilmington, Mass.) and were used in all animal studies. Subcutaneous HPV-positive tumors were established by injecting TC-1 cells ($10^5$ cells) into the hair-trimmed flank of the mouse on day 0. On day 6, mice (n=6-12) were subcutaneously injected with 150 μL of selected formulations of DOTAP/E7 (15, 100, 600 nmole), each containing 10 μg of the E7 peptide.

Solid HPV-positive tumors were excised from the mice and dissected on day 14 and embedded in Tissue-Tek® OCT compound (commercially available from Sakura Finetek of Torrance, Calif.) (followed by cryosection preparation). Samples were cut into 8 μm thick sections by a cryostat (commercially available from H/I Hacker Instruments & Industries Inc.). FITC-conjugated anti-CD8 and anti-CD4 antibodies (commercially available from Miltenyi Biotec Inc. of Auburn, Calif.) were used to determine tumor-infiltrating T cells followed by counterstaining nuclei with DAPI. Images of the sections were taken with a Leica SP2 confocal microscope.

TUNEL assays were conducted using a TACS™ TdT Kit (commercially available from R&D Systems of Minneapolis, Minn.) and developed with DAB according to manufacturer's instructions. Samples were imaged with a Nikon Microphot SA microscope.

As shown in FIG. 3, a high proportion of CD8+ T lymphocyte (~5%) were found in mice that received DOTAP/E7 at 100 nmole (FIG. 3B) compared to the untreated mice (FIG. 3A) and those that received high dose DOTAP composition (600 nmole, FIG. 3C). A similar result was found for CD4+ T cells, (FIGS. 3E-F). The TUNEL assay for determining apoptosis was also performed in some tumor cryosections. In FIG. 3H, after mice were treated with the 100 nmol dose of lipid in the DOTAP/E7 complex, a TUNEL-positive reaction was observed in the condensed and fragmented nuclei of the tumor cells of those mice as compared to the untreated mice (FIG. 3G) and high lipid dose group (FIG. 3I), which exhibited normal and vital tumor cells. A similar dose response effect of cationic lipid dose on T-lymphocyte production is observed to the dose response effect on the antigen specific CTL-response described above in section 3 entitled "An antigen specific CTL immune response is induced in a lipid dose dependent manner by a cationic lipid/antigen complex".

5. Administration of a Cationic Lipid/Antigen Complex Induces Humoral Immunity.

Figure 4:
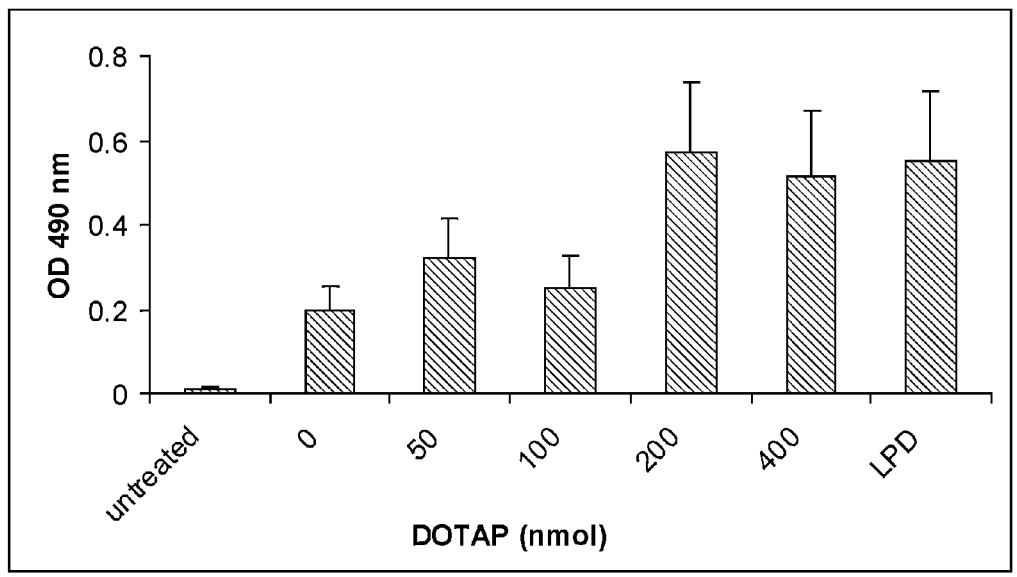
FIG. 4 is a graph depicting induction of humoral activity by treatment with cationic lipid treatment.

FIG. 4 shows the results of injecting mice with a cationic lipid/antigen complex containing DOTAP and the protein antigen, ovalbumin. Mice were evaluated for the ability of the complex to stimulate B-cell activity and to induce antibody production, also known as the humoral immune response. The humoral response was evaluated by monitoring IgG antibody formation. As illustrated by FIG. 4, DOTAP/ovalbumin complexes elicited a humoral response in a dose dependent manner. These data suggest that DOTAP formulations may be used to stimulate both cellular and humoral immune responses.

6. Administration of a Cationic Lipid/Antigen Complex Reduces T-Regulatory Cell Populations in a Lipid Dose Dependent Manner.

Figure 5:
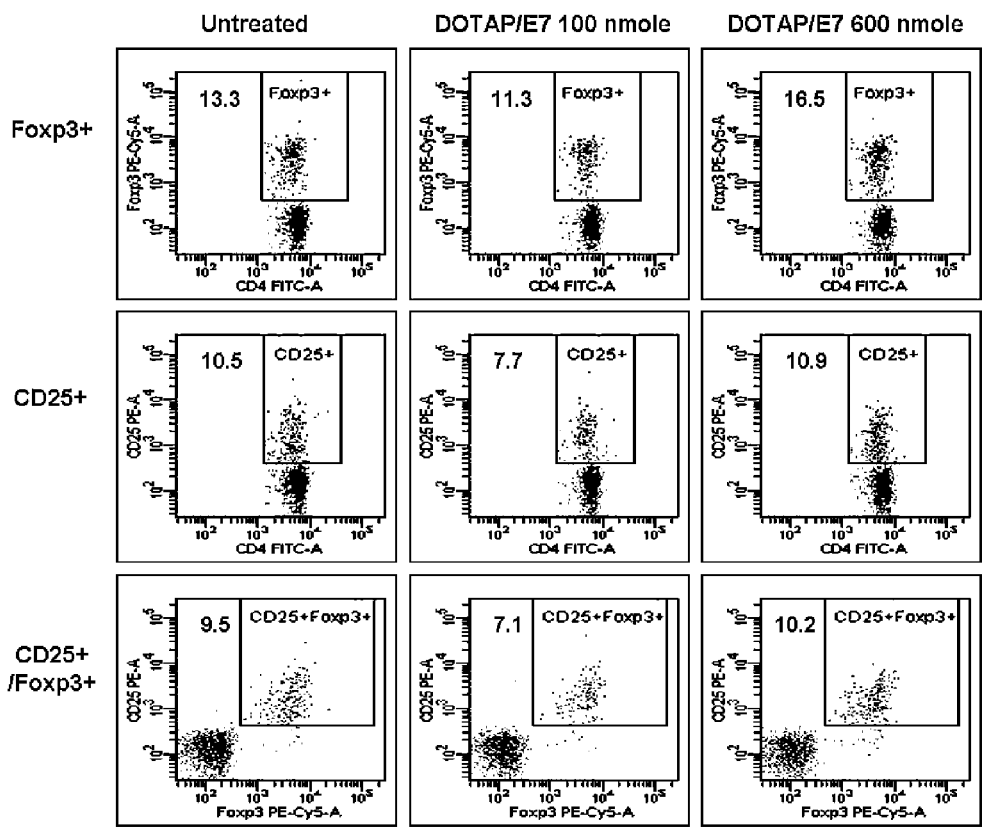
FIG. 5 is a graph illustrating the reduction in the T regulatory cell population in mice after receiving DOTAP with E7 peptide using flow cytometry.

Regulatory T cells are thought to dampen T-cell immunity to tumour-associated antigens and to be the main obstacle tempering successful immunotherapy and active vaccination. Thus, we investigated the ability of DOTAP/E7 in a therapeutic vaccine formulation at its optimal dose to break the immune tolerance maintained by T regulatory cells in tumor-bearing mice, thus enhancing the T-cell immunity to tumor associated antigens. All anti-mouse antibodies used for flow cytometry analysis were purchased from and are commercially available from BD Pharmingen (San Diego, Calif.) or eBioscience, Inc. (San Diego, Calif.). Spleen cells were harvested and dissociated by using 1 mg/ml collagenase and a 70 μm cell strainer. After removal of red blood cells (RBC), single cell suspensions were stained with fluorescent-labeled monoclonal anti-CD4 (RM4-5), anti-CD8a (53-6.7), anti-CD3e (145-2c11), anti-NK1.1 (pk136) and anti-CD25 (pc61.5) antibodies for 30 min at 4° C. After fixation and permeabilization using the Cytofix/Cytoperm™ kit (BD Pharmingen) according to the manufacturer's instruction, cells were stained with anti-Foxp3 (FJK-16s) in 50 μl of Perm/Wash™ buffer for 30 min at 4° C. The cells were washed two more times in Perm/Wash™ buffer and then finally resuspended in 300 pt stain buffer and analyzed on a BD FACSCanto digital flow cytometer (commercially available from BD Biosciences of San Diego, Calif.). As shown in FIG. 5, spleen cells harvested from mice that received DOTAP/E7 complex (100 nmole DOTAP) but not the high dosage (600 nmole DOTAP) animals exhibited lower amounts of T-reg cell subpopulations (Foxp3+, CD25+ and CD25+/Foxp3+) compared to untreated tumor-bearing mice.

In Table 1, ten representative experiments for T-reg analysis are summarized. The population of CD4+ T cells significantly increased in spleen cells after mice received optimal DOTAP/E7 treatment, a similar increase was also found in CD8+ T cells (data not shown). In addition, significant decreases of T-reg populations (CD4+/Foxp3+ and CD4+/CD25+/Foxp3+) were found in this treatment group. It was especially evident that the reduced anti-tumor activity of DOTAP/E7 at high DOTAP dose was associated with increased T-reg cell population. A dose response effect of the cationic lipid is again observed. This result indicates that cationic lipid composition used in the immunotherapy at an optimal dose of lipid is able to possibly enhance the observed immune response to the specific cancer by breaking tolerance in tumor-bearing mice and to stimulate proliferation of functional CD4+ and CD8+ antigen-specific T lymphocytes while suppressing the T-reg cell population.

TABLE 1

Percentage of Treg subpopulation in spleen cells in tumor-bearing mice after the treatment with DOTAP/E7 complex

| | CD4+ | CD4+/Foxp3+ | CD4+/CD25+/Foxp3+ |
|---|---|---|---|
| PBS treated | 18.8 ± 2.9% | 13.1 ± 0.1% | 9.5 ± 0.5% |
| DOTAP/E7 15 nmole | 21.7 ± 1.3% | 12.0 ± 1.0% | 8.4 ± 0.2% |
| DOTAP/E7 100 nmole | 25.1 ± 2.4% | 11.4 ± 0.2% | 7.2 ± 0.2% |
| DOTAP/E7 600 nmole | 22.1 ± 2.1% | 14.3 ± 2.3% | 9.5 ± 0.9% |
| LPD/E7 100 nmole | 26.8 ± 2.2% | 11.0 ± 0.1% | 7.4 ± 0.1% |

\*\*p < 0.01,
\*\*\*p < 0.001 (n = 10 per group)

10. Kinetics of TC-1 HPV-Positive Tumor Growth in Mice Treated with DOTAP/E7 Compositions at Varying Doses of DOTAP.

Figure 6:
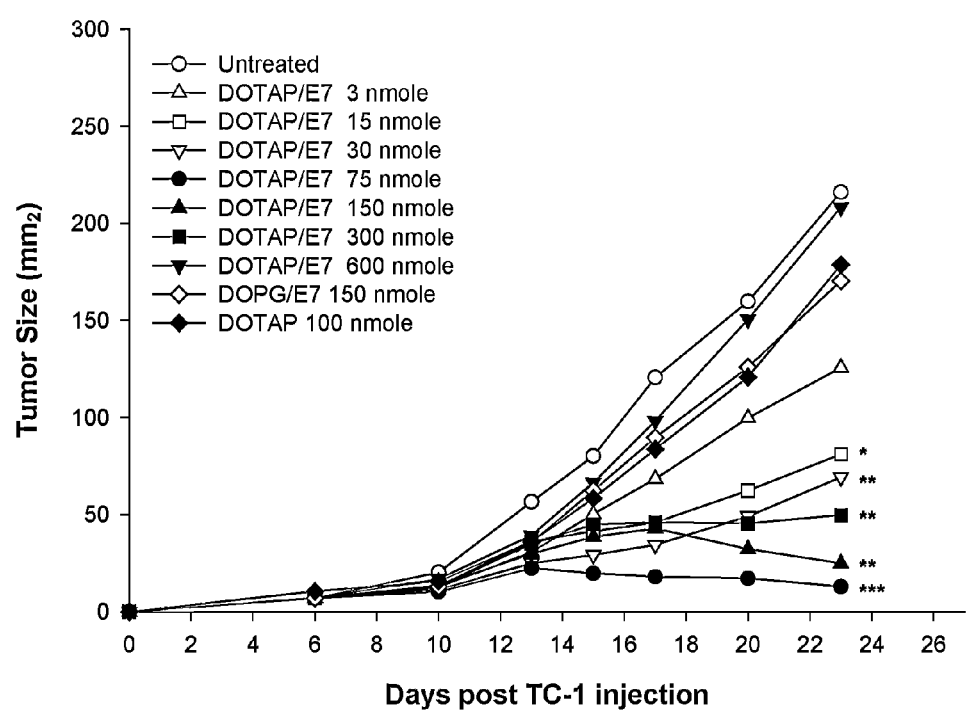
FIG. 6 Kinetics of TC-1 tumor growth in mice treated with DOTAP/E7 formulations. On day 6 post TC-1 inoculation, mice received treatment of 10 μg E7 peptide formulated in DOTAP liposomes at various lipid concentrations. TC-1 tumor size of each group at day 23 was compared to the untreated control group and was analyzed statistically (*$p<0.05$, $p<0.01$, *$p<0.001$).

In FIG. 6, mice were subcutaneously injected with TC-1 cells on day 0 in order to induce the growth of HPV-positive tumors. The mice received DOTAP/E7 compositions containing 10 μg E7 peptide subcutaneously on the opposite side of the abdomen on day 6. DOTAP lipid concentration in the complex varied from 3 to 600 nmole (3, 15, 30, 75, 150, 300, and 600 nmole). Low dose of DOTAP (15 nmole) showed partial tumor inhibition effect (P<0.05) compared to the untreated control on day 23, while DOTAP at 30, 150 or 300 nmol exhibited an enhanced efficacy (P<0.01). DOTAP at 75 nmol showed the most significant tumor regression effect (P<0.001). Again, mice given a high dose of DOTAP (600 nmol) did not show anti-tumor activity, confirming that DOTAP liposomes at a high dose might have induced a negative regulation to the immune response. In addition, DOTAP liposomes at the 100 nmole dose, but without E7 peptide, did not show significant inhibition of tumor growth, indicating that the anti-tumor effect was antigen specific.

11. DOTAP/E7 Complex is Taken Up Mainly by Dendritic Cells after Injection and Induces Dendritic Cell Activation and Migration to the Draining Lymph Node.

Figure 7:
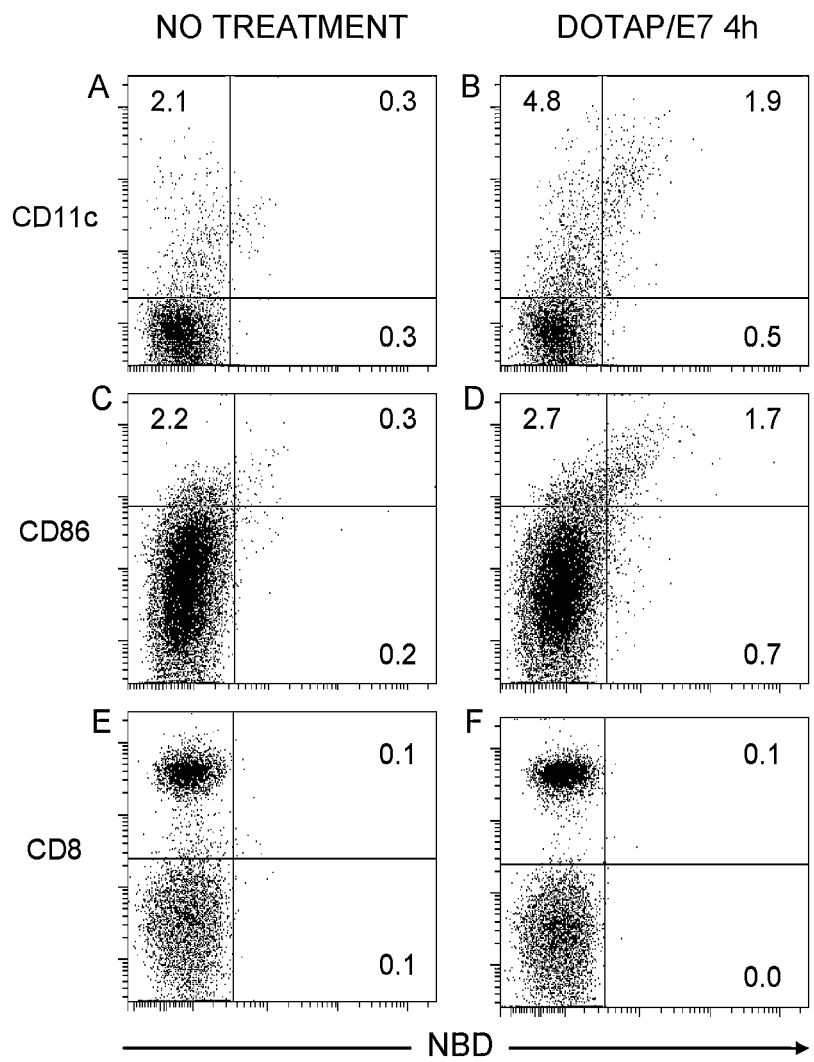
FIG. 7 Subcutaneous injection of DOTAP induces dendritic cell activation and migration to the draining lymph node. Naïve mice (n=4-6) were injected with PBS control (A, C and E) or DOTAP/E7 containing 100 nmols total lipid with 0.5% NBD-DOTAP (B, D and F). At 4 h after the injection, draining lymph node cells were prepared and stained with appropriate antibodies to surface markers. The co-expression of NBD and CD11c (A and B) or CD86 (C and D) were analyzed within total lymph node cells whereas the co-expression of NBD and CD8 (E and F) were gated and analyzed within CD3+ population. The numbers represent the percentages of cells in the quadrants.

Naïve mice (n=4-6) were injected with PBS control (FIGS. 7 A, C and E) or DOTAP/E7 containing 100 nmols total lipid with 0.5% 1-Oleoyl-2-[6-[(7-nitro-2-1,3-benzoxadiazol-4-yl)amino]hexanoyl]-3-trimethylammonium propane] ("NBD-DOTAP") (FIGS. 7 B, D, and F). At 4 h after the injection, draining lymph node cells were prepared and stained with appropriate antibodies to surface markers. The co-expression of NBD and CD11c (FIGS. 7 A and B) or CD86 (FIGS. 7 C and D) were analyzed within total lymph node cells whereas the co-expression of NBD and CD8 (FIGS. 7 E and F) were gated and analyzed within CD3+ population. The numbers represented the percentages of cells in the quadrants. Draining lymph node cells were harvested and analyzed by flow cytometry at different time points post injection. The numbers of CD11c+ cells among total lymph node cells increased by more than 2.5-fold compared to untreated mice 4 h after NBD-DOTAP/E7 injection (FIGS. 7 A and B). The expression of the costimulatory molecule, CD86 on the NBD+ cells was investigated and NBD+ cells demonstrated high levels of CD86 (FIGS. 7 C and D), indicating that suncutaneous injection of DOTAP induced dendritic cell activation. NBD uptake by other cell types such as T lymphocytes was also investigated by costaining with anti-CD3, CD4 and CD8 antibodies. CD3+ cells were gated and analyzed in (FIGS. 7 E and F) and showed no NBD uptake after NBD-DOTAP injection. The results clearly demonstrated that NBD-DOTAP is mainly taken up by dendritic cells (~80%) soon after immunization and DOTAP induces migration of activated dendritic cells to the draining lymph node, resulting in dendritic cell-T cell interactions and eliciting strong T-cell responses.

12. Immunization with DOTAP/E7 Complex Formulated with One Particularly Advantageous Dose DOTAP Elicits Functional CD8+ T Cells.

Figure 8:
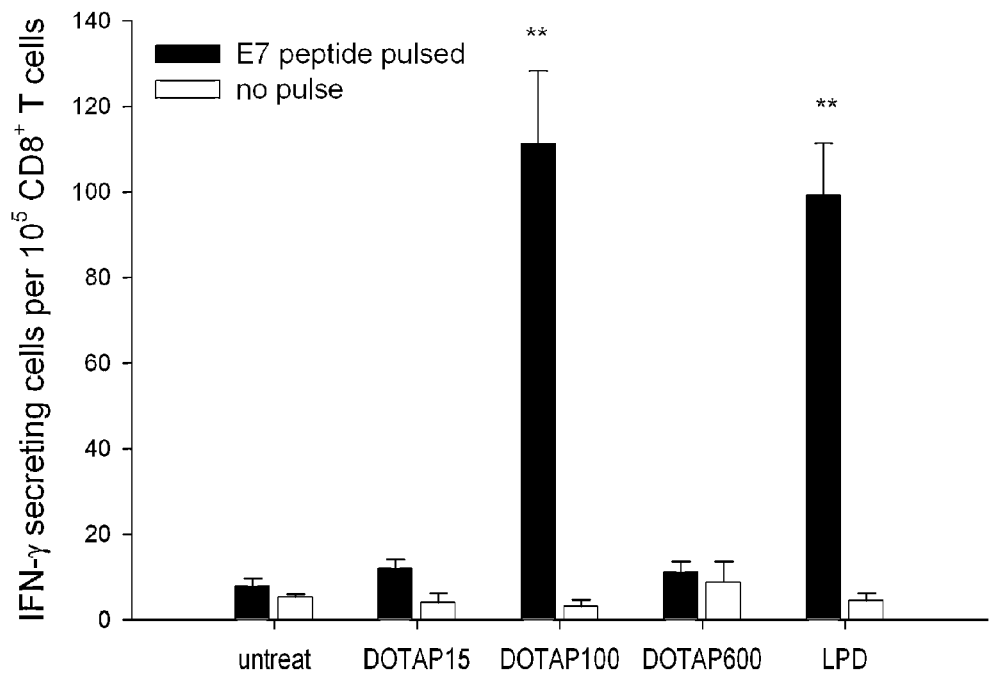
FIG. 8 shows that immunization with E7 peptide formulated in optimal DOTAP adjuvant elicits functional $CD8^+$ T cells. The numbers of $CD8^+$ IFN-$\gamma^+$ cells per $10^5$ $CD8^+$ T cells were shown as mean±SD and were compared to the untreated control (n=4, **$p<0.01$).

IFN-γ secreted by activated T cells or NK cells are known to play important roles in Th1 type immune response as well as inducing CTL response. To assess whether the functional CD8+ T lymphocytes induced by DOTAP/E7 vaccination would be able to produce the essential cytokine, spleen cells from control or immunized mice were isolated at one week after the final immunization and incubated with 5 μg/ml E7 peptide or without peptide for 6 h followed by intracellular staining of IFN-γ. As depicted in FIG. 8, the number of IFN-γ producing CD8+ cells were significantly higher in mice that received E7 formulated at the optimal lipid dose of DOTAP and LPD positive control than the negative control group. IFN-γ production by the CD8+ cells occurred in an E7-specific manner. These results show that DOTAP at optimal dose is a potent vaccine adjuvant for the induction of CTL as well as generation of IFN-γ producing CD8+ T lymphocytes in the systemic lymphoid organs.

13. Comparison of the Anti-Tumor Efficacy of Cationic Lipid/E7 Complexes with the Anti-Tumor Activity of E7 Formulated in Leading Adjuvants Known to Induce Antigen Specific CTL Activity.

Figure 9:
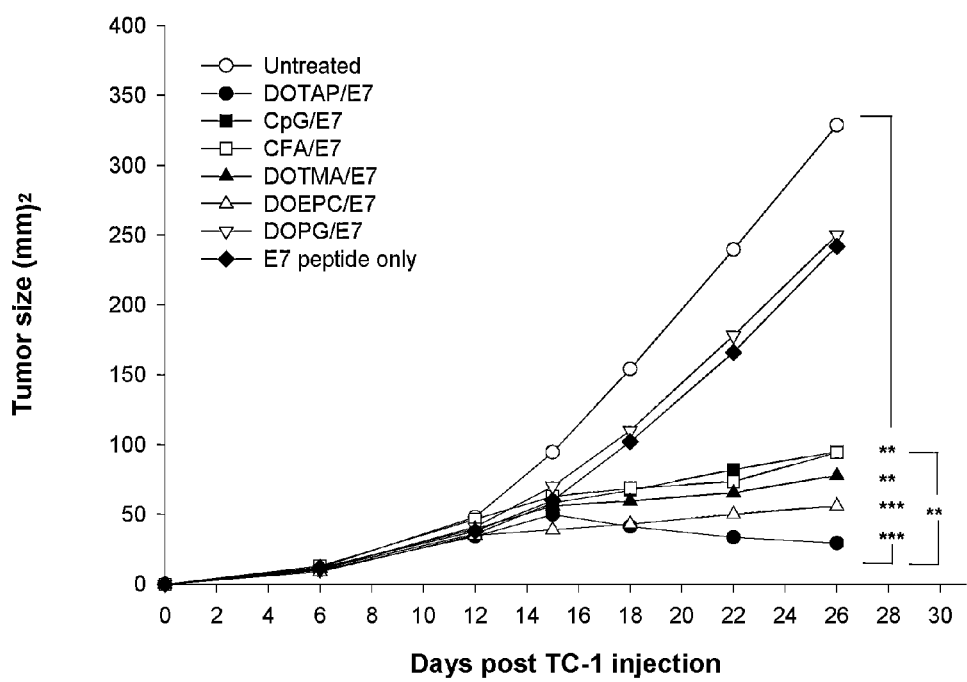
FIG. 9 is a Plot illustrating the anti-tumor immune response of cationic lipid/E7 complexes composed of various cationic lipids compared to potent adjuvants known to elicit a T-cell response

To compare the efficacy of cationic lipid/E7 formulations with other adjuvants to induce an immune response to a tumor, 6-12 tumor-bearing mice per formulation were treated, six days after establishing tumors, with E7 peptide formulated liposomes comprised of (1) cationic lipid (DOTAP, DOEPC and DOTMA), at the 100 nmole dose composition of cationic lipid, (2) anionic lipid (DOPG), or (3) adjuvants (complete Freund adjuvant ("CFA") or CpG ODN1826). In FIG. 9, mice receiving both adjuvants as well as the cationic lipid formulations showed effective inhibition of tumor growth compared to the control group on day 26. Mice that received the anionic lipid DOPG/E7 did not show tumor regression. Mice receiving optimal DOTAP/E7 and DOEPC formulations exhibited a better anti-cancer activity (p<0.01) compared to those receiving CpG/E7 or CFA/E7 formulations. Mice receiving optimal DOTMA/E7 also exhibited a better anti-cancer activity compared to those receiving CpG/E7 or CFA/E7 formulations.

Figure 10A:
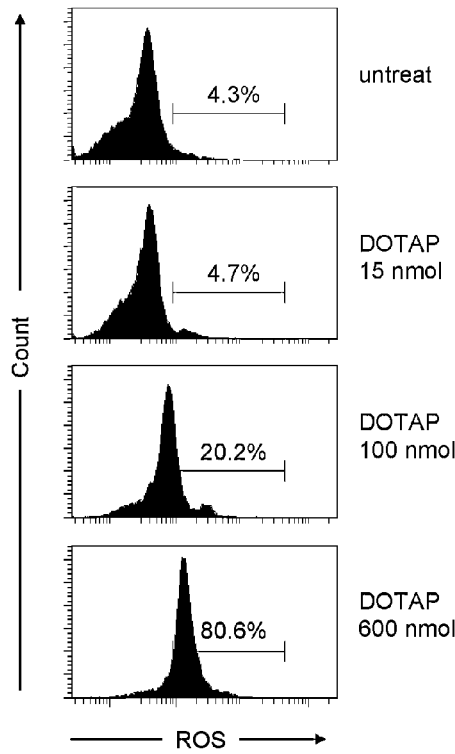
FIG. 10 is a graph illustrating ROS production in the draining lymph node of mice and correlated with the anti-tumor immune response. A Draining lymph nodes ("DLN") from mice that received injections of DOTAP/E7 containing 0, 15, 100 or 600 nmol lipid were isolated 2 h after the injection. The relative percentages of cells with positive ROS signals are listed. B Cytotoxicity in the DLN was measured by collecting cells at 10 h after DOTAP/E7 injection by flow cytometry. The relative percentages of dead cells (PI positive) in DC (open square) and the numbers of live DC per $10^5$ LN cells (bars) were shown and compared with that of the untreated control by paired Student's t test (**P<0.01). C Reactive oxygen species ("ROS") production in DLN was diminished by co-formulation of an inert neutral lipid, dioleoyl phosphatidylcholine ("DOPC") with DOTAP/E7 (mole ratio of DOPC/DOTAP=5), resulting in decreased anti-tumor activity of the complex.
Figure 10B:
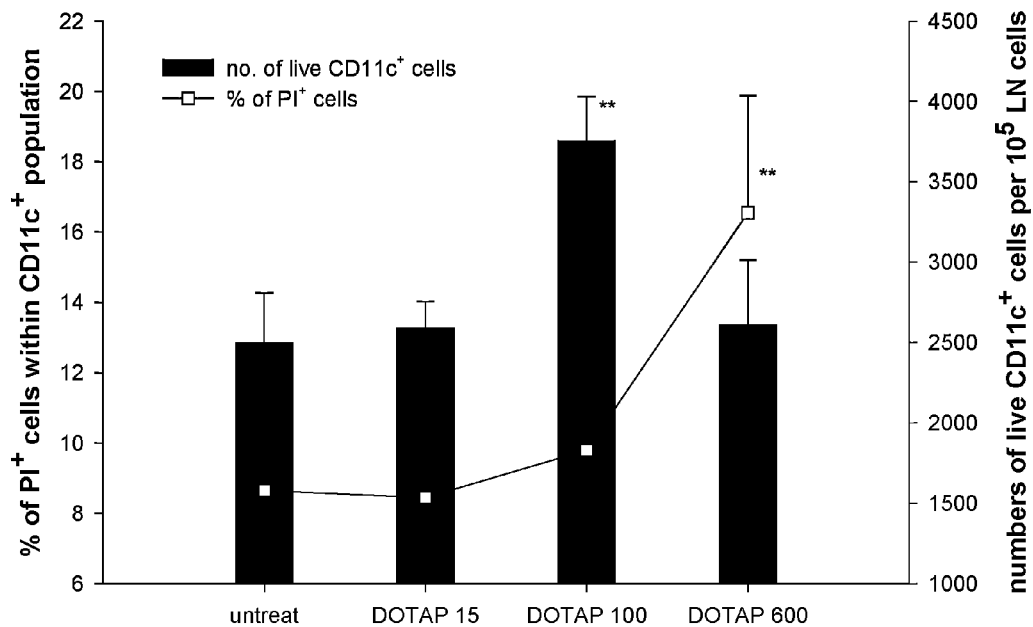

14. Cationic Lipids Induce ROS Production in a Dose Dependent Manner, Resulting in Dendritic Cell Death and Reduced Immunostimulatory Effect at High Doses Draining lymph node from mice (n=4 per condition) received subcutaneous injections of DOTAP/E7 containing 0, 15, 100 or 600 nmols lipid were isolated at 2 h after the injection. Total lymph node cells were incubated with DCFH-DA compound at 37° C. for 30 min prior to flow cytometric analysis. Large granular cells were gated and analyzed for the expression of ROS where the fluorescent product DCF was generated in the presence of ROS. The relative percentages of cells with positive ROS signals are listed in FIG. 10A. Cytotoxicity in the draining lymph node was carried out by collecting cells at 10 h after DOTAP/E7 injection and staining with appropriate antibodies. In FIG. 10B, the relative percentages of dead cells in dendritic cells (DC) are shown in the line plot (□) and the bar chart represents the numbers of live DC per $10^5$ LN cells. The numbers were normalized to the untreated control and analyzed statistically (p<0.01). Cells from mice that received DOTAP 15 nmol exhibited basal level of ROS production (<5%), whereas cells from mice injected with DOTAP 100 nmole dose produced relatively higher levels of ROS (~20%). Strikingly, a majority of large granular cells (~80%) from DOTAP 600 nmol group showed positive ROS signal. At 10 h post subcutaneous injection, total lymph node cells were harvested and analyzed for cell death by flow cytometry (FIG. 10B). Percentage of cell death (propidium iodide positive) within the CD $11c^+$ (dendritic cell) population increased with lipid dose and correlated positively with the ROS production shown in FIG. 10A. Percentage of cell death in DC population was about twice as high for the group injected with DOTAP high dose compared to the group of untreated control. Also shown in FIG. 10B are the numbers of live CD11c$^+$ cells per $10^5$ lymph node cells as a function of the dose of DOTAP lipid. Mice receiving DOTAP/E7 with lipid at 100 nmol exhibited the highest amount (p<0.01) of live dendritic cells among other treatment groups. The draining lymph node weighed more 2 days after mice received the optimal formulation. Collectively, the results indicate that ROS production induced by high dose DOTAP may cause dendritic cell death.

Figure 10C:
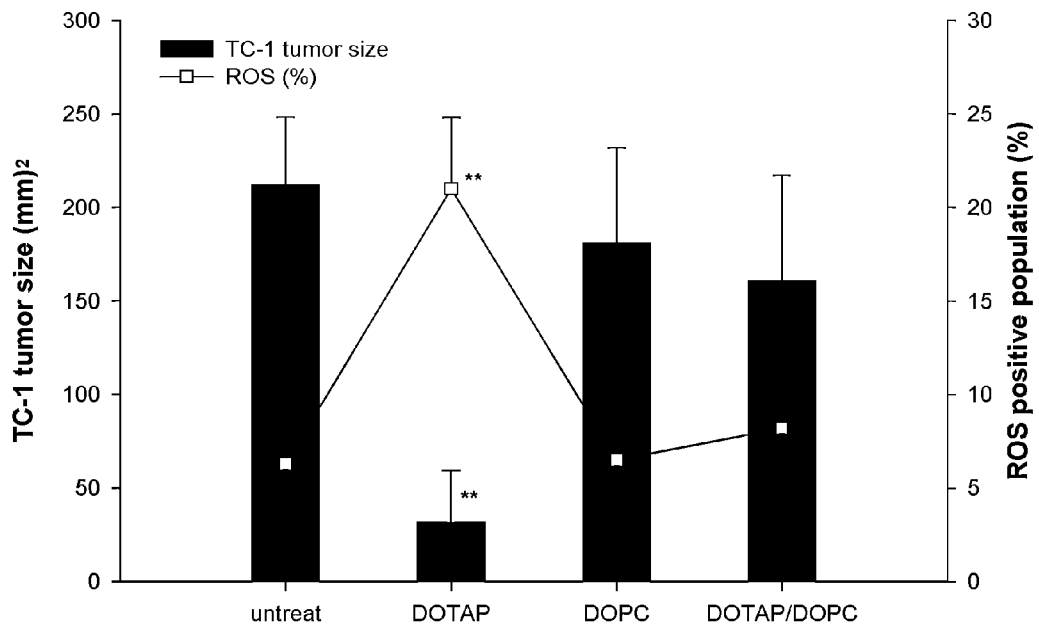

Further, as illustrated in FIG. 10C, the density of the cationic charge is important for the immunostimulatory effect and resulting anti-cancer activity. Both ROS generation and anticancer activity were diminished by co-formulating high ratios of an inert, neutral lipid, DOPC with the cationic lipid/E7 complex, resulting in a decrease of the cationic charge density.

15. Lipidation of a Peptide Antigen Results in Improved Encapsulation into the Cationic Lipid/Antigen Complex Cationic lipid/antigen complexes were prepared as described above. Peptide encapsulation efficiency was determined by the percentage of the liposome-bound peptide using LavaPep™ peptide quantification kit (commercially available from Fluorotechnics of Sydney, Australia). Since unincorporated lipopeptide aggregated and could not pass the exclusion filter, the incorporated lipopeptide was measured as the amount associated with the extruded liposomes in the presence of 1% SDS and reported as the mean±SD (n=3). For water-soluble peptide such as native E7 and KSS-E7, the unbound peptide was separated from the complex by a Microcon® centrifugal filtration device (commercially available from Millipore of Bedford, Mass.). The concentration of the unbound peptide was measured using LavaPep™ according to the manufacturer's instruction. The efficiency of encapsulation was determined as (1-% unbound peptide) and was reported in Table 2 as the mean±SD (n=3).

TABLE 2

Composition of the synthetic lipopeptides and comparison of peptide antigen entrapment efficiency in DOTAP liposomes at molar ratio lipopeptide: DOTAP = 1:40

| Peptide name | Peptide composition | | | Entrapment efficiency (%) |
|---|---|---|---|---|
| | Lipid | Spacer seq. | CTL epitope | |
| Native E7 | — | — | RAHYNIVTF [SEQ. ID. NO. 1] | 27.1 ± 5.8% |
| KSS-E7 | — | KSS | RAHYNIVTF [SEQ. ID. NO. 1] | 26.4 ± 6.1% |
| PA-E7 | Palmitic | — | RAHYNIVTF [SEQ. ID. NO. 1] | 84.5 ± 6.4% |
| α-PA-KSS-E7 | Palmitic | KSS | RAHYNIVTF [SEQ. ID. NO. 1] | 92.8 ± 4.2% |
| β-PA-KSS-E7 | Palmitic | KSS | RAHYNIVTF [SEQ. ID. NO. 1] | 94.1 ± 4.6% |

Figure 11:
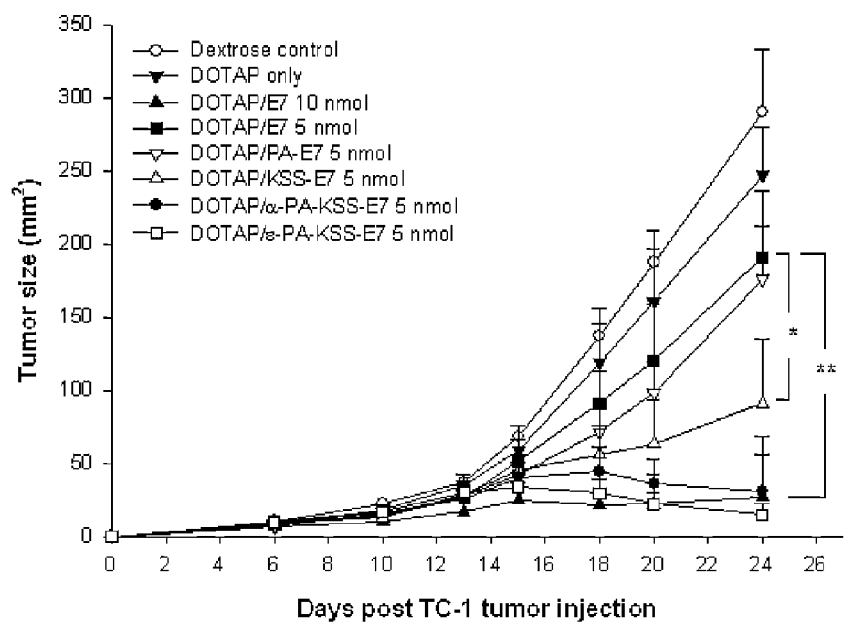
FIG. 11 illustrates the effect of improved encapsulation efficiency on the resulting immune response due to the cationic lipid/antigen complex. Anti TC-1 tumor activity was enhanced by incorporation of E7-lipopeptide in the cationic liposomal formulation. TC-1 tumor bearing mice (8-12 mice per group) received a single treatment on day 6 with DOTAP/E7 (containing E7 peptide of 5 or 10 nmols) or DOTAP/E7-lipopeptide (containing 5 nmol peptide) or DOTAP lipid alone. Mice treated with dextrose (5%) were used as a negative control. The mean of tumor sizes of each group at day 24 was compared to that of the group which was received DOTAP/E7 (5 nmol) and was analyzed by Student's t-test (*p<0.05, **p<0.01).

16. Anti-Tumor Efficacy of the Cationic Lipid/Antigen Complex Improves with Antigen Encapsulation Efficiency TC-1 tumor bearing mice (8-12 per group) were given a single-dose treatment on day 6 (after establishment of the tumor) with DOTAP/E7 (containing 10 nmol or 5 nmol peptide) or DOTAP/E7-lipopeptide formulations (containing 5 nmol of peptide antigen). Compositions of 100 nmole of cationic lipid were used in each case. DOTAP/E7 with 5 nmol of peptide did not show a significant anti-tumor activity. On the contrary, both of the E7-lipopeptides (α or ε position) at 5 nmol of antigen, when formulated in DOTAP liposomes, showed a significant enhanced therapeutic effect (**p<0.01) compared to DOTAP with the native E7 antigen at 5 nmol (FIG. 11). The anti-tumor activity elicited by the lipopeptides was similar to that of DOTAP/E7 with 10 nmol. PA-E7, which is a palmitoylated E7 peptide (without KSS spacer), when formulated in DOTAP liposome failed to show an enhanced anti-tumor activity as seen in other lipopeptide formulations, likely owing to the epitope being hidden by directly attaching a fatty acid to the peptide. Anti tumor activity is enhanced with DOTAP/E7-lipopeptide due, at least in part, to increased encapsulation efficiency of the antigen. This demonstrates that by increasing the hydrophobicity of the antigen, incorporation into the complex is increased resulting in an increased antigen-specific immune response. Mice treated with dextrose (5%) were used as a negative control.

17. Cationic Lipid/Lipidated Antigen Complex Increases Antigen Specific CTL Response.

Figure 12:
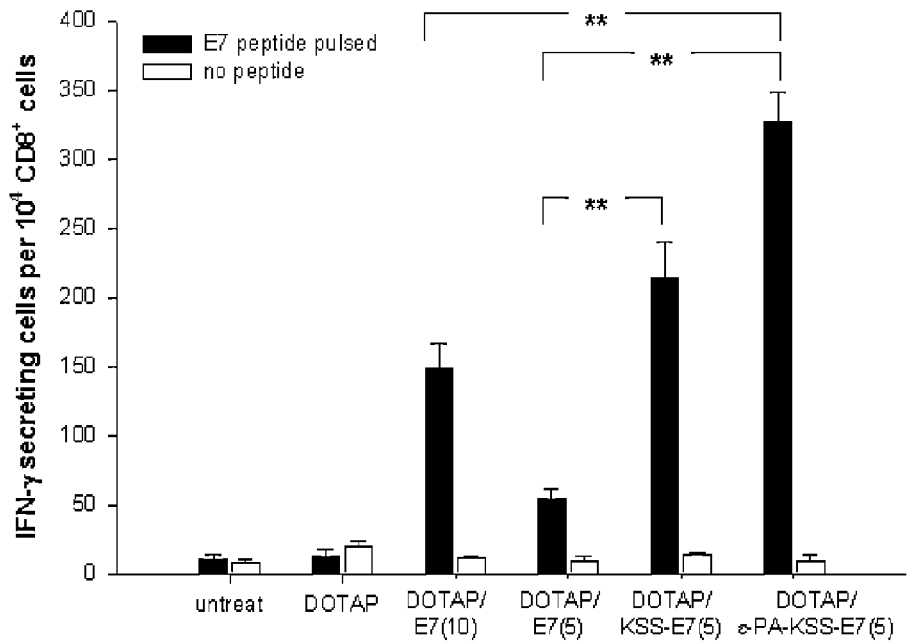
FIG. 12 is a graph demonstrating that immunization of mice with DOTAP/E7-lipopeptide induces increased secretion of IFN-γ in CD8$^+$ T cells.

Immunization with DOTAP/E7-lipopeptide increased the production of IFN-γ secreting CD8$^+$ T cells. Mice were injected with the various formulations and seven days after the last immunization, spleen cells from immunized mice were isolated. The cells were stimulated in vitro with or without E7 peptide (5 μg/ml) for 6 h, and were stained with a surface CD8 marker and an intracellular IFN-γ cytokine prior to FACS analysis. The percentage of CD8$^+$IFN-γ$^+$ double positive cells per $10^4$ total CD8$^+$ from each treatment group were shown in FIG. 12 as mean±SD and were statistically analyzed by paired t-test (**p<0.01, n=4).

To assess the epitope-specific immune response induced by DOTAP/E7-lipopeptide vaccination, IFN-γ producing CD8⁺ T cells were analyzed. Spleen cells from control or immunized mice were isolated at one week after the final immunization and were stimulated with 5 μg/ml E7 peptide or without peptide followed by intracellular staining for IFN-γ. As described in Table 2 (above) and depicted in FIG. 12, antigen incorporation into the complex was significantly improved in the case of the lipopetide antigen, and the number of IFN-γ producing CD8⁺ cells were therefore significantly higher in the mice that received 5 nmol of ε-PA-KSS-E7 formulated in the DOTAP liposomes than those of both 10 and 5 nmols of the native E7 (**p<0.01). Again, KSS-E7 showed a superior result than the native E7 at the equal antigen amount. The IFN-γ production by the CD8+ cells was E7-specific, as the unpulsed cells showed only background level of the cytokine. These results showed that incorporation of E7-lipopeptides with increased hydrophobicity and complexation efficiency into DOTAP liposomes clearly enhanced efficacy of the cationic lipid/antigen complex and increased the amount of IFN-γ producing CD8⁺T lymphocytes in the lymphoid organ.

Figure 13:
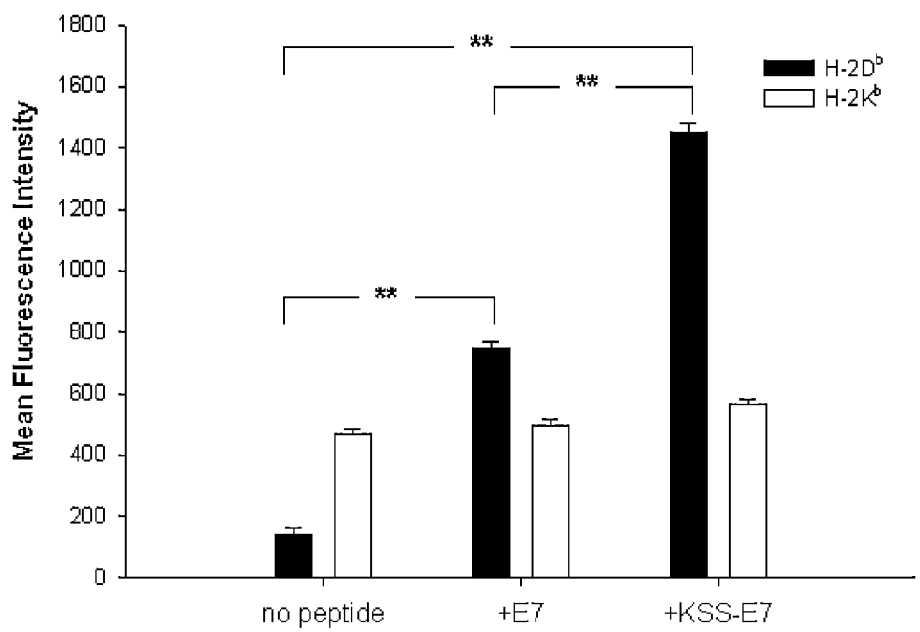
FIG. 13 is a graph illustrating increased immunogenicity of peptide antigen attached to short unrelated amino acid sequence.

18. Antigenicity of the Peptide Antigen is Improved by the Attachment of a Short Amino Acid Sequence Unrelated to Sequences Existing in the Parent Peptide Sequence, Leading to Improved Anti-Tumor Efficacy of a Lipid/Antigen Complex Consisting of DOTAP and KSS-E7 Peptide The KSS (lysine-serine-serine)-E7 peptide without the lipid chain attached, when formulated in DOTAP cationic lipid, provided a much stronger immune response than the native E7 peptide formulated in the DOTAP complex (FIGS. 11 and 12), despite comparable encapsulation efficiency to that of the native E7 (Table 2). It is known that the capacity of a peptide to bind and stabilize MHC class I molecules can be directly correlated with its ability to induce specific CTL responses [Feltkamp, M. C. et al, *Vaccination with cytotoxic T lymphocyte epitope-containing peptide protects against a tumor induced by human papillomavirus type 16-transformed cells*. Eur J Immunol, 23, (9), 2242-2249 (1993)]. We evaluated the MHC class I binding affinity of native and KSS-elongated E7 peptides. RMA-S cells, a mouse lymphoma cell line at a concentration of $5 \times 10^5$ cells/ml were incubated overnight at 27° C. with native E7 or KSS-E7 peptide (10 μM). Cells incubated with medium were used as a control. Cells were then incubated for 2 h at 37° C. After washes, cells were stained with fluorescently conjugated monoclonal antibodies against H-2D$^b$ or H-2K$^b$ molecules on the cell surface prior to flow cytometry analysis. E7 peptide (a.a. 49-57) is a known epitope restricted to H-2D$^b$ and it caused a four-fold up-regulation of H-2D$^b$ molecules on RMA-S cells compared to the control (FIG. 13). An 8-fold increase in the mean fluorescence was observed for KSS-E7 peptide. No up-regulation of H-2K$^b$ molecules was detected on RMA-S cells after incubating with either E7 or KSS-E7 peptide. The results demonstrate that KSS-E7 has an improved binding affinity to H-2D$^b$ molecules than the native E7 peptide, which led to a superior anti-tumor activity when formulated in the DOTAP/antigen complex.

The study demonstrates that the immunogenicity of an immunogenic peptide can be improved or altered by attaching a short sequence of amino acids unrelated to the natural parent protein sequence from which the immunogenic peptide is derived.

19. The Effect of Ionic Interaction Between the Cationic Lipid and Antigen on the Efficiency of Antigen Incorporation into the Cationic Lipid/Antigen Complexes For these studies DOTAP was solublized in chloroform and dry films prepared from 7 mg of DOTAP in 16×100 mm glass tubes. After drying under vacuum the liposomes were hydrated with 0.5 ml of the antigen (HPV-16 E7, amino acids 11-20, YMLDLQPETT (SEQ. ID. NO. 2) in (1) a high ionic strength environment (15 mM sodium phosphate, 150 mM NaCl, pH 7.0), or (2) a low ionic strength environment (0.5 ml of the antigen in 15 mM sodium phosphate, 50 mM NaCl pH 7.0). Particle size was 100 nm.

Antigen encapsulation efficiency was analyzed by filtering the particles over a 100K Nanosep microfilter (commercially available from Pall Corp. of Ann Arbor, Mich.), for 20 minutes at 5000 rpm in a microfuge. The concentration of antigen in the starting buffer and in the flow-through from the Nanosep filters (unbound peptide) was analyzed by reverse phase chromatography to determine percent encapsulation. Encapsulation efficiency was calculated as (1-% unincorporated peptide) as seen in Table 3.

TABLE 3

Ecapsulation of antigen into cationic lipid/antigen complex is enhanced by increasing the negative charge on the antigen.

| Formulation Buffer | Percent Encapsulation |
| --- | --- |
| High ionic strength environment 20 mM Sodium Phosphate 150 mM NaCl, pH 7.0 | 22% |
| Low ionic strength environment 20 mM Sodium Phosphate 50 mM NaCl, pH 7.0 | 53% |

Ionic interactions are minimized in high ionic strength environment. Higher strength ionic environments effectively decrease the negativeBy increasing the ionic strength of the formulation buffer (150 mM NaCl), ionic interactions between the negatively charged antigen and the positively charged lipid were minimized resulting in reduced encapsulation. By reducing ionic strength, ionic interactions between the lipid and antigen were enhanced leading to greater incorporation of the antigen into the complex. Incorporation efficiency into the cationic lipid/antigen complex can therefore be enhanced by manipulating the antigen to increase the negative charge by altering the formulation buffer or by attaching an anionic or poly-anionic compound to the antigen.

Discussion

Figure 14A:
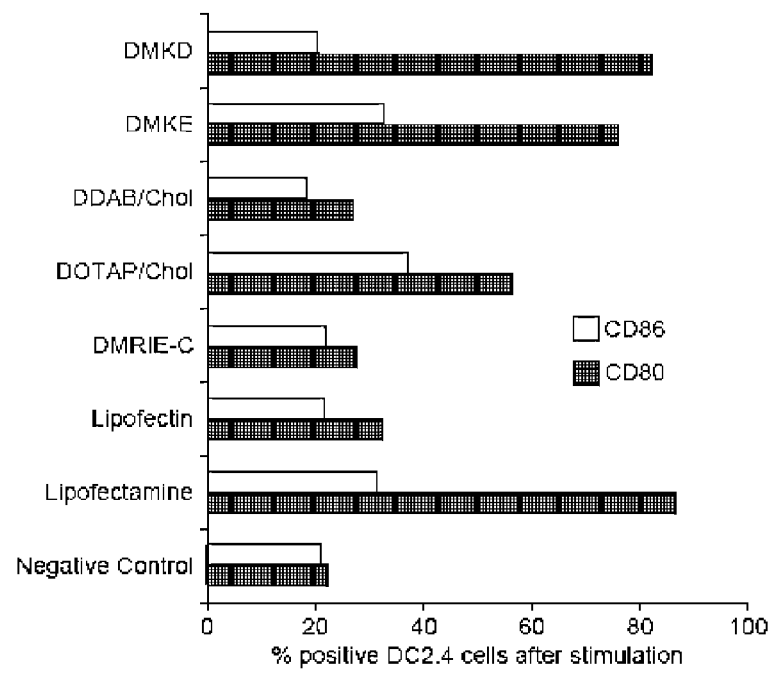
FIG. 14A is a graph illustrating the expression of co-stimulatory molecules, CD80 and CD86, on DC2.4 cells after stimulation with different cationic liposomes.
Figure 14B:
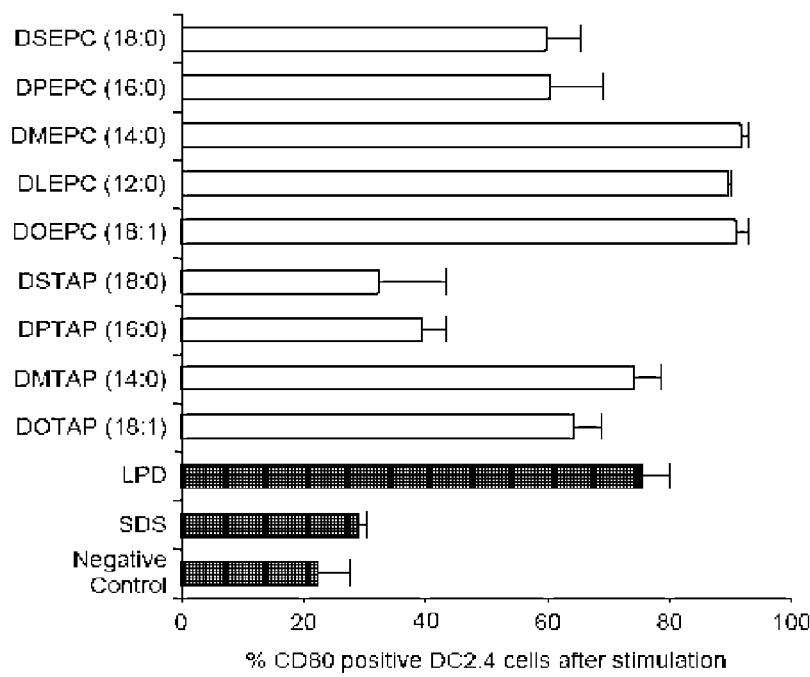
FIG. 14B is a graph illustrating the expression of hydrocarbon chain length dependence of cationic lipids on the expression of co-stimulatory molecule (CD 80) on DC 2.4 cells.

As described in U.S. Pat. No. 7,303,881, a broad class of cationic lipids can act as potent immunostimulators together with an antigen to generate antigen specific immune responses in the treatment of disease. For example, U.S. Pat. No. 7,303,881 discloses that liposomes comprised of cationic lipids activate dendritic cells as demonstrated by the stimulation by cationic lipids of the expression of costimulatory molecules CD80/CD86 on DC2.4 dendritic cells (FIGS. 14A and 14B). As shown in FIG. 14A, the ability to stimulate the expression of CD80/CD86 on DC2.4 cells by different cationic liposomes varies greatly. Lipofectamine®, a 3:1 (w/w) liposome formulation of the polycationic lipid 2,3-dioleyloxy-N-[2(sperminecarboxamido)ethyl]-N,N-dimethyl-1-propanamini-um trifluoroacetate (DOSPA) and the neutral lipid dioleoyl phosphatidylethanolamine (DOPE), and liposomes prepared from O,O'-dimyristyl-N-lysyl aspartate (DMKE) and O,O'-dimyristyl-N-lysyl-glutamate (DMKD), strongly stimulated the expression of CD80/CD86 by CD2.4 cells.

The ability of different cationic lipids to stimulate the expression of CD 80 on DC 2.4 cells varied. Both hydrophilic head and the lipophilic tail of the lipids have significant effect on this ability. For example, the DXEPC lipids with the ethyl phosphocholine (EPC) head groups appear, in general, to be more potent than the DXTAP lipids with trimethylammonium propane (TAP) head group. Within the lipids bearing one particular head group structure, lipids with shorter (1,2-dilauroyl-sn-glycero-3-ethylphosphocholine (DLEPC-12:0), 1,2-dimyristoyl-sn-glycero-3-ethylphosphocholine (DMEPC-14:0)) or unsaturated (1,2-dioleoyl-sn-glycero-3-ethylphosphocholine (DOEPC-18:1)) acyl chains appear to be more potent than those with longer (1,2-dipalmitoyl-sn-glycero-3-ethylphosphocholine (DPEPC-16:0)) or saturated (1,2-distearoyl-sn-glycero-3-ethylphosphocholine (DSEPC-16:0)) acyl chains (FIG. 14B). These data demonstrated that multiple cationic lipids were capable of stimulating the activation of dendritic cells. Three representative cationic lipids DOTAP, DOTMA, and DOEPC were therefore selected for additional studies to determine the mechanism by which cationic lipids act as immune stimulators. The data presented herein with the representative cationic lipids may be extrapolated to other cationic lipids that stimulate immune responses.

Data from the present studies have led to the observation that the cationic lipids are not only efficient targeting and delivery vehicles for antigens to APC of the immune system, but also function as potent adjuvants under low dose composition ranges to directly influence immune system function through activation of MAP kinase dependent signaling pathways with resultant production of immune system regulatory molecules including cytokines and chemokines. A clear dose-response effect of cationic lipid on the immunostimulatory capabilities of the formulations have been demonstrated. To this end, we have demonstrated that when an antigen, such as, for example, a peptide epitope of E7 protein of the HPV type 16, is encapsulated in the cationic liposomes of either DOTAP, DOTMA or DOEPC (DOTAP/E7, DOTMA/E7 or DOEPC/E7) and the antigen/lipid complex is administrated at about 100 nmole dose compositions by a single subcutaneous injection, it induces regression of the HPV 16 E7-positive tumor, TC-1, in mice. Upon receiving the lipid/antigen complex, the particles were mainly taken up by dendritic cells, the major professional antigen presenting cells. The initiation of dendritic cell activation and migration to the draining lymph node facilitates immune responses against antigen specific TC-1 tumors as demonstrated. Functional $CD8^+$ T lymphocytes were generated in mice upon receiving a DOTAP/E7 injection and tumor sizes decreased and exhibited enhanced apoptosis, owing to the increasing number of infiltrating T cells in the tumor microenvironment. The resulting bell-shaped (activity decreases above and below the optimal dose) cationic lipid dose response curve demonstrates activity at very low doses, indicating that the activity of the cationic lipids as adjuvants or immunostimulators is so potent that the $EC_{50}$ is as low as about 15 nmol per injection. High doses of cationic lipids eliminate the immunostimulatory activity. We have also demonstrated that when an antigen such as, for example, ovalbumin, is incorporated into the cationic liposomes and administered in a single subcutaneous injection, effective antibodies against the antigen are produced. It is clear that at optimal dose compositions, the cationic lipids and cationic lipid/antigen complexes provide simple, safe, and very efficient immunotherapies useful in preventing and treating diseases.

T regulatory cells were initially described by Gershon et al. [Eardley, D D, et al., *Immunoregulatory circuits among T-cell sets. I T-helper cells induce other T-cell sets to exert feedback inhibition*. J Exp Med 147:1106; and Cantor, H, et al., *Immunoregulatory circuits among T-cell sets. II. Physiologic role of feedback inhibition in vivo: absence in NZB mice*. J Exp Med 147:1116 (1978)] in the 1970s and were called suppressive T cells. Recent studies have explored the role of CD4+ CD25+ regulatory T cells (T-reg) in the suppression of tumor immunity in several murine models as well as in cancer patients [Comes, A, et al., *CD25+ regulatory T cell depletion augments immunotherapy of micrometastases by an IL-21-secreting cellular vaccine*. J Immunol 176:1750 (2006)]. The frequency of T-reg cell population increases in the peripheral blood of cancer patients [Sasada, T, et al., *CD4+CD25+ regulatory T cells in patients with gastrointestinal malignancies: possible involvement of regulatory T cells in disease progression*. Cancer 98:1089 (2003)]. They are also enriched among the tumor infiltrating lymphocytes and in the draining lymph nodes [Baecher-Allan, C, and Hafler, D A, *Suppressor T cells in human diseases*. J Exp Med 200:273 (2004)]. Also, accumulation of T-reg in tumor-associated tissue predicts poor prognosis or survival [Baecher-Allan, C, and Anderson, D E *Immune regulation in tumor-bearing hosts*. Curr Opin Immunol 18:214 (2006)]. Although the detailed mechanism of how T-reg dampens normal T-cell immunity is not well understood, it has been reported that the anti-tumor activity is enhanced by using anti-CD25 antibody to block T-reg cells [Attia, P, et al., *Inability of a fusion protein of IL-2 and diphtheria toxin (Denileukin Diftitox, DAB389IL-2, ONTAK) to eliminate regulatory T lymphocytes in patients with melanoma*. J Immunother 28:582 (2005)]. Indeed, it has become apparent that it will be necessary to monitor and characterize both the effector and T-reg responses in patients that receive candidate human tumor vaccines [Baecher-Allan, C, and Anderson, D E *Immune regulation in tumor-bearing hosts*. Curr Opin Immunol 18:214 (2006)]. In the present studies, we found a clear correlation of the anti-tumor activity of the DOTAP/E7 with the reduction of T-reg cells.

Cationic lipids therefore constitute a novel class of immune-stimulators that at specific doses can be applied effectively in modulating the body's immune response and in the development of therapeutic agents and vaccines for both prophylactic and therapeutic use.

It has been known for several years that proteins and peptides have significant potential for use in the development of immuno-therapies and vaccines. A major drawback to the successful development of such therapies has been inefficient delivery of the antigens to the immune system. Also, intensive efforts have been undertaken to develop safe and potent immune stimulants for use in infectious diseases and as therapies for cancer. Current technologies involving adjuvants such as Montanide ISA™ 51 and 720 from SEPPIC, Inc., which is a mixture of a surfactant from the mannide monooleate family with a mineral oil or nonmineral oil, respectively, have been tested in vaccines for infectious diseases and cancer in humans [Aucouturier, J, et al., *Montanide ISA 720 and 51: a new generation of water in oil emulsions as adjuvants for human vaccines*. Expert Rev Vaccines 1:111 (2002)]. Various studies demonstrate the ability of Montanide ISA™ 51 and 720 to enhance antibody titers and also specific CTL response [Yamshchikov, G V, et al., *Evaluation of peptide vaccine immunogenicity in draining lymph nodes and peripheral blood of melanoma patients*. Int J Cancer 92:703 (2001)]. However, this type of water-in-oil adjuvant requires a critical step of emulsification during the manufacturing process, which is not always easy to control. More importantly, a phase I clinical trial of a multi-epitope polypeptide TAB9 combined with Montanide ISA 720 indicated that seven out of eight volunteers from the lower dose group showed moderate or severe local inflammation, while four out of eight subjects from the higher dose group developed granulomas and sterile abscesses [Toledo, H, et al., *A phase I clinical trial of a multi-epitope polypeptide TAB9 combined with Montanide ISA 720 adjuvant in non-HIV-1 infected human volunteers.* Vaccine 19:4328 (2001)]. ISA 720 is composed of metabolizable oil and is supposed to be less reactogenic in humans. However, like most other adjuvants, the surfactant in the emulsion may trigger toll-like receptors (TLR) on dendritic cells and macrophages thus inducing the production of NF-κB and inflammatory responses [Aucouturier, J, et al., *Montanide ISA 720 and 51: a new generation of water in oil emulsions as adjuvants for human vaccines.* Expert Rev Vaccines 1:111 (2002)].

We have demonstrated that the cationic lipids do not enhance the expression of NF-κB, suggesting that dendritic cells stimulation by cationic lipids is signaled through an NF-κB independent mechanism [Cui, Z., et al (2005). *Immunostimulation mechanism of LPD nanoparticle as a vaccine carrier.* Mol Pharm 2: 22-28)]. Thus, cationic liposomes could belong to a unique class of adjuvant with an improved safety profile.

We have also demonstrated that by lipidating an antigen such as, for example, linking a mono-palmitic acid to a KSS-elongated E7 peptide (at either α or ε position), the peptide encapsulation efficiency within the cationic liposome/antigen complex can be improved over that of the water-soluble antigen. The DOTAP/E7-lipopeptide complex, which consists of only two molecules, induced an overall enhancement in generating antigen-specific CTL for eradicating HPV positive TC-1 cells. The cationic lipid composition was maintained at 100 nm. When the antigen was administered at a reduced dose (5 nmol or less) to tumor bearing mice, the DOTAP/E7-lipopeptide complex exhibited a superior anti-tumor activity compared to the original DOTAP/E7 formulation at a full dose (10 nmol). The enhanced antigenicity and anti-tumor activity of the lipopeptide was correlated with the enhanced encapsulation of the lipopeptide in the liposomes. As shown in Table 2, the entrapment efficiency of lipopeptide was 90% at a peptide loading of 2.5 mol % total lipid, whereas only about 25% of the native water soluble E7 peptide only got incorporated into the complex. Similar enhanced liposome encapsulation of lipopeptides has also been reported [Yagi, N. et al., *Preparation of functional liposomes with peptide ligands and their binding to cell membranes.* Lipids, 35, 673-680 (2000); and Liang, M. T. et al., *Encapsulation of lipopeptides within liposomes: effect of number of lipid chains, chain length and method of liposome preparation.* Int J Pharm, 301, 247-254 (2005)]. In order for the peptide to be presented by the MHC class I pathway, the peptide has to enter the cytoplasm of the APC. Cationic liposomes deliver the encapsulated, but not free, peptide into the cells. Thus, with higher the encapsulation of the peptide, better delivery and antigenicity can be expected. In addition, under dosing conditions as demonstrated, the cationic lipid also acts as a potent immunostimulator leading to a strong antigen-specific immune response resulting in the observed tumor cell death.

The importance of ROS has been implicated in innate immune response and T cell activation [Kantengwa et al, *Superoxide anions induce the maturation of human dendritic cells.* Am J Respir Crit. Care Med 167:431-437 (2003)], and high ROS production leads to cell death [Tobiume K, et al, *ASK1 is required for sustained activations of JNK/p38 MAP kinases and apoptosis.* EMBO Rep 2:222-228 (2001)], [Aramaki Y, et al, *Induction of apoptosis in WEHI 231 cells by cationic liposomes.* Pharm Res17:515-520 (2000)]. We demonstrated that ROS was induced by the cationic lipid in cells in the draining lymph node and a high dose of DOTAP lipid led to killing of dendtritic cells. Indeed, Iwaoka et al. have shown that cationic liposomes can induce ROS in macrophages in vitro [Iwaoka S, et al, *Cationic liposomes induce apoptosis through p38 MAP kinasecaspase-8-Bid pathway in macrophage-like RAW264.7 cells.* J Leukoc Biol 79:184-191 (2006)]. Data shown in FIG. 10A clearly demonstrate that cationic lipids are capable of generating ROS in vivo in the draining lymph node after subcutaneous injection of DOTAP/E7 complexes. The same data also suggest that excess ROS generated by a high dose of cationic lipid leads to enhanced dendritic cell death. These data support administering to a subject a cationic lipid in a dose sufficient to induce the production of ROS in cells of an immune system of the subject wherein the induced ROS level is sufficient to increase the immune response above the immune response present in the absence of the cationic lipid. There might be other possible reasons related to the loss of immunostimulation and resulting anticancer activity due to the high DOTAP dose of the DOTAP/E7 complex. However, the decreased amount of activated APC in the DLN should definitely play an important role in the observed decrease in the lymphocyte infiltration (FIG. 3), antigen-specific CTL activities and IFN-γ production (FIGS. 2 and 8) and, most importantly, the anti-tumor activity (FIG. 6) at the high vaccine dose. On the other hand, a desirable level of ROS production is required since DOTAP-induced ROS is probably the initial signal to mediate the subsequent signal transduction, such as the ERK and p38 MAP kinases, necessary for vaccine activity as discussed below in Example 2. Further, we have demonstrated the importance of the density of the cationic charge to the immunostimulatory effect and resulting anti-cancer activity in FIG. 10C. Here it is demonstrated that both ROS generation and anticancer activity can be diminished by co-formulating high ratios of an inert, neutral lipid, DOPC with the cationic lipid/E7 complex, resulting in a decrease of the cationic charge density.

Example 1 demonstrates the importance of the cationic lipid dose in the immunostimulatory effect and also highlights the role of cationic lipid/antigen complexes in the development of simple and safe immunotherapies to generate strong antigen-specific immune responses for the treatment of cancer and multiple diseases such as bacterial and viral infections.

Example 2

Mechanism Of the Immunostimulatory Activity of Cationic Lipids: Phosphorylation of a Map Kinase, ERK and Induction of Chemokines A. Materials and Methods
1. Cell Lines and Peptides TC-1 cells were provided by TC Wu (Johns Hopkins University, Baltimore, Md.). These cells are C57BL/6 mouse lung endothelial cells that have been transformed with the HPV16 E6 and E7 oncogenes and activated H-ras. Cells were grown in RPMI medium (commercially available from Invitrogen of Carlsbad, Calif.) supplemented with 10% fetal bovine serum and 100 U/ml penicillin, and 100 mg/ml streptomycin. The MHC class I restricted peptide from the HPV 16 E7 protein (amino acid 49 to 57, RAHYNIVTF [SEQ. ID. NO. 1]) was synthesized by the University of Pittsburgh Peptide Synthesis Facility by solid state synthesis using an Advanced ChemTech model 200 peptide synthesizer and purified by HPLC. [as described in Feltkamp, et al. *Eur J Immunol* 23, 2242-2249 (1993)]. Mouse monoclonal antibodies specific to pERK and ERK2 and siRNA were purchased from Santa Cruz Biotechnology, Inc. of Santa Cruz, Calif. Rabbit polyclonal antibody specific to phosphorylated p38 (p-p38) was obtained from Cell Signaling Technology Inc. of Danvers, Mass. GeneChip Mouse Genome 430 2.0 Array was obtained from Affymetrix, Inc. PD-98059, U-0126, PP2, wortmannin, and GF109203X were obtained from Calbiochem. Pertussis toxin and other reagents were obtained from Sigma.

2. Preparation of Lipid/Antigen Complexes and Determination of Physical Properties All lipids were purchased from Avanti Polar Lipids (Alabaster Ala.). Small unilamellar DOTAP, DOEPC, and DOTMA liposomes were prepared by thin film hydration followed by extrusion. The lipid, with or without a drug, in chloroform was dried as a thin layer under a stream of nitrogen in a glass tube. The thin film was vacuum desiccated for 2-3 h and then re-hydrated in cell culture grade water (commercially available from Cambrex of Walkersville, Md.) or buffer containing E7 peptide to a final concentration of 0.7 mg lipids and 0.1 mg E7 per mL (molar ratio=11:1). The lipid dispersion was sequentially extruded through polycarbonate membranes with pore size of 0.4, 0.2 and 0.1 μm. The unentrapped peptide was not removed. The liposomes were stored at 4° C. until use. E7 peptide association with the liposome was determined by measuring the percentage of liposome-bound peptide. In brief, unbound E7 peptide from DOTAP/E7 or DOTAP/E7/drug (MAP kinase inhibitor) complexes was separated by a Microcon® centrifugal filtrate devices (Millipore, Bedford, Mass.) and the concentration of unbound peptide was measured by Micro BC™ Protein Assay Kit (Pierce, Rockford, Ill. The efficiency of peptide association was determined as percent unbound peptide. Approximately 30% of E7 peptide was associated with the liposomes.

3. Statistical Analysis.

Data are presented as mean±SD of at least 3 independent experiments. Two-tailed Student's t tests were used to assess statistical significance for differences in means. Significance was set at $p<0.05$.

4. RNA Extraction and Microarray

RNA was extracted by RNeasy Mini Kit from Qiagen of Germantown, Md., according to the manufacturer's instructions. Seven μg of total RNA was used to synthesize cDNA. A custom cDNA kit from Life Technologies of Gaithersburg, Md., was used with a T7-(dT)$_{24}$ primer for this reaction. Biotinylated cRNA was then generated from the cDNA reaction using the BioArray High Yield RNA Transcript Kit. The cRNA was then fragmented in fragmentation buffer (5× fragmentation buffer: 200 mM Tris-acetate, pH8.1, 500 mM KOAc, 150 mM MgOAc) at 94° C. for 35 minutes before the chip hybridization. Fifteen μg of fragmented cRNA was then added to a hybridization cocktail (0.05 μg/μl fragmented cRNA, 50 pM control oligonucleotide B2, BioB, BioC, BioD, and cre hybridization controls, 0.1 mg/ml herring sperm DNA, 0.5 mg/ml acetylated BSA, 100 mM MES, 1M NaCl, 20 mM EDTA, 0.01% Tween 20). Ten μg of cRNA was used for hybridization. Arrays were hybridized for 16 h at 45° C. in the GeneChip Hybridization Oven 640. The arrays were washed and stained with R-phycoerythrin streptavidin in the GeneChip Fluidics Station 400. After this, the arrays were scanned with the Hewlett Packard GeneArray Scanner. Affymetrix GeneChip Microarray Suite 5.0 software was used for washing, scanning, and basic analysis. Sample quality was assessed by examination of 3' to 5' intensity ratios of certain genes.

5. Bone Marrow-Derived Dendritic Cells (BMDC)

BMDC were generated using a procedure modified from that described in Inaba K., et al., *Generation of large numbers of dendritic cells from mouse bone marrow cultures supplemented with granulocyte/macrophage colony-stimulating factor*. J Exp Med 176:1693-702, (1992). Briefly, bone marrow was harvested from the femurs and tibias of C57BL/6 female mice. After red blood cell lysis, plastic adherence allowed the separation of dendritic cell precursors from lymphocytes. The remaining bone marrow cells were cultured for 6 days in RPMI 1640 medium supplemented with 10% FBS, non-essential amino acids, antibiotic/antimycotic and GM-CSF and IL-4 (R&D systems) at 1,000 U/ml each. The medium was changed every other day. Cells were used in assays on day 6. These cells were >90% dendtritic cells, as verified by flow cytometry for CD11c expression.

6. RT-PCR

Total RNA was isolated from BMDC by Rneasy Mini Kit from Qiagen according to the manufacturer's instruction. Following digestion with Dnase for 30 min at 37° C., the total RNA concentration was determined by spectrophotometry. Primer pairs for mouse CCL2, CCL3, CCL4 and β-actin (forward primer 5'-AAGCCAGCTCTCTCTTCCTC-3' [SEQ. ID. NO. 3] and reverse primer 5'-CCTCTCTCTTTGAGCTTGGTG-3' [SEQ. ID. NO. 4] for CCL2; forward primer 5'-ATCATGAAGGTCTCCAC-CAC-3' [SEQ. ID. NO. 5] and reverse primer 5'-TCTCAG-GCATTCAGTTCCAG-3' [SEQ. ID. NO. 6] for CCL3; forward primer 5'-GCTCTGTGCAAACCTAACCC-3' [SEQ. ID. NO. 7] and reverse primer 5'-TGTGATGGTGG-GAATGGGTCAG-3' [SEQ. ID. NO. 8] and reverse primer 5'-TTTGATGTCACGCACGATTTCC-3' [SEQ. ID. NO. 9] for β-actin [Wang H., et al., *Potential involvement of monocyte chemoattractant protein (MCP)-1/CCL2 in IL-4-mediated tumor immunity through inducing dendritic cell migration into the draining lymph nodes*, Int Immunopharmacol 3:627-42, (2003)] were synthesized by IDT technology. RT-PCR was performed using the one-step RT-PCR kit (commercially available from Invitrogen of Carlsbad, Calif.) where reverse transcription and DNA amplification occur in the same reaction. Briefly, 1 μg of total RNA was used as a template in a reaction that included the appropriate primers in the presence of both reverse transcriptase and Taq polymerase. The mixture was incubated at 45° C. for 30 min and cycled 25 times at 94° C. for 30 s, 55° C. for 30 s, and 72° C. for 2 min. Appropriate negative controls of amplification included reactions without reverse transcriptase. PCR products were visualized by UV transillumination of 1.5% agarose gels stained with ethidium bromide.

7. CCL2 Production by Lymph Node Cells and BMDC after DOTAP Stimulation

Two days after C57BL/6 female mice (n=5) received subcutaneous injections of PBS, DOTAP/E7 or DOTAP/E7/MAP Kinase Inhibitor, the amount of CCL2 production within the draining lymph nodes was analyzed by CCL2 ELISA kit (commercially available from BD Biosciences). BMDC from C57BL/6 mice were cultured for six days in the presence of recombinant mGM-CSF and mIL-4 as described. At day 6, BMDC ($10^6$ cells in 1 mL/well) were stimulated with medium control or liposomes for 1 h, 24 h or 48 h at 37° C. For inhibitor treatment, the inhibitors were pre-incubated with BMDC for 20 min before liposome stimulation. The CCL2 production in supernatant was analyzed by CCL2 ELISA kit.

8. CCL2 Immunohistochemical Staining

The draining lymph nodes of mice were removed at day 2, embedded in OCT compound, snap frozen in liquid nitrogen, and stored at −80° C. until used for immunohistochemical analysis. The goat ABC Staining System (commercially available from Santa Cruz Biotechnology Inc. of Santa Cruz, Calif.) was used according to the manufacturer's protocol. Briefly, 8 μm thick crystostat sections of draining lymph nodes were cut and fixed in cold acetone for 10 min and washed in PBS 3 times for 5 min each wash. The sections were then sequentially incubated in 1% hydrogen peroxide (in $H_2O$) for 10 min to block endogenous peroxidases, in 1.5% blocking serum (donkey serum) in PBS for 60 min, then with the primary antibody (1:100 dilution; commercially available from Santa Cruz Biotechnology Inc. of Santa Cruz, Calif.) overnight at 4° C. The slides were then incubated with biotinylated secondary antibody (1:150 dilution; commercially available from Santa Cruz Biotechnology Inc. of Santa Cruz, Calif.) with AB enzyme reagent for 30 min and incubated in 3 drops peroxidase substrate for 10 min or longer.

9. Western Blot Analysis

BMDC cell lysate was collected after different treatments and total cellular protein was resolved on polyacrylamide/SDS gels and then transferred to polyvinylidene difluoride membranes. The membranes were blocked with 5% nonfat milk in Tris-buffered saline for 1 h and then incubated from 1 h to overnight with primary antibody. After washing the membranes with Tris-buffered saline three times, the membranes were incubated horseradish peroxidase conjugated secondary antibody for 1 h. The peroxidase activity associated with the protein bands was detected by enhanced chemiluminescence using ECL plus (Amershan International) followed by autoradiography.

10. siRNA Treatment

RNA interference experiments were performed with siRNA for ERK1 and control siRNA (commercially available from Santa Cruz Biotechnology of Santa Cruz, Calif.) using Lipofectamine 2000 reagent (commercially available from Invitrogen of Carlsbad, Calif.), according to the manufacturer's instructions. Briefly, on day 5, BMDC were seeded at $5 \times 10^5$ per well in 12 well plates and transfected immediately with 80 nM siRNA using 4 μl transfection reagent. The cells were incubated with DOTAP or LPS for another 16 h. The supernatant was analyzed by ELISA for CCL2.

B. Results

Figure 15A:
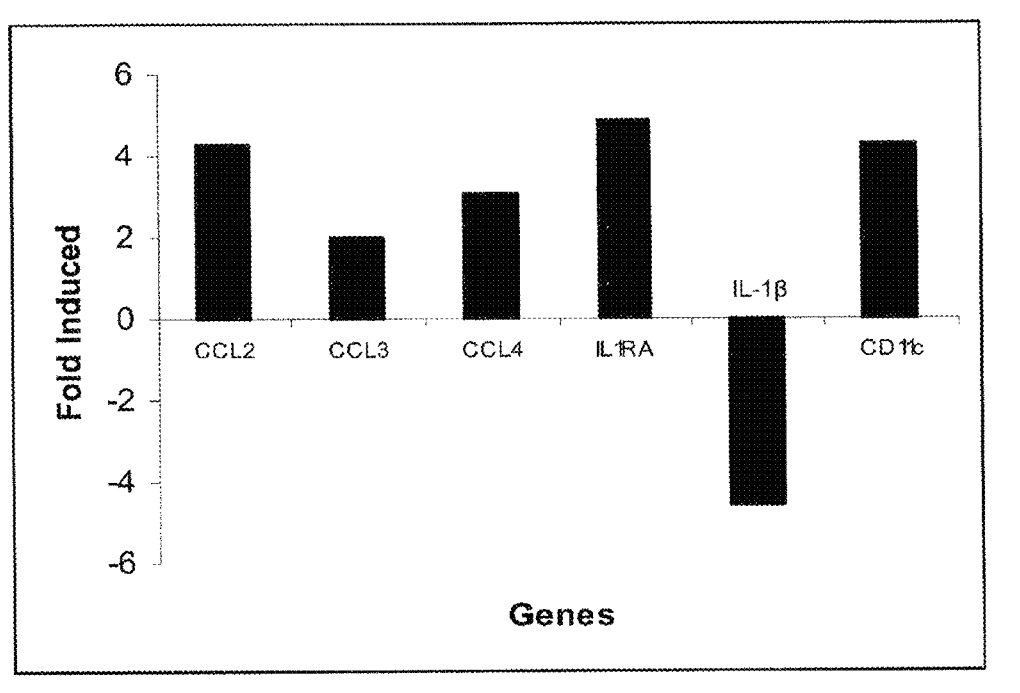
FIG. 15 Transcription of chemokines and CD11c are upregulated and IL-1 is down regulated by cationic liposomes. (A) Affymetrix microarray analysis showing fold increase in mRNA levels after DC2. Four cells were treated with 50 μM DOTAP liposomes for 24 h. (B) RT-PCR showing CCL2 and CCL4 are upregulated by DOTAP and 1,2-dioleoyl-sn-glycero-3-ethylphosphocholine ("DOEPC") in BMDC incubated with 50 μM DOEPC or DOTAP liposomes for 16 h followed by total RNA extraction and amplification with specific primers (100 ng/mL LPS as positive control).
Figure 15B:
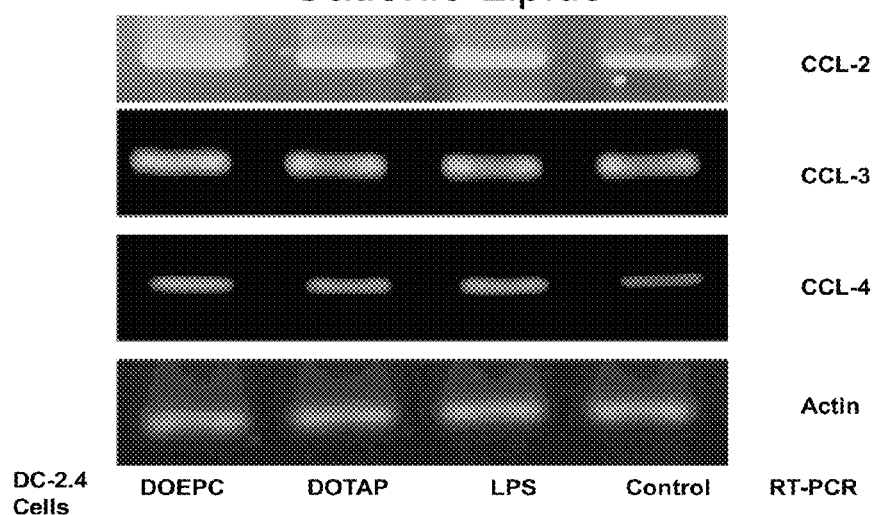

A transformed dendritic cell line, DC2.4, which has been shown to be a good model for APC [Mendoza L., et al., *Prophylactic, therapeutic and anti-metastatic effects of BMDC and DC lines in mice carrying HPV 16-associated tumours*, Int J Oncol 23:243-7, (2003); Okada N., et al., *Effects of lipofectin-antigen complexes on major histocompatibility complex class I-restricted antigen presentation pathway in murine dendriticcells and on dendritic cell maturation*, Biochim Biophys Acta 1527:97-101, (2001)], was used to study global gene regulation induced by DOTAP by using the Affymetrix microarray analysis (FIG. 15A). The data showed that DOTAP induced overexpression of several chemokines, including monocyte chemoattractant protein-1 ("MCP-1")/CC chemokine-2 ("CCL2"), macrophage inflammatory protein-1 alpha ("MIP-1α")/CC chemokine-3 ("CCL3"), macrophage inflammatory protein-1 beta (MIP-1β)/CC chemokine-4 ("CCL4"). Besides CC chemokine induction, the IL-1 signal was down-regulated, because IL-1 β was decreased and IL-1 receptor antagonist ("IL1RA") was increased upon 50 μM DOTAP treatment for 16 h. Interestingly, the dendritic cell marker, CD11c, was induced by the DOTAP liposomes, suggesting that the cationic lipids play a role in dendritic cell maturation. The induction of chemokine mRNA was confirmed by RT-PCR with murine BMDC (FIG. 15B).

Figure 16:
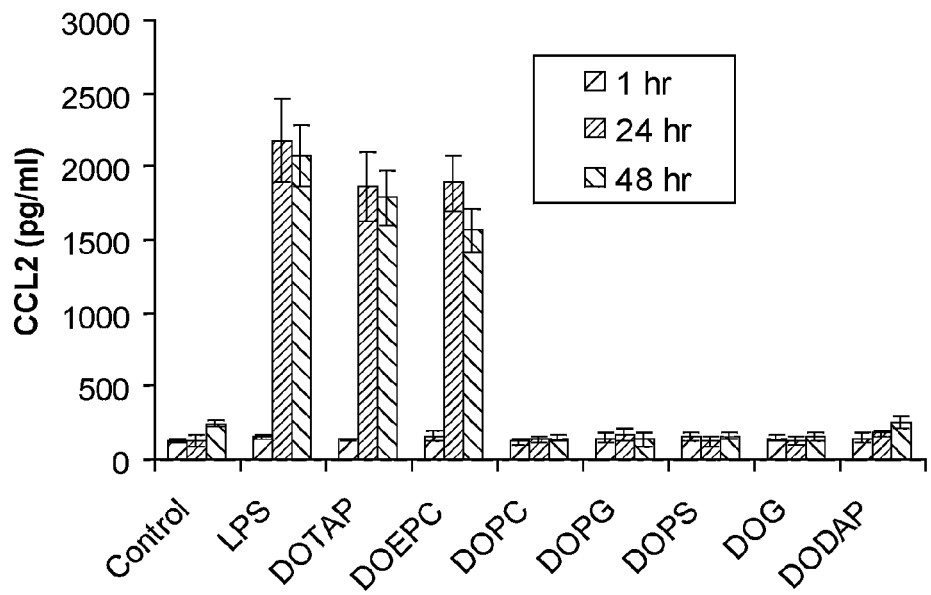
FIG. 16 Only cationic liposomes induce the CCL2 release from the BMDC.
Figure 17:
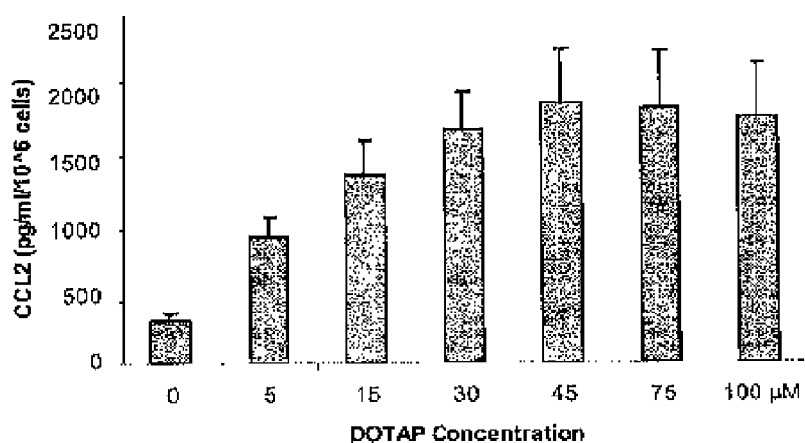
FIG. 17 DOTAP induces CCL2 release in a dose dependent manner
Figure 18:
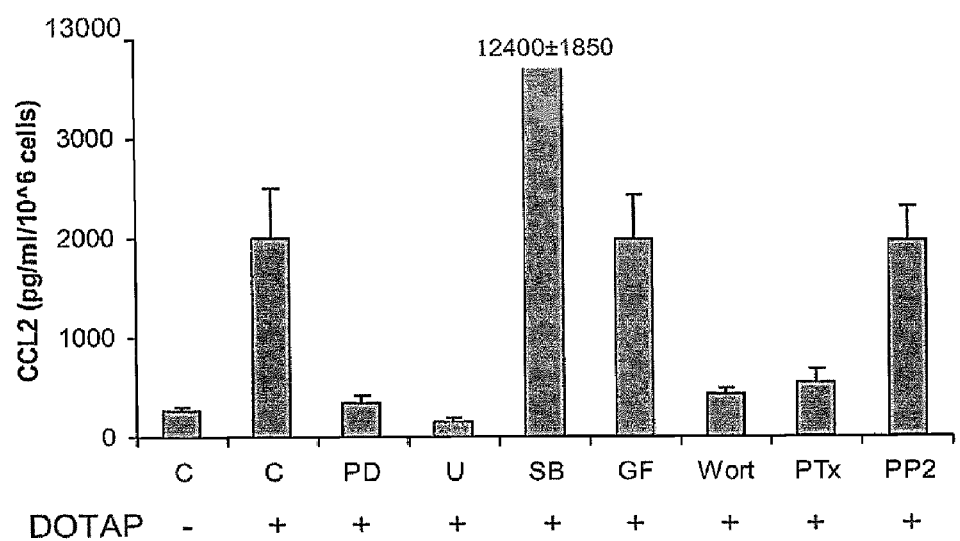
FIG. 18 MAP Kinase inhibitors were used to study the signaling pathways involved in the DOTAP-induced CCL2 release from BMDC. On day 6, BMDC were pre-incubated with inhibitors for 20 min, followed by 75 μM DOTAP liposome treatment for 24 h. The concentration used in the experiments are: PD (PD-98059), 20 μM; SB (SB-203580), 10 μM; U (U-0126), 10 μM; PTx (Pertussis Toxin), 200 ng/mL; PP2, 10 μM; Wort (Wortmannin), 200 nM; GF (GF 109203×), 200 nM. The supernatant was analyzed by ELISA. One hundred nanograms per milliliter LPS served as a positive control.

As mentioned previously, chemokines are involved in lymphocyte migration and play important roles in the immune response. Chemokine induction may explain the major adjuvant activity of cationic liposomes as mentioned previously. This hypothesis prompted us to further study the detailed mechanisms underlying the process. Liposomes prepared from different lipids were utilized to determine if the induction of chemokines is a general phenomenon by liposomes. Using BMDC, the results showed that only the quaternary cationic liposomes (DOTAP and DOEPC) induced the MCP-1/CCL2 release from BMDC. Neutral (DOPC and DOG) and negatively charged (DOPS and DOPG) liposomes did not (FIG. 16S). Also a tertiary amine analog of DOTAP, DODAP, did not induce the activity either, suggesting that the activity requires a quaternary amino head group in the lipid. LPS was also included in the experiments as a positive control. FIG. 16 also shows that the CCL2 induction by cationic liposomes reaches a maximum amount in 24 h, because 48 h incubation did not result in higher levels of chemokine production. Our data also show that DOTAP-induced CCL2 expression is dose-dependent (FIG. 17). Five μM DOTAP induced significant amounts of CCL2 from BMDC and maximum induction was reached at 45-75 μM. To identify which pathway was involved in the CCL2 induction by DOTAP in BMDC, several inhibitors specific to distinct signaling pathways were used. PD98059 ("PD") and U-0126 ("U"), specific inhibitors for the ERK pathway, almost completely abolished CCL2 production, but surprisingly, SB203586 ("SB"), an inhibitor of the p38 pathway, synergistically increased CCL2 production induced by DOTAP (FIG. 18). Our data also clearly showed that PKC pathway and Src kinase are not involved in the CCL2 production induced by DOTAP, because the PKC inhibitor GF109203X ("GF") and the Src kinase inhibitor PP2 had no inhibitory effect. FIG. 18 also indicates that PI-3 kinase and Gi-dependent G-protein-coupled-receptor (GPCR) were likely involved in the CCL2 release upon DOTAP treatment, because wortmannin ("Wort") and pertussis toxin ("PTx") had some inhibitory effect.

Figure 19A:
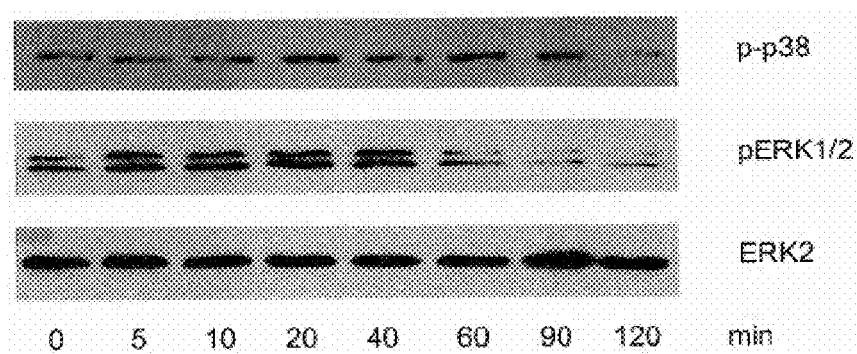
FIG. 19 DOTAP induces activation of ERK and p38 in BMDC. (A) Time course study. On day 6, BMDC were seeded in 12-well plate in the density of 106/mL/well. They were incubated with 75 μM DOTAP liposomes for the indicated time. The cells were harvested and subjected to Western blotting analysis using antibodies indicated in the figure. The same membrane was probed with ERK2 antibody to serve as a loading control. (B) DOTAP-induced activation of ERK was negatively regulated by p38. (C) DOTAP-induced ERK activation was mainly through PI-3 kinase and negatively regulated by p38.
Figure 19B:
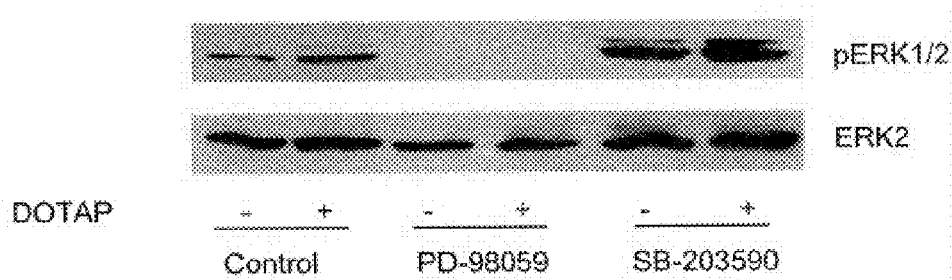
Figure 19C:
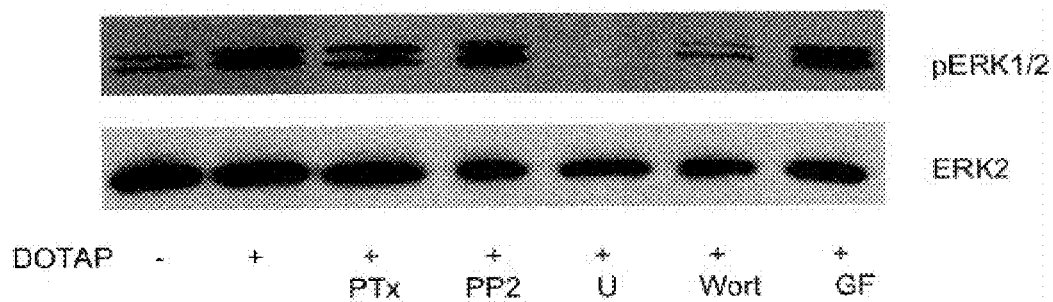

It is known that some chemokines are regulated by the ERK pathway [Yoo J. K., et al., *IL-18 induces monocyte chemotactic protein-1 production in macrophages through the phosphatidylinositol 3-kinase/Akt and MEK/ERK1/2 pathways*, J Immunol 175:8280-6, (2005)], and verified in our system. Using BMDC to study activation of the ERK pathway, our data showed that DOTAP induced ERK phosphorylation within 10 min of exposure and phospho-ERK (pERK) stayed at a high level for at least 40 min (FIG. 19A). In addition, p38 was also slightly activated by DOTAP. However, no phosphorylation of IκB and subsequent degradation were detected following DOTAP incubation (data not shown), suggesting that the NF-κB was not involved in the signal transduction initiated by DOTAP, consistent with our previous findings [Cui Z., et al., *Immunostimulation mechanism of LPD nanoparticle as a vaccine carrier*, Mol Pharm 2:22-8, (2005)]. Western blotting showed that inhibition of p38 could also synergistically increase the ERK phosphorylation triggered by DOTAP, suggesting that the ERK pathway and p38 are regulated reciprocally (FIG. 19B). In other words, activation of p38 may inhibit the activation of ERK. Consistent with the ELISA data in FIG. 18, our data have also shown that DOTAP-induced activation of ERK is mediated by PI-3 kinase because wortmannin inhibited ERK phosphorylation induced by DOTAP. However, PTx, the Gi inhibitor, only showed slight inhibitory effect on the DOTAP-induced ERK phosphorylation (FIG. 19C). On the other hand, the PKC pathway and Src kinase are not involved in this process, because GF and PP2 had no effect on the phosphorylation of ERK induced by DOTAP.

Figure 20A:
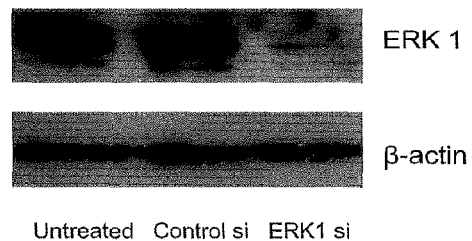
FIG. 20 Down-regulation of ERK gene expression by siRNA approach attenuates the DOTAP-induced CCL2 release from BMDC. (A) ERK1 gene expressionwas blocked by siRNA after 24 h treatment in BMDC. (B) ERK1 blockage by siRNA specifically attenuated DOTAP-induced CCL2 release from BMDC. DOTAP: 75_M, LPS: 100 ng/mL. *p<0.05 compared with control siRNA, n=3.
Figure 20B:
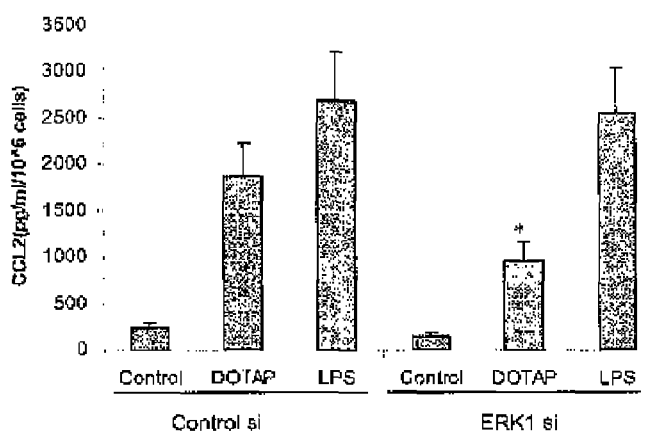

To further verify that the ERK pathway is involved in the CCL2 release initiated by DOTAP, the RNA interference approach was utilized to block the ERK gene expression in BMDC. FIG. 20A indicated that the ERK1 was down-regulated by specific siRNA after 24 h treatment. DOTAP-induced CCL2 release was also attenuated in the cells treated with siRNA, which blocked ERK1 gene expression (FIG. 20B). However, even though ERK1 was down-regulated, LPS continued to induce CCL2 release (FIG. 20B). The data also demonstrate that ERK1 siRNA treatment did not affect other signaling pathways.

Figure 21A:
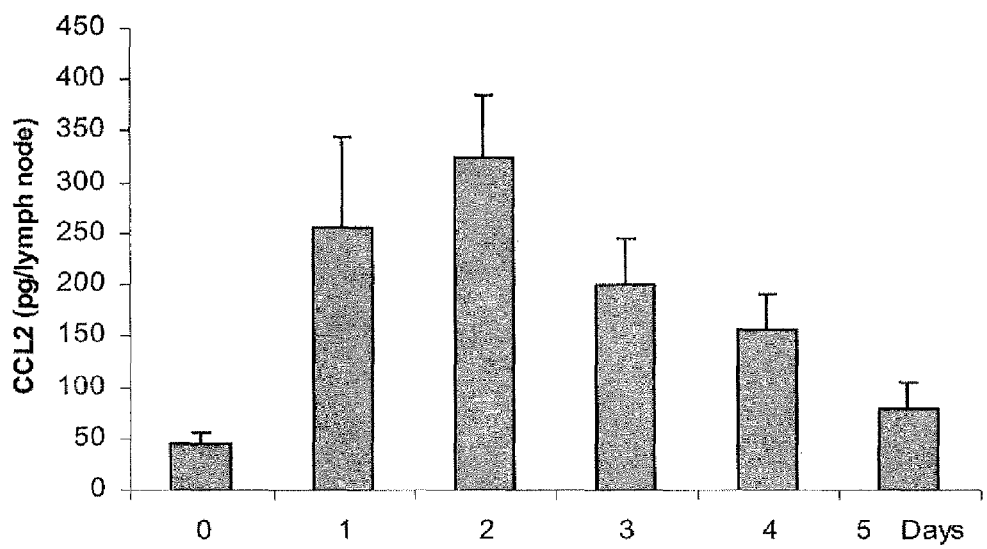
FIG. 21 DOTAP/E7 formulation induces the accumulation of CCL2 in the mice draining lymph nodes. On day 0, the mice (n=3) were injected with DOTAP/E7 formulation (100 nmol of DOTAP and 10 μg of E7 peptide). On indicated days, the mice were sacrificed and the draining lymph nodes were collected. The draining lymph nodes were either homogenized in 100 μL ELISA buffer (10% FBS in PBS) and then analyzed by ELISA (A) or immunochemically stained by CCL2 antibody (B) as mentioned in the text. Original magnification: ×400.
Figure 21B:
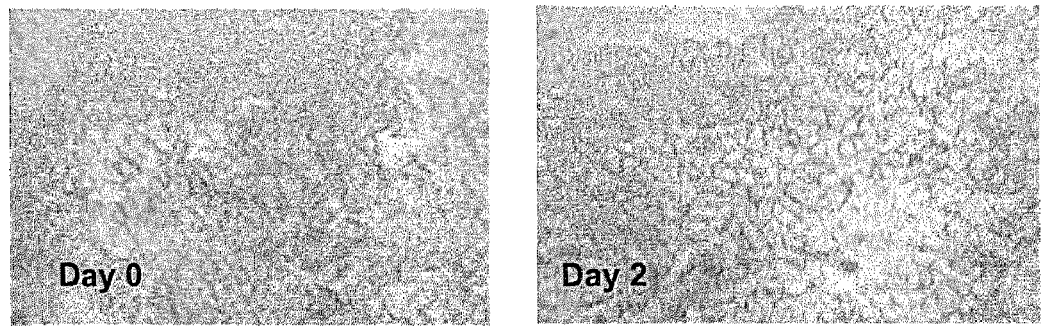

So far, the data demonstrate DOTAP-induced ERK activation and down-stream induction of CCL2 in vitro. We have investigated if the above signaling mechanism plays a role in the adjuvant activity of DOTAP in vitro. DOTAP/E7 liposome vaccine formulation was used to subcutaneously immunize mice, and the draining lymph nodes were collected and assayed by ELISA for CCL2. The data show that CCL2 accumulated in the draining lymph nodes after immunization and the maximum accumulation was 2 days post injection (FIG. 21A). These data were confirmed by immunohistochemistry staining (FIG. 21B). The same data also demonstrate that more lymphocytes migrated to the draining lymph nodes upon DOTAP/E7 treatment, resulting in the enlargement of the nodes.

Figure 22A:
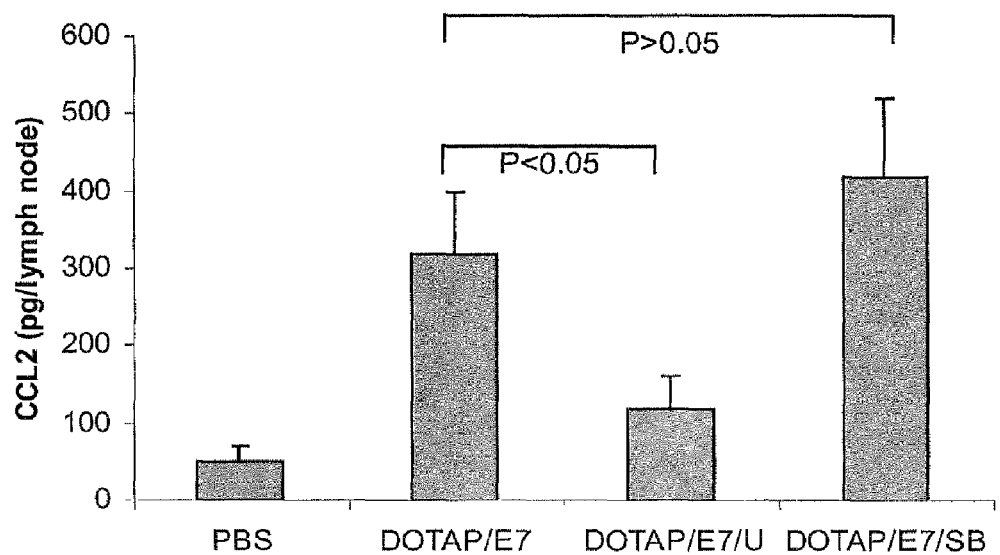
FIG. 22 Inhibition of ERK both attenuates the CCL2 accumulation in the draining lymph nodes and blocks the anti-tumor activity of DOTAP/E7 formulation. (A) CCL2 accumulation in the draining lymph nodes was reciprocally regulated by ERK and p38 pathways. (B) TC-1 tumor growth kinetics on mice that received DOTAP/E7 co-formulated with or without inhibitor. Mice (n=5) were injected with TC-1 cells (1×10$^5$/mouse) on day 0. On day 6, they were treated with DOTAP/E7, DOTAP/E7/U-0126, DOTAP/E7/SB or PBS. Tumor size was measured thereafter. *p<0.05, compared to the DOTAP/E7.
Figure 22B:
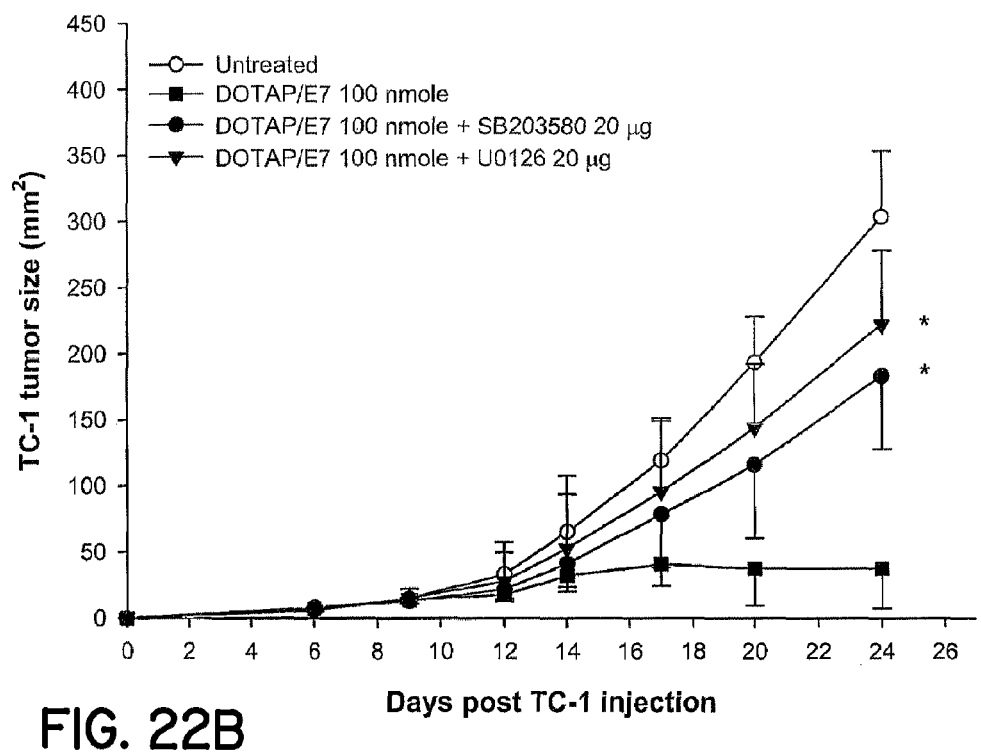
Figure 23A:
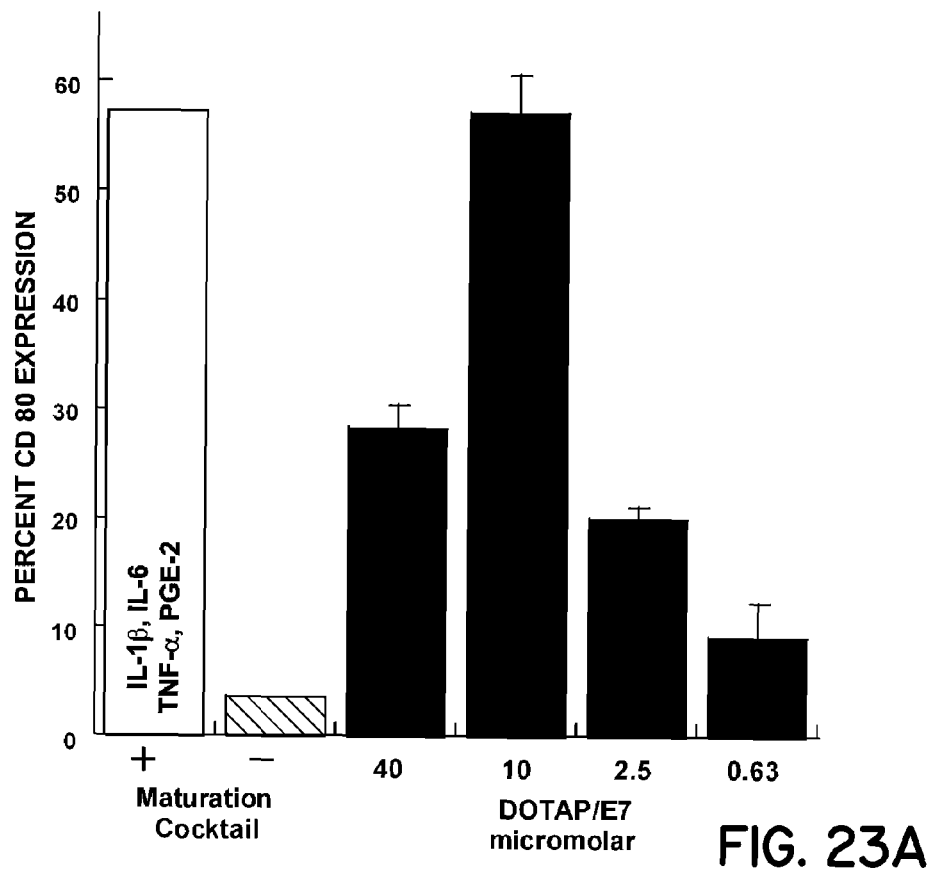
FIG. 23 Cationic lipid/antigen complexes effectively activate human dendritic cells.
Figure 23B:
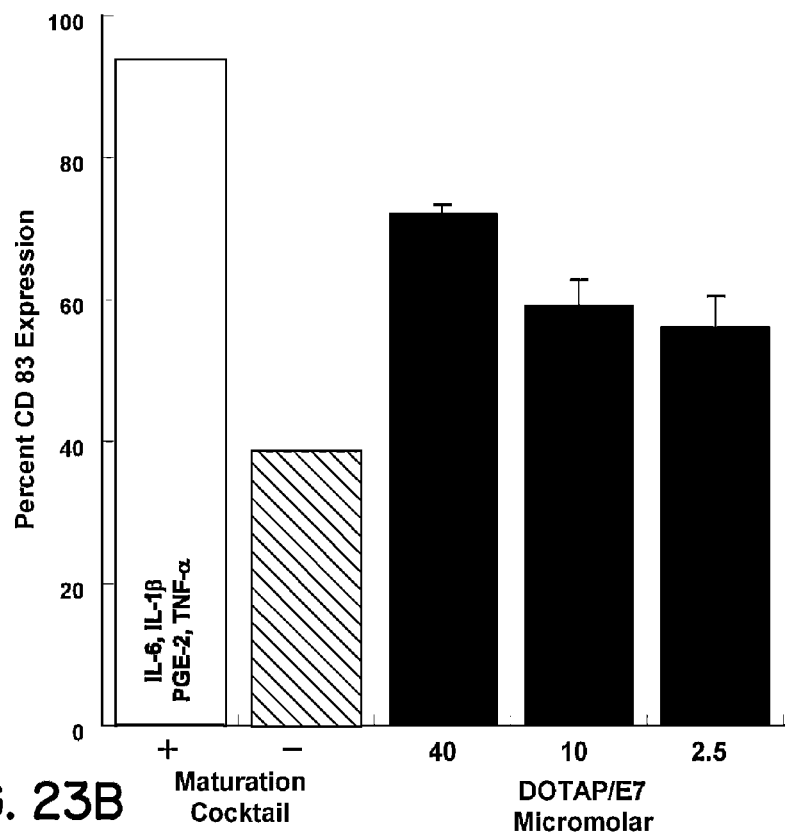
Figure 23C:
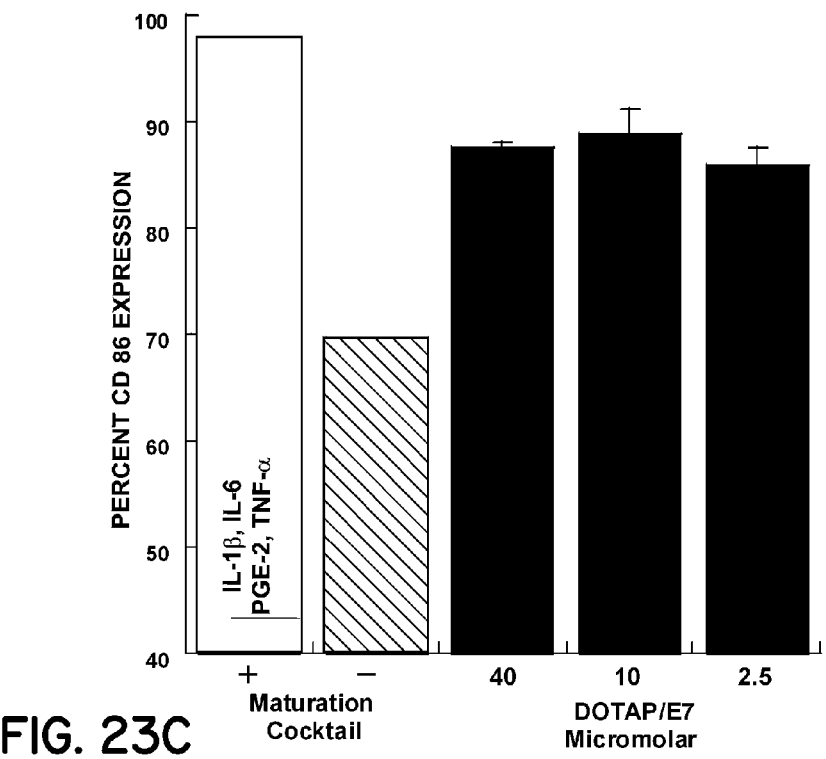
Figure 23D:
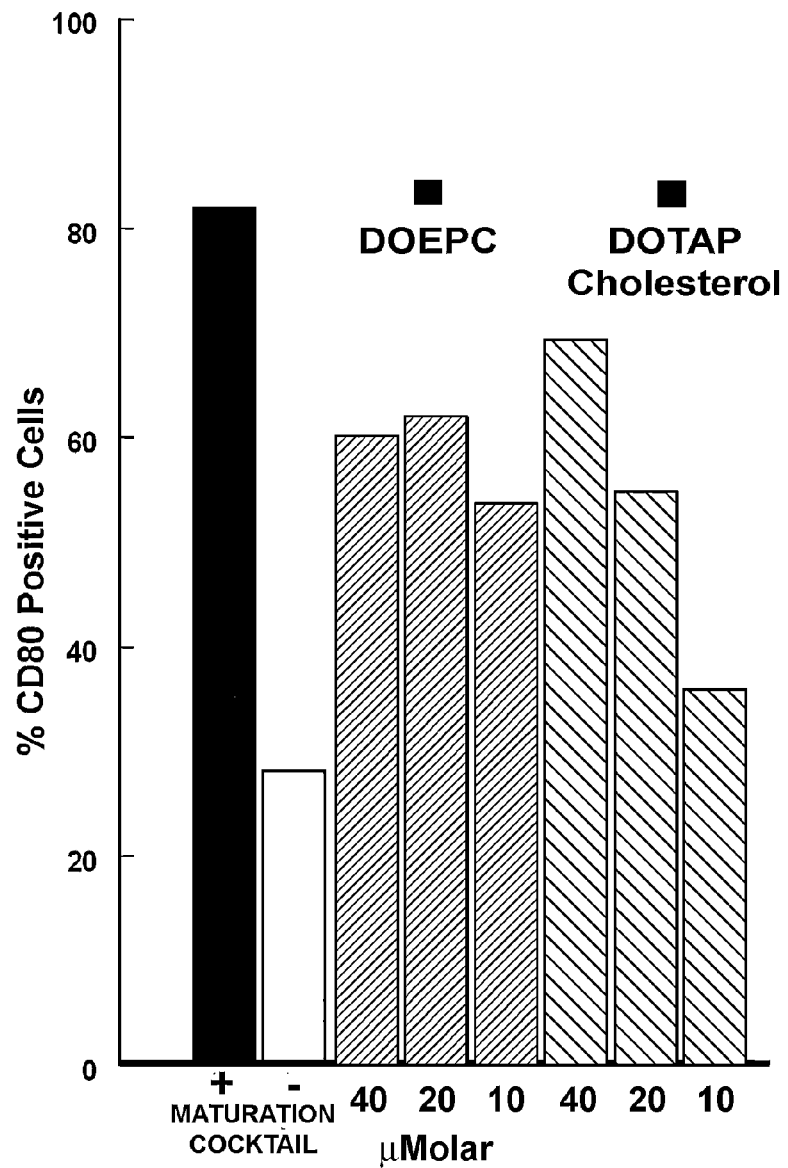
Figure 23E:
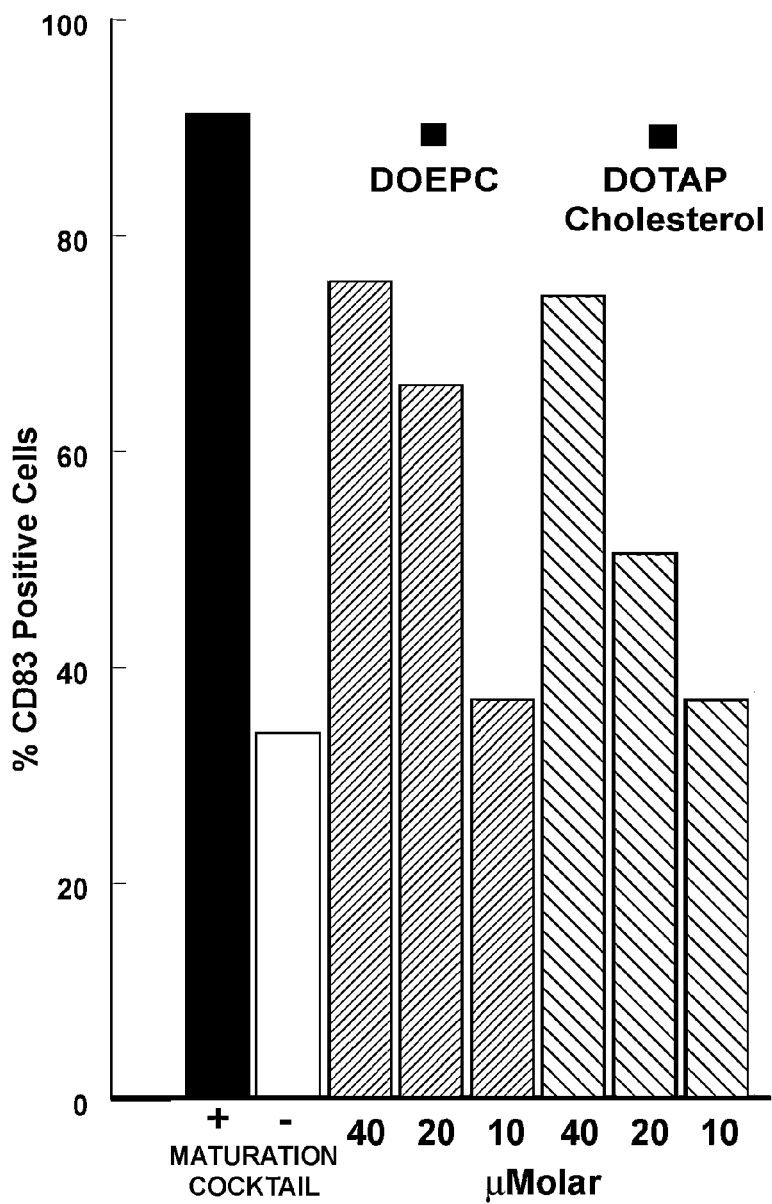
Figure 24A:
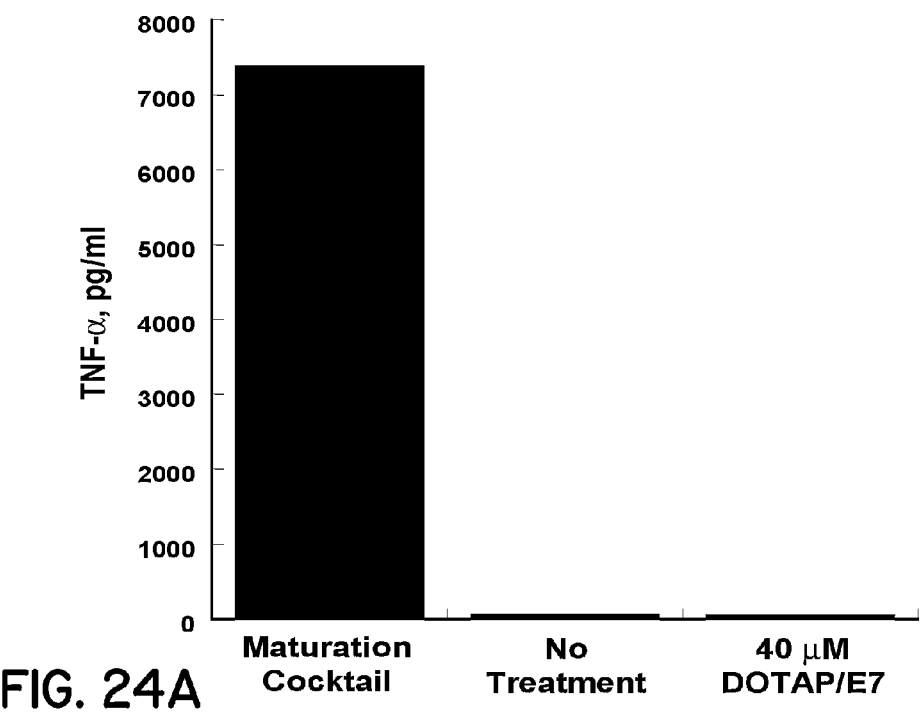
FIG. 24 illustrates the ability of DOTAP/E7 complex to induce cytokine and chemokine production by human dendritic cells.
Figure 24B:
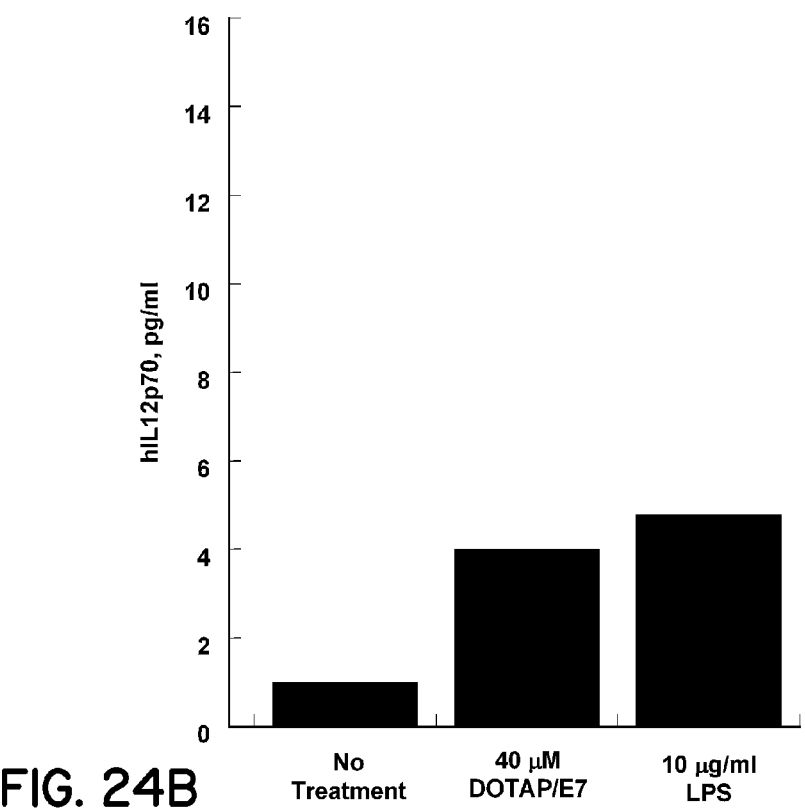
Figure 24C:
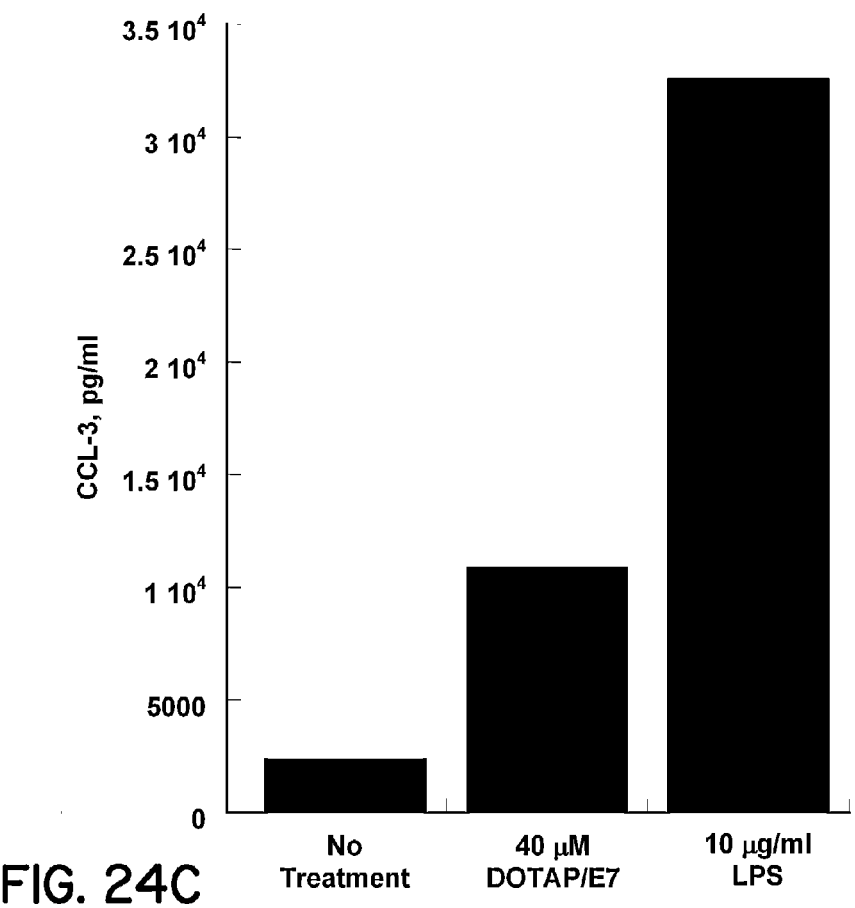
Figure 24D:
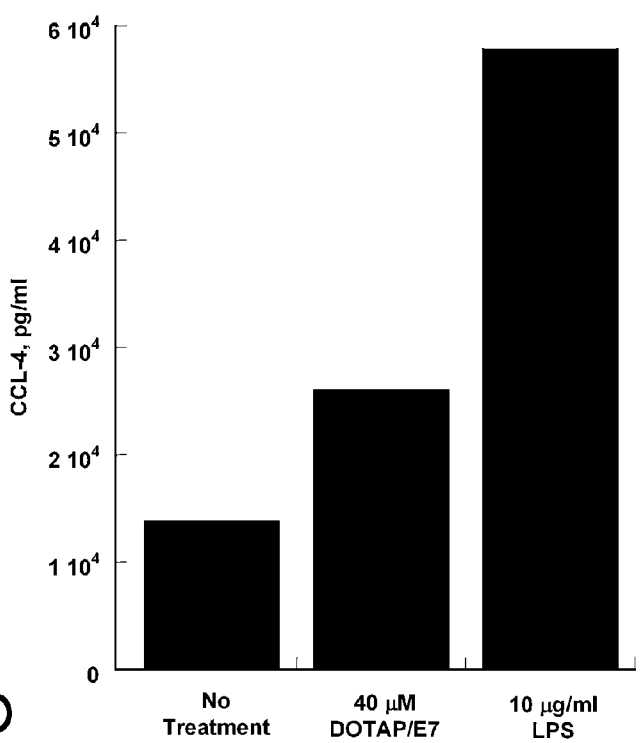
Figure 24E:
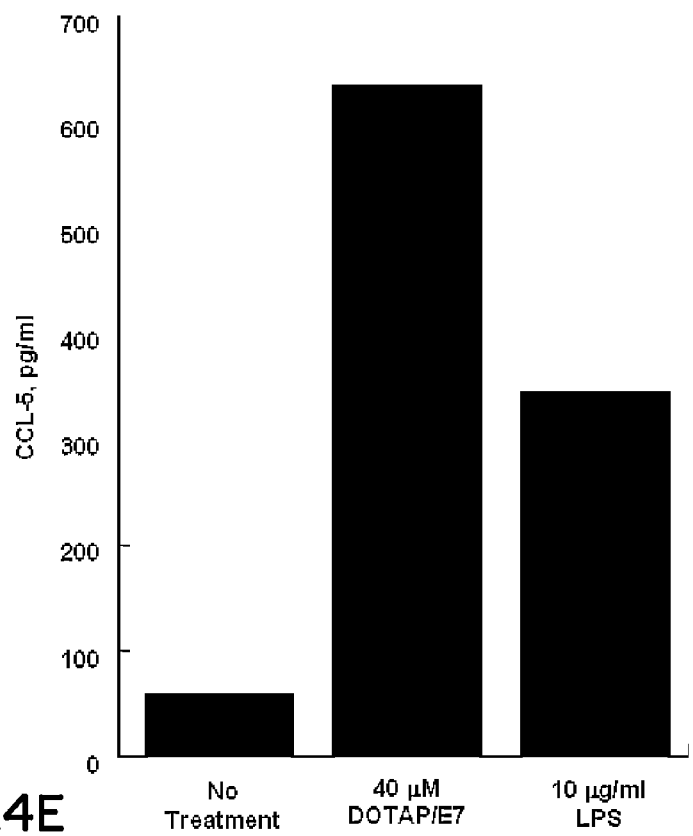
Figure 24F:
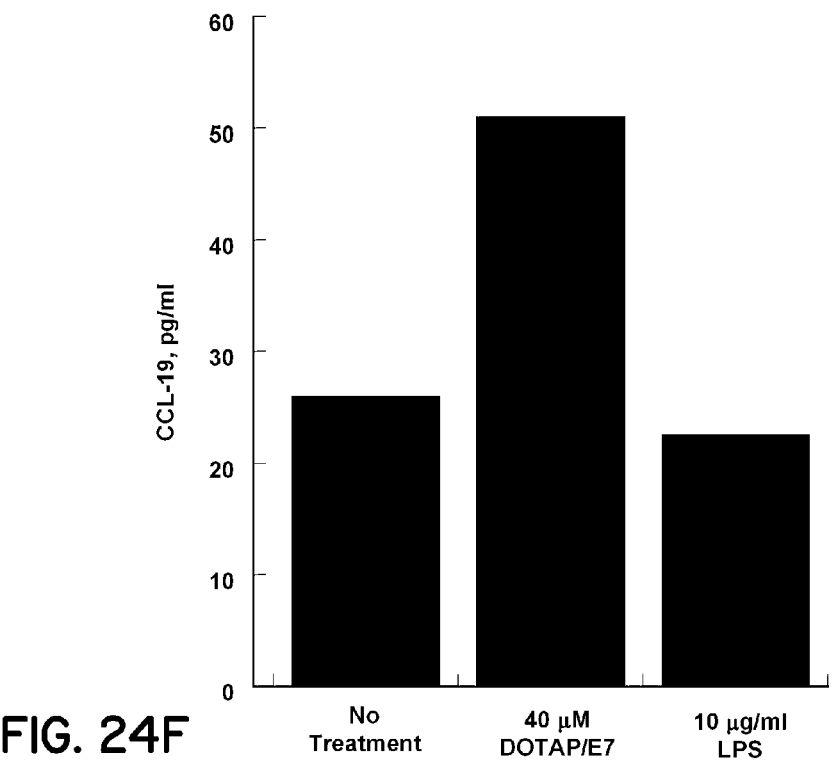
Figure 25A:
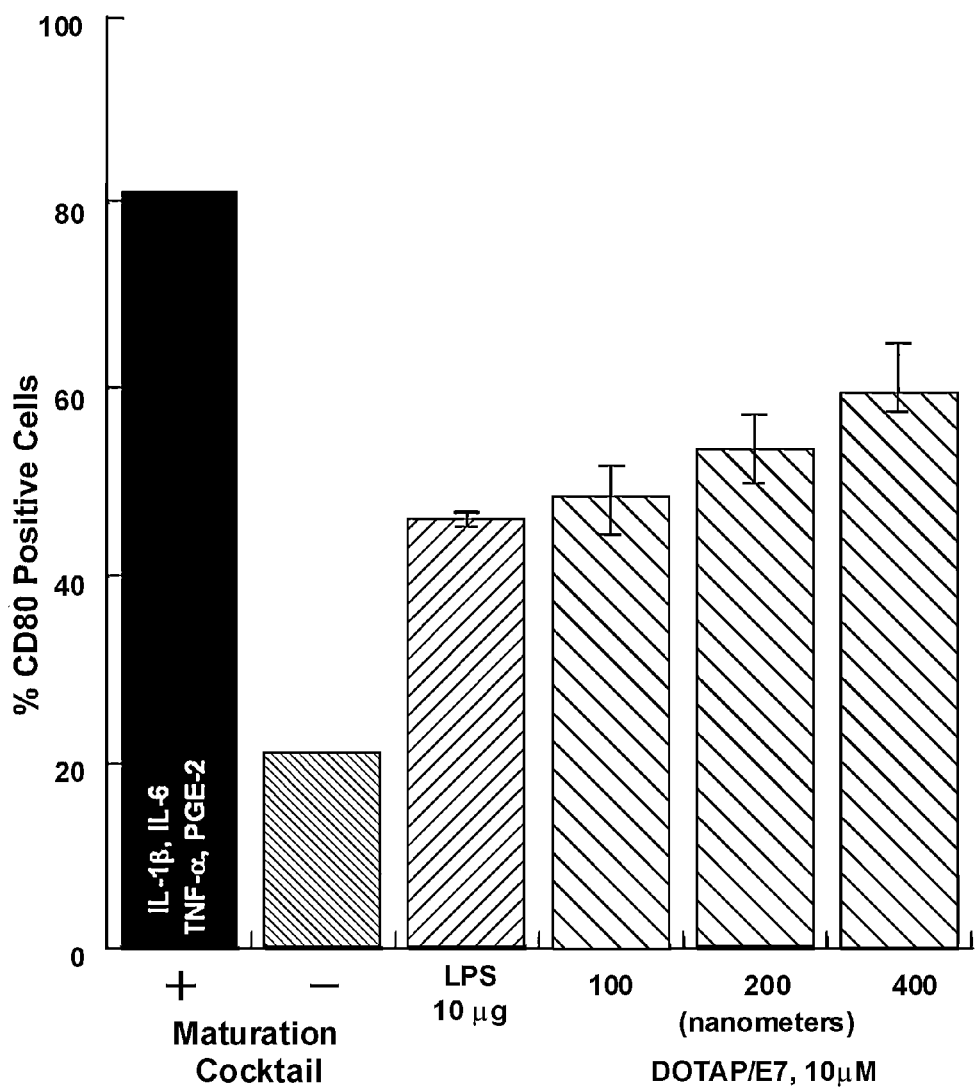
FIG. 25 illustrates the effect of the cationic lipid/antigen complex particles size on activation of human dendritic cells.
Figure 25B:
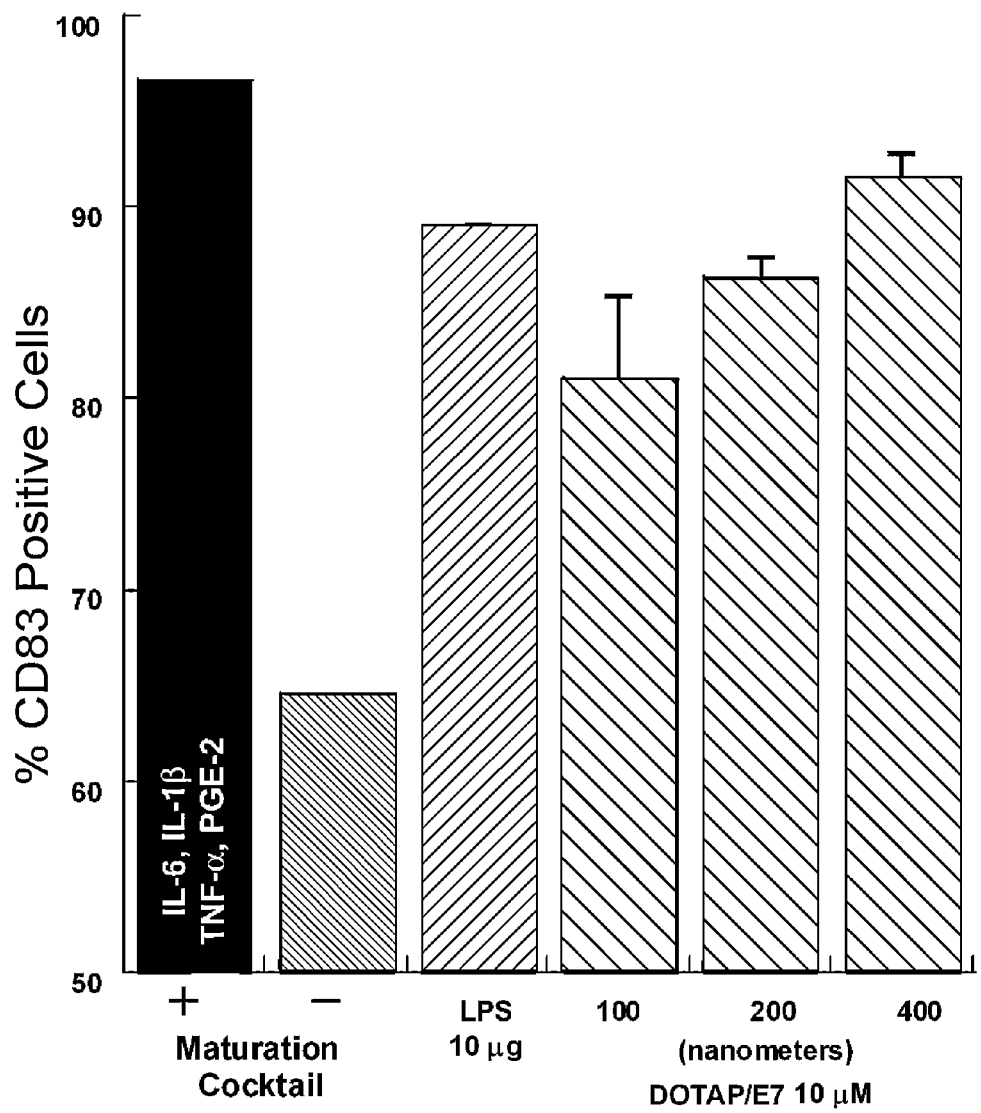

The inhibitors of ERK and p38 pathways were also formulated in the DOTAP/E7 liposome complexes. DOTAP/E7/U-0126 and DOTAP/E7/SB203580 formed clear suspensions but PD98059 was difficult to formulate in the DOTAP/E7 complex. The stable DOTAP/E7/drug formulations had similar zeta potentials, particle sizes and antigen loading capacities as the DOTAP/E7 formulation, indicating that drug incorporation did not significantly alter the physical characteristics of the vaccine. Mice were subcutaneously injected with DOTAP/E7/U-0126 and DOTAP/E7/SB203580. Consistent with the in vitro data, DOTAP/E7 formulation induced accumulation of CCL2 in the draining lymph nodes and U-0126 and SB-203580 reciprocally regulated CCL2 induction (FIG. 22A). In order to determine whether ERK and p38 pathways are related to the anti-tumor activity of DOTAP/E7, we have examined the anti-tumor activity of DOTAP/E7/drug formulations. As shown in FIG. 22B, tumor-bearing mice treated with DOTAP/E7 at the lipid dose of 100 nmoles exhibited a strong growth inhibitory effect on growth of TC-1 tumor. The ERK inhibitor, U-0126, when co-formulated with DOTAP/E7, at a similar lipid dose completely abolished the anti-tumor activity of DOTAP/E7. Similarly, partial inhibition of anti-tumor activity was shown when mice received treatment with DOTAP/E7 co-formulated with SB203580, indicating both p38 ERK pathways play important roles in the anti-tumor activity of the DOTAP/E7 complex.

C. DISCUSSION

Liposomes are closed vesicle structures consisting of bilayers of hydrated amphipathic lipids [Small D. M., *Surface and bulk interactions of lipids and water with a classification of biologically active lipids based on these interactions*, Federation Proc. 29:1320-1326, (1970)]. Since they were identified as adjuvants in 1974 [Allison A. G. and Gregoriadis G., *Liposomes as immunological adjuvants*, Nature 252:252, (1974)], liposomes have been extensively explored as a delivery system for protein and DNA vaccines [Chen W. C. and Huang L., *Non-viral vector as vaccine carrier*, Adv Genet. 54:315-37, (2005); Gregoriadis G., et al., *Vaccine entrapment in liposomes*, Methods 19:156-62, (1999); Perrie Y., et al., *Liposome-mediated DNA immunization via the subcutaneous route*, J Drug Target 11:555-63, (2003)]. Liposomes show several unique advantages for antigen delivery. Firstly, there is significant versatility in lipid composition, size, lamellarity, charge, and methods of preparation, which can be chosen for specific applications. Furthermore, considering the carrier to antigen ratio, the liposomal vesicle system has high efficiency of antigen loading in the form of encapsulation or stable association. From the safety point of view, liposomes are biodegradable, biocompatible and have a low immunogenicity [Copland M. J., et al., *Lipid bases particulate formulations for the delivery of antigen*, Immunol Cell Biol 83:97-105, (2005); O'Hagan D. T. and Singh M., *Microparticles as vaccine adjuvants and delivery systems*, Expert Rev Vaccines 2:269-83, (2003)]. Furthermore, liposomes have also been used to introduce protein antigens into the cytosolic MHC class I pathway to generate $CD8^+$ T cell responses [Chikh G. and Schutze-Redelmeier M. P., *Liposomal delivery of CTL epitopes to dendritic cells*, Biosci Rep 22:339-53, (2002)].

Since cationic liposomes can interact with the negatively charged cell membrane, they are widely used for gene therapy and vaccine delivery [Anderson P., *Effective vaccination of mice against Mycobacterium tuberculosis infection with a soluble mixture of secreted mycobacterial proteins*, Infect Immun 62:2536-44, (1994); Hasegawa A., et al., *Nasal immunization with diphtheria toxoid conjugated-CD52 core peptide induced specific antibody production in genital tract of female mice*, Am J Reprod Immunol 34:305-11, (2002)]. However, the cationic liposomes themselves have been regarded as being inert in terms of being able to activate innate immune responses [Moinegeon P., et al., *Towards the rational design of Th1 adjuvants*, Vaccine 19:4363-72, (2001)]. However, cationic liposomes can also induce expression of the co-stimulatory molecules CD80 and CD83 and activate human dendritic cells (FIGS. 23A-E and 25A-B). They also induce human dendritic cells to produce critical chemokines and cytokines involved with generating a potent immune response to disease (FIG. 24A-F). These findings all suggest that cationic liposomes in addition to effective delivery to the dendritic cells are potent activators of the immune system.

Unlike the currently used adjuvants such as Alum, CpG, and CFA, the cationic lipid immunomodulators do not enhance the expression of NF-κB, demonstrating that immune system stimulation by cationic lipids is signaled through an NF-κB independent mechanism, eliminating the probability of LPS-like inflammatory responses from our cationic lipid based therapies. These studies indicate that cationic liposomes, in addition to being an efficient delivery system, belong to a unique class of immune stimulants with an improved safety profile.

In this specification, the possible molecular mechanisms of the adjuvant activity of cationic liposomes were studied. Various components of the MAP Kinase signaling pathway were investigated for their role in the immunostimulatory activity of the cationic lipids. The lipids were investigated as an active stimulator of dendritic cells. It was demonstrated that chemokine production was induced by the cationic lipids and the induction was mainly mediated by the ERK pathway. Moreover, the data clearly show that the p38 pathway negatively regulates this process. A recent report demonstrated that p38 plays a negative role in IL-2 production, mainly mediated through its ability to regulate the activity of ERK. A p38-specific inhibitor induced ERK activation, ultimately leading to increased IL-2 gene activation [Kogkopoulou O., et al., *Conditional up-regulation of IL-2 production by p38 MAPK inactivation is mediated by increased Erk1/2 activity*, J Leukoc Biol 79:1052-60, (2006)]. Phosphorylation and activation of p38 enhances its interaction with ERK1/2 and correlates with the inhibition of ERK1/2 phosphotransferase activity, suggesting that activated p38 may sequester ERK1/2 and sterically block their phosphorylation by MEK1 [Zhang H., et al., *Stress-reduced inhibition of ERK1/2 and ERK2 by direct interaction with p38 MAP kinase*, J Biol Chem 276: 6905-8, (2001)]. Recent work suggests that the robust and sustained phosphorylation of ERK results in phosphorylation of the AP-1 transcription factor c-Fos in dendritic cells, which in turn suppresses expression of the $T_h1$-defining cytokine IL-12, thus favoring $T_h2$ bias. However, our results show two significant differences to those reports. First, the Pam-3-cys (a TLR-2 ligand) utilized in those studies showed enhance ERK activation compared to LPS (Dillon et al., 2004) but the cationic lipid-induced ERK activation is less than that observed by LPS. We also examined IL-10, a $T_h2$ cytokine, and the results showed no induction of IL-10 by DOTAP (data not shown). Therefore, the signal of ERK induced by DOTAP is not enough to trigger the $T_h2$ response. Second, DOTAP-induced down-regulation of the IL-1 signal could also suppress the $T_h2$ response. It appears that the DOTAP-induced ERK activation is properly controlled.

Our results suggest that PI-3 kinase is required for DOTAP-induced activation of ERK and induction of CCL2. Further investigation is necessary to identify the precise connection between PI-3 kinase and ERK. Although ELISA data show that PTx inhibits CCL2 release induced by DOTAP, DOTAP-induced ERK phosphorylation is only slightly inhibited by PTx as shown with the Western blot data. Therefore, G protein coupled receptors may or may not be involved in the signal transduction initiated by DOTAP. Interestingly, lysophosphatidycholine (LPC) induces G2A receptor-dependent ERK activation and T cell migration [Radu C. G., et al., *T cell chemotaxis to lysophosphatidylcholine through the G2A receptor*, Proc Natl Acad Sci USA 101:245-50, (2004)]. The authors originally reported that LPC was a ligand of G2A receptor [Kabarowski J. H., et al., *Lysophosphatidylcholine as a ligand for the immunoregulatory receptor G2A*, Science 293:702-5, (2001)], but subsequently, LPC-induced ERK activation was demonstrated through the mechanism of regulating intracellular sequestration and surface expression of G2A receptors [Wang L, et al., *Lysophosphatidylcholine-induced surface redistribution regulates signaling of the murine G protein-coupled receptor G2A*, Mol Biol Cell 16:2234-47, (2005)]. The active cationic lipids contain a large polar head group and two long acyl chains. Such structural characteristics may facilitate their insertion into the lipid membranes, resulting in the possible alteration of spontaneous curvature of the lipid monolayer, as well as the conformational and functional changes of membrane proteins.

Since p38 negatively regulates ERK activation of CCL2 induction, we expected the p38 inhibitor, SB203580, formulated in DOTAP/E7 vaccine could enhance the anti-tumor activity. However, an opposite result was found implying that p38 may also play a positive role in the DOTAP/E7-induced tumor regression. Since cationic liposomes can induce the generation of reactive oxygen species (ROS), which can lead to p38 activation, it is possible that DOTAP induced p38 activation is through ROS (Iwaoka et al., 2006). Accumulated evidence shows that p38 activation induces $T_h1$ cytokine release from dendritic cells [DeSilva D. R., et al., *The p38 mitogen-activated protein kinase pathway in activated and Anergic Th1 cells*, Cell Immunol 180:116-23, (1997); Yu J. J., et al., *Regulation and phenotype of an innate Th1 cell: role of cytokines and the p38 kinase pathway*, J Immunol 171:6112-8, (2003)]. In mammalian species, MAP kinases (ERK, p38 and JNK) are involved in all aspects of the immune response, from the initiation phase of innate immunity, to the activation of the adaptive immunity, and to cell death when immune function is complete [Dong C., et al., *MAP kinases in the immune response*, Annu Rev Immunol 20:55-72, (2002)].

A great variety of experimental adjuvants are available for use in animals and some of them have been tested in clinical trials. They include several water-in-oil emulsions, liposomes, and other chemical adjuvants [Vogel, F. R., and Powell, M. F. *A compendium of vaccine adjuvants and excipients*. Pharm Biotechnol 6:141 (1995)]. However, only influenza virosomes [Gluck, R., and Walti, E., *Biophysical validation of Epaxal Berna, a hepatitis A vaccine adjuvanted with immunopotentiating reconstituted influenza virosomes (IRIV)*. Dev Biol (Basel) 103:189 (2000)] and Chiron's MF59 [Kahn, J. O., et al., *Clinical and immunologic responses to human immunodeficiency virus (HIV) type 1SF2 gp120 subunit vaccine combined with MF59 adjuvant with or without muramyl tripeptide dipalmitoyl phosphatidylethanolamine in non-HIV-infected human volunteers*. J Infect Dis 170:1288 (1994)] are already launched on the market in addition to the aluminum salts. Similar to cationic liposome (unpublished data), the submicron emulsion based adjuvant, MF59, is internalized by dendritic cells [Dupuis, M., et al., *Dendritic cells internalize vaccine adjuvant after intramuscular injection*. Cell Immunol 186:18 (1998)]. It stimulates a variety of immune activities that lead to high antibody and T-cell reactions against co-delivered antigens. However, according to the clinical trial report on HSV and influenza vaccines [Jones, C. A., and Cunningham, A. L., *Vaccination strategies to prevent genital herpes and neonatal herpes simplex virus (HSV) disease*. Herpes 11:12 (2004); and Minutello, M., et al., *Safety and immunogenicity of an inactivated subunit influenza virus vaccine combined with MF59 adjuvant emulsion in elderly subjects, immunized for three consecutive influenza seasons*. Vaccine 17:99 (1999)], evidence from animal models suggests that the MF59 adjuvant enhances neutralizing antibodies rather than T-cell responses. Therefore, cationic liposomes as a vaccine adjuvant is different from MF59 in that it generates a strong cell-mediated immune response as shown by our data.

The cationic lipid/antigen complex appears to be the simplest cancer vaccine formulation ever reported. It only contains two molecules, i.e. an antigen and a carrier. In addition to the delivery of the E7 peptide to the cytoplasm of the antigen presenting cells such as, for example, the dendritic cells, DOTAP must also activate DC. Indeed, liposomes consisting of DOTAP alone induce the expression of CD80/CD86 co-stimulatory molecules in dendritic cells.

In conclusion, our findings suggest for the first time that cationic liposomes are potent immune system stimulators. The results reported herein shed light on the molecular mechanisms of the adjuvant activity of cationic lipids such as, for example, DOTAP.

DOTAP mediates the induction of several chemokines and cytokines whose expression is mediated by the ERK pathway. Our studies also identified the ERK pathway as a new molecular marker for the evaluation of the adjuvant activity of cationic liposomes. These markers may be used for high-throughput screening or design of potent lipid based adjuvants and vaccine delivery systems.

Example 3

Demonstration of the Immunostimulatory Capability of Cationic Lipid/Antigen Complexes in Cells of the Human Immune System 1. Cationic Lipid/E7 Complexes Activate Human Dendritic Cells in a Lipid Dose Dependent Manner Cationic liposomes were prepared as described above. The E7 antigen used in the formulation is the identified human E7 peptide restricted by HLA-A*0201 (HPV-16 E7, amino acids 11-20, YMLDLQPETT (SEQ. ID. NO. 2). The peptide was synthesized by the University of Pittsburgh, Molecular Medicine Institute, Pittsburgh, Pa. Human HLA-A2 human dendritic cells were obtained from Lonza (of Walkersville, Md.). Frozen cryovials were thawed and the dendritic cells were cultured in LGM-3 medium (commercially available from Lonza of Walkersville, Md.) supplemented with 50 microgram/ml IL-4 and GM-CSF at 37° C. and 5% $CO_2$ at an initial plating density of 125,000 cells/cm$^2$ in 2 ml of medium in 12-well tissue culture dishes. The cells were grown for 3 days in culture and appeared as a mixture of adherent and rounded cells by microscopic examination.

The cells were treated on day 3 with a fresh dose of 50 microgram/ml of IL-4 and GM-CSF (all wells) and test wells were treated with either a mixture of interleukin 1-beta ("IL-β"), interleukin 6 ("IL-6") and TNF-α at 10 ng/ml, and prostaglandin E2 ("PGE-2") at 10 µg/ml (positive control for activation), no treatment (negative activation control), and DOTAP/E7 at 2.5, 10 and 40 micromolar final concentrations, DOEPC at 2.5, 10 and 40 micromolar final concentrations, and DOTAP/cholesterol/E7 at 2.5, 10 and 40 micromolar final concentrations of lipid and cholesterol. Cholesterol, a stabilizer of the lipid bilayer, was added at 25 mol %. The treated dendritic cells were maintained in culture for 24 hours and harvested for cell surface marker staining and flow cytometry analysis. The harvested cells were counted by hemacytometer and 10 µl of the following antibody conjugates were added sequentially to each sample for labeling surface markers: CD80-FITC, CD83-APC, and CD86-PE (BD Biosciences). The surface labeled cells were subsequently analyzed by flow cytometry using a BD FACxcaliber flow cytometer, and the co-stimulatory dendritic cell marker molecules CD80, CD83, and CD86 which are produced upon activation, were monitored. As seen in FIGS. 23 A, B, and C primary human dendritic cells treated with the cationic lipid/E7 complex at various lipid doses up-regulated the expression of all three co-stimulatory markers of dendritic cell activation evaluated and required for successful antigen presentation to T-cells. As seen in FIGS. 23 D and E, additional components such as stabilizers can also be included in the pharmaceutical compositions without negatively impacting the immunostimulatory capabilities of the complex.

2. Cationic Lipid/E7 Complexes Activate Human Dendritic Cells and Induce Chemokine and Cytokine Production Human HLA-A2 dendritic cells (Lonza, Walkersville, Md.), were treated and grown in culture as described above. On day 3 the cells were treated with 40 micromolar DOTAP/E7 complex or the potent immunostimulator lipopolysaccharide (LPS) at 50 micromolar concentrations (positive control). Medium from assay wells was removed and centrifuged at 1300 rpm in a microfuge for 5 minutes to pellet unattached dendritic cells. The supernants were removed and treated with 10 microliters per ml of Calbiochem (La Jolla, Calif.) protease inhibitor cocktail set I (Cat. No. 539131) and stored frozen prior to analysis. Samples were analyzed for cytokine expression by Pierce Biotechnology (Woburn, Mass.) using their Searchlight Protein Array Multiplex ELISA assay.

Production of TNF-α and IL-12 were evaluated, and production of selected chemokines known to be essential in the cellular immune response, CCL3, CCL4, CCL5, and CCL19 were all evaluated (FIG. 24A-F). FIG. 24 illustrates that the DOTAP/E7 complex induces cytokine and chemokine production by human dendritic cells. FIGS. 24 A-F illustrates DOTAP/E7 induced production of TNF-α, IL-12, CCL3, CCL4, CC15, and CCL-19 respectively.

Similarly to the observations made with the murine dendritic cells (Example 1), unlike LPS, the DOTAP/E7 complex did not induce significant production of the pro-inflammatory cytokine TNF-α, confirming that in the human system also NF-κB mediated signaling is not activated by the cationic lipids. DOTAP/E7 stimulates effective production of multiple chemokines demonstrating that the cationic lipids act as potent immune stimulators, and provide similar correlates of efficient activation in both murine and human immune cells.

3. Effect of DOTAP/E7 Particle Size on the Activation of Human Dendritic Cells

Human HLA-A2 dendritic cells (Lonza, Walkersville, Md.), were treated and grown in culture as described above. On day 3 the test wells were treated with either a mixture of IL-β, IL-6 and TNF-α at 10 ng/ml, and PGE-2 at 10 µg/ml (positive control for activation), no treatment (negative activation control), the potent immunostimulator lipopolysaccharide (LPS) at 50 micromolar concentrations (second positive control), or 10 micromolar DOTAP/E7 complex with particles sizes 100 nm, 200 nm and 400 nm. The results shown in FIG. 25 demonstrate that the cationic lipid/antigen complexes can be utilized within a broad size range to induce an immune response in the development of immunotherapies.

Discussion

Studies described in Examples 1 and 2 led to the development of an immunotherapy formulation consisting of a cationic lipid/antigen complex. Upon stimulation with cationic lipids such as DOTAP and DOEPC, murine bone marrow derived dendritic cells (BMDC) were activated for the expression of the co-stimulatory molecules, CD80 and CD86 [Vangesseri et al, *Immunostimulation of dendritic cells by cationic liposomes*. Mol Membr Biol 23:385-395 (2006)]. The activation of various components of the MAP kinase signaling pathway and several chemokines such as CCL2 were also observed in DOTAP-activated BMDC. Animal studies suggested that DOTAP liposomes within specific dose ranges acts as both an antigen carrier and a potent adjuvant for inducing migration of the activated dendritic cells to the draining lymph node, thereby leading to the generation of in vivo antigen-specific CD8$^+$ T lymphocyte against antigen-bearing cells such as tumor cells. In vitro testing in activation of primary human dendritic cells indicate that the cationic lipids are potent immunostimulators, promoting dendritic cell activation toward expression of co-stimulatory molecules which are required for T-cell recognition and antigen presentation. We have also demonstrated that human dendritic cells, upon activation by DOTAP/E7 liposomes, promote significant proliferation of human T-cells in vitro.

The studies reported above identify specific unique compositions and applications of cationic liposomes, which can be exploited to develop simple, cost effective, and much needed immunotherapies for several debilitating diseases.

As various changes could be made in the above-described aspects and exemplary embodiments without departing from the scope of the invention, it is intended that all matter contained in the above description shall be interpreted as illustrative and not in a limiting sense. To that end, while the examples primarily discuss the cationic lipids DOTAP, DOEPC, and DOTMA, those skilled in the art will recognize that these cationic lipids are merely exemplary and that the methods are applicable to other cationic lipids.

In compliance with 37 C.F.R. §1.821(f), the applicants submit that the sequence listing information recorded in computer readable form is identical to the written sequence listing.

What is claimed:

1. A method of treating a disease or infection in a mammal, the method comprising administering at least one cationic lipid together with at least one tumor-associated antigen or naturally-occurring microbial antigen, wherein the cationic lipid is administered to the mammal in an amount sufficient to activate the MAP kinase signaling pathway to elicit an immunostimulatory adjuvant effect,
wherein a mouse dose of cationic lipid is between 10 nmol and about 400 nmol,
and wherein the mammal dose of cationic lipid is determined from the mouse dose.

2. The method of claim 1 wherein the cationic lipid is a nonsteroidal cationic lipid comprising at least one fatty acid or alkyl chain.

3. The method of claim 1 wherein the cationic lipid is selected from the group consisting of DOTAP, DOTMA, DOEPC, and combinations thereof.

4. The method of claim 1 wherein the cationic lipid is DOTAP.

5. The method of claim 1 wherein the disease is cancer.

6. The method of claim 1 wherein the antigen is modified to increase its hydrophobicity, wherein the antigen is modified via conjugation to a lipid chain or via conjugation to one or more hydrophobic amino acids.

7. The method of claim 6 wherein the antigen is a lipidated antigen.

8. The method of claim 7 wherein the antigen is lipidated with palmitic acid.

9. The method of claim 8 wherein the palmitic acid is linked to the antigen via a spacer, wherein the spacer is an amino acid sequence of K-S-S.

10. A method of reducing the regulatory T-cell population in a mammal in need thereof, the method comprising administering to the mammal at least one cationic lipid and at least one tumor-associated antigen or naturally-occurring microbial antigen,
wherein a mouse dose of cationic lipid is between 10 nmol and about 400 nmol,
and wherein the mammal dose of cationic lipid is determined from the mouse dose.

11. The method of claim 10 wherein the cationic lipid is a nonsteroidal cationic lipid comprising at least one fatty acid or alkyl chain.

12. The method of claim 10 wherein the cationic lipid is selected from the group consisting of DOTAP, DOTMA, DOEPC, and combinations thereof.

13. The method of claim 10 wherein the cationic lipid is DOTAP.

14. A method of using a cationic lipid to elicit an immunostimulatory adjuvant effect in an immune system of a mammal, wherein the cationic lipid is administered with at least one tumor-associated antigen or naturally-occurring microbial antigen to the mammal in an amount sufficient to activate the MAP kinase signaling pathway to elicit the immunostimulatory adjuvant effect,
wherein a mouse dose of cationic lipid is between 10 nmol and about 400 nmol,
and wherein the mammal dose of cationic lipid is determined from the mouse dose.

15. The method of claim 14 wherein the cationic lipid is a nonsteroidal cationic lipid comprising at least one fatty acid or alkyl chain.

16. The method of claim 14 wherein the cationic lipid is selected from the group consisting of DOTAP, DOTMA, DOEPC, and combinations thereof.

17. The method of claim 14 wherein the cationic lipid is DOTAP.

18. The method of claim 1 wherein the amount of cationic lipid is between about 30 nmol and about 300 nmol.

19. The method of claim 10 wherein the amount of cationic lipid is between about 30 nmol and about 300 nmol.

20. The method of claim 14 wherein the amount of cationic lipid is between about 30 nmol and about 300 nmol.

21. A method of inducing an antibody response against an antigen in a mammal, the method comprising administering at least one cationic lipid together with at least one tumor-associated antigen or naturally-occurring microbial antigen, wherein the cationic lipid is administered to the mammal in an amount sufficient to induce the antibody response in response against the antigen,
wherein a mouse dose of cationic lipid is between 10 nmol and about 400 nmol,
and wherein the mammal dose of cationic lipid is determined from the mouse dose.

22. The method of claim 21 wherein the cationic lipid is a nonsteroidal cationic lipid comprising at least one fatty acid or alkyl chain.

23. The method of claim 21 wherein the cationic lipid is selected from the group consisting of DOTAP, DOTMA, DOEPC, and combinations thereof.

24. The method of claim 21 wherein the cationic lipid is DOTAP.

25. The method of claim 21 wherein the antigen is modified to increase its hydrophobicity, wherein the antigen is modified via conjugation to a lipid chain or via conjugation to one or more hydrophobic amino acids.

26. The method of claim 25 wherein the antigen is a lipidated antigen, and wherein the lipidated antigen is lipidated with palmitic acid.

27. The method of claim 26 wherein the palmitic acid is linked to the antigen via a spacer, wherein the spacer is an amino acid sequence of K-S-S.

28. The method of claim 21 wherein the amount of cationic lipid is between about 30 nmol and about 300 nmol.

29. The method of claim 1, wherein the mammal is a human.

30. The method of claim 1, wherein the mammal is a non-human.

31. The method of claim 1, wherein the mouse dose of cationic lipid is between 0.05 nmol per microliter (µL) to about 3 nmol per µL.

32. The method of claim 1, wherein the mouse dose of cationic lipid is between 0.05 mg per milliliter (mL) to about 2 mg per mL.

33. The method of claim 10, wherein the mammal is a human.

34. The method of claim 10, wherein the mammal is a non-human.

35. The method of claim 10, wherein the mouse dose of cationic lipid is between 0.05 nmol per microliter (µL) to about 3 nmol per µL.

36. The method of claim 10, wherein the mouse dose of cationic lipid is between 0.05 mg per milliliter (mL) to about 2 mg per mL.

37. The method of claim 14, wherein the mammal is a human.

38. The method of claim 14, wherein the mammal is a non-human.

39. The method of claim 14, wherein the mouse dose of cationic lipid is between 0.05 nmol per microliter (µL) to about 3 nmol per µL.

40. The method of claim 14, wherein the mouse dose of cationic lipid is between 0.05 mg per milliliter (mL) to about 2 mg per mL.

41. The method of claim 21, wherein the mammal is a human.

42. The method of claim 21, wherein the mammal is a non-human.

43. The method of claim 21, wherein the mouse dose of cationic lipid is between 0.05 nmol per microliter (µL) to about 3 nmol per µL.

44. The method of claim 21, wherein the mouse dose of cationic lipid is between 0.05 mg per milliliter (mL) to about 2 mg per mL.

* * * * *

UNITED STATES PATENT AND TRADEMARK OFFICE
CERTIFICATE OF CORRECTION

PATENT NO. : 8,877,206 B2
APPLICATION NO. : 12/049957
DATED : November 4, 2014
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1198 days.

Signed and Sealed this
Sixth Day of June, 2017

Michelle K. Lee
*Director of the United States Patent and Trademark Office*

```
                          SEQUENCE LISTING

<160> NUMBER OF SEQ ID NOS: 9

<210> SEQ ID NO 1
<211> LENGTH: 9
<212> TYPE: PRT
<213> ORGANISM: Human papillomavirus type 16

<400> SEQUENCE: 1

Arg Ala His Tyr Asn Ile Val Thr Phe
1               5

<210> SEQ ID NO 2
<211> LENGTH: 10
<212> TYPE: PRT
<213> ORGANISM: Human papillomavirus type 16

<400> SEQUENCE: 2

Tyr Met Leu Asp Leu Gln Pro Glu Thr Thr
1               5                   10

<210> SEQ ID NO 3
<211> LENGTH: 20
<212> TYPE: DNA
<213> ORGANISM: Mus musculus

<400> SEQUENCE: 3
aagccagctc tctcttcctc                                          20

<210> SEQ ID NO 4
<211> LENGTH: 21
<212> TYPE: DNA
<213> ORGANISM: Mus musculus

<400> SEQUENCE: 4
cctctctctt tgagcttggt g                                        21

<210> SEQ ID NO 5
<211> LENGTH: 20
<212> TYPE: DNA
<213> ORGANISM: Mus musculus

<400> SEQUENCE: 5
atcatgaagg tctccaccac                                          20

<210> SEQ ID NO 6
<211> LENGTH: 20
<212> TYPE: DNA
<213> ORGANISM: Mus musculus

<400> SEQUENCE: 6
tctcaggcat tcagttccag                                          20

<210> SEQ ID NO 7
<211> LENGTH: 20
<212> TYPE: DNA
<213> ORGANISM: Mus musculus

<400> SEQUENCE: 7
gctctgtgca aacctaaccc                                          20
```

```
<210> SEQ ID NO 8
<211> LENGTH: 22
<212> TYPE: DNA
<213> ORGANISM: Mus musculus

<400> SEQUENCE: 8
tgtgatggtg ggaatgggtc ag                                              22

<210> SEQ ID NO 9
<211> LENGTH: 22
<212> TYPE: DNA
<213> ORGANISM: Mus musculus

<400> SEQUENCE: 9
tttgatgtca cgcacgattt cc                                              22
```